United States Patent
Toriyabe et al.

(10) Patent No.: US 7,872,036 B2
(45) Date of Patent: Jan. 18, 2011

(54) 3-TRIAZOLYLPHENYL SULFIDE DERIVATIVE AND INSECTICIDE, MITICIDE AND NEMATICIDE CONTAINING IT AS AN ACTIVE INGREDIENT

(75) Inventors: Keiji Toriyabe, Iwata (JP); Mikio Yamaguchi, Iwata (JP); Yoshihiro Ito, Taitoh-ku (JP); Shiori Kinpara, Taitoh-ku (JP); Hiroyuki Yano, Taitoh-ku (JP); Satoru Takahashi, Taitoh-ku (JP); Norihisa Yonekura, Taitoh-ku (JP); Ryuji Hamaguchi, Taitoh-ku (JP)

(73) Assignees: Kumiai Chemical Industry Co., Ltd., Tokyo (JP); Ihara Chemical Industry Co., Ltd., Tokyo (JP)

( * ) Notice: Subject to any disclaimer, the term of this patent is extended or adjusted under 35 U.S.C. 154(b) by 458 days.

(21) Appl. No.: 11/577,670

(22) PCT Filed: Oct. 20, 2005

(86) PCT No.: PCT/JP2005/019315

§ 371 (c)(1),
(2), (4) Date: Apr. 20, 2007

(87) PCT Pub. No.: WO2006/043635

PCT Pub. Date: Apr. 27, 2006

(65) Prior Publication Data

US 2009/0076282 A1    Mar. 19, 2009

(30) Foreign Application Priority Data

Oct. 20, 2004   (JP) ............................. 2004-305251

(51) Int. Cl.
  *A01N 43/653*   (2006.01)
  *C07D 249/14*   (2006.01)
  *C07D 249/12*   (2006.01)

(52) U.S. Cl. .................... 514/383; 514/384; 548/263.8; 548/264.8; 548/265.6

(58) Field of Classification Search .............. 548/263.4, 548/263.8, 264.2, 264.4, 264.8, 265.4, 265.8, 548/266.8, 269.4, 267.8, 265.6; 514/383, 514/384
See application file for complete search history.

(56) References Cited

U.S. PATENT DOCUMENTS

| 4,795,484 | A  | 1/1989 | Aoki et al. |
| 6,509,354 | B1 | 1/2003 | Toriyabe et al. |
| 6,858,639 | B2 | 2/2005 | Toriyabe et al. |
| 7,037,930 | B2 | 5/2006 | Toriyabe et al. |

FOREIGN PATENT DOCUMENTS

| DE | 195 48 415 | 6/1997 |
| EP | 1 076 053 A1 | 2/2001 |
| JP | 1 230562 | 9/1989 |
| JP | 2 91061 | 3/1990 |
| JP | 2 91062 | 3/1990 |
| JP | 7 258227 | 10/1995 |
| JP | 2000-198768 | 7/2000 |
| JP | 2000 239262 | 9/2000 |
| WO | WO 99/03845 | 1/1999 |
| WO | 99 55668 | 11/1999 |

*Primary Examiner*—Patricia L Morris
(74) *Attorney, Agent, or Firm*—Oblon, Spivak, McClelland, Maier & Neustadt, L.L.P.

(57) ABSTRACT

To provide novel 3-triazolylphenyl sulfide derivatives having excellent soil treatment activity as insecticides, miticides or nematicides for agricultural and horticultural plants.

3-Triazolylphenyl sulfide derivatives represented by the formula [1]:

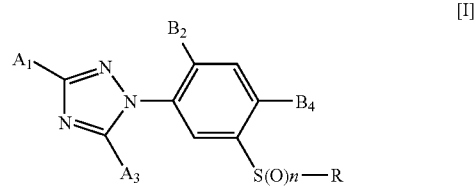

[I]

wherein R is a cyclopropylmethyl group or a trifluoroethyl group, $B_2$ is a hydrogen atom, a halogen atom or a methyl group, $B_4$ is a halogen atom, a cyano group, a nitro group or a $C_1$-$C_6$ alkyl group, and each of $A_1$ and $A_3$ is a hydrogen atom, a halogen atom, a $C_1$-$C_6$ alkyl group which may be substituted or an amino group which may be substituted.

12 Claims, No Drawings

3-TRIAZOLYLPHENYL SULFIDE DERIVATIVE AND INSECTICIDE, MITICIDE AND NEMATICIDE CONTAINING IT AS AN ACTIVE INGREDIENT

TECHNICAL FIELD

The present invention relates to novel 3-triazolylphenyl sulfide derivatives and insecticides, miticides and nematicides for agricultural and horticultural containing them as an active ingredient.

BACKGROUND ART

As known insecticides, miticides and nematicides, 3-triazolylphenyl sulfide derivatives as disclosed in Patent Document 1 have already been known. It is disclosed that the group of compounds as disclosed in the document have high effects against mites when directly sprayed over plants. However, the document does not disclose a soil treatment. The group of compounds as disclosed in the document have insufficient migration in the soil and infiltration into plants by a soil treatment. Accordingly, no sufficient effects may be obtained in some cases, due to non uniform spraying with chemicals, transpiration, photolysis, outflow of the chemicals by rain, etc.

At present, very few miticides having practical soil treatment activity have been known. Chemicals applicable to a soil treatment are advantageous to farmers in view of higher safety, more saving of labor, etc. Accordingly, development of miticides having soil treatment activity has been required.

Patent document 1: JP-A-2000-198768

DISCLOSURE OF THE INVENTION

Problems that the Invention is to Solve

Under these circumstances, an object of the present invention is to solve the above problems of conventional insecticides, miticides and nematicides, and to provide insecticides, miticides and nematicides excellent in safety, pesticidal effects, residual effectiveness, etc.

Means of Solving the Problems

The present inventors have synthesized various 3-triazolylphenyl sulfide derivatives and studied their physiological activities to develop insecticides, miticides and nematicides having the above preferred characteristics. As a result, they have found that the following novel 3-triazolylphenyl sulfide derivatives of the present invention (hereinafter sometimes referred to as compounds of the present invention) exhibit outstanding effects on various farm and garden pests, especially mites represented by two-spotted spider mite, Kanazawa spider mite and citrus red mite, pest lepidopterans represented by diamondbackmoth, Asiatic rice borer and beat armyworm, pest hemipterans represented by brown rice planthopper, green rice leafhopper and cotton aphid, pest coleoptera represented by adzuki bean weevil and nematodes represented by southern root-knot nematode, and have soil treatment activity with which safe and labor-saving application becomes possible. The present invention has been accomplished on the basis of these discoveries.

That is, the present invention provides the following.
(1) 3-Triazolylphenyl sulfide derivative represented by the formula [I]:

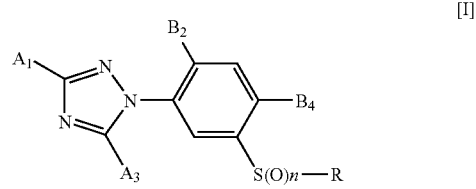

wherein R is a cyclopropylmethyl group or a trifluoroethyl group;
n is an integer of from 0 to 1;
$A_1$ and $A_3$ are selected from groups of Group I and Group II, provided that at least one of them is selected from groups of Group II;
$B_2$ is a hydrogen atom, a halogen atom or a methyl group; and
$B_4$ is a halogen atom, a cyano group, a nitro group or a $C_1$-$C_6$ alkyl group (which may be mono- or poly-substituted by halogen atoms);
provided that when $A_3$ is $NH_2$, $B_2$ is a halogen atom or a methyl group:

(Group I)
a hydrogen atom, a halogen atom, a $C_1$-$C_6$ alkyl group (which may be mono- or poly-substituted by halogen atoms, hydroxyl groups, cyano groups, $C_2$-$C_7$ alkoxycarbonyl groups or $C_1$-$C_6$ alkoxy groups), a $C_3$-$C_8$ cycloalkyl group (which may be mono- or poly-substituted by alkyl groups, halogen atoms, cyano groups or $C_1$-$C_6$ alkoxy groups), a $C_2$-$C_6$ alkenyl group (which may be mono- or poly-substituted by halogen atoms or cyano groups), a $C_2$-$C_6$ alkynyl group (which may be mono- or poly-substituted by halogen atoms or cyano groups), a $C_1$-$C_6$ alkoxy group (which may be mono- or poly-substituted by halogen atoms, cyano groups, $C_2$-$C_5$ alkoxycarbonyl groups or $C_1$-$C_3$ alkoxy groups), a $C_1$-$C_6$ alkylthio group (which may be mono- or poly-substituted by halogen atoms, $C_1$-$C_3$ alkoxy groups, $C_3$-$C_8$ cycloalkyl groups which may be substituted by halogen atoms, or cyano groups), a $C_1$-$C_6$ alkylsulfinyl group (which may be mono- or poly-substituted by halogen atoms, $C_1$-$C_3$ alkoxy groups, $C_3$-$C_8$ cycloalkyl groups which may be substituted by halogen atoms, or cyano groups), a $C_1$-$C_6$ alkylsulfonyl group (which may be mono- or poly-substituted by halogen atoms, $C_1$-$C_3$ alkoxy groups or $C_3$-$C_8$ cycloalkyl groups which may be substituted by halogen atoms), a $C_2$-$C_6$ alkynylthio group (which may be mono- or poly-substituted by halogen atoms, $C_1$-$C_3$ alkoxy groups or cyano groups), a $C_2$-$C_6$ alkynylsulfinyl group (which may be mono- or poly-substituted by halogen atoms, $C_1$-$C_3$ alkoxy groups or cyano groups), a $C_1$-$C_7$ acyl group and a $C_2$-$C_5$ haloalkylcarbonyl group;

(Group II)
a nitro group, a cyano group, a —N=$CR_1R_2$ group, a —N=C($NR_2$'$R_3$')$NR_2R_3$ group, a —N($SO_2R_2$) $R_3$ group, a —N($OR_3$) $R_3$' group, a —C(=O)$OR_2$ group, a —C(=O)$NR_2R_3$ group, a —$SO_2NR_2R_3$ group, a —$NR_2R_3$ group, a —N($COR_2$)$R_3$ group and a —N($COOR_2$)$R_3$ group;
wherein $R_1$ is a hydrogen atom, a $C_1$-$C_6$ alkyl group (which may be mono- or poly-substituted by halogen atoms, hydroxyl groups, cyano groups, $C_2$-$C_7$ alkoxycarbonyl groups or $C_1$-$C_6$ alkoxy groups), a $C_3$-$C_6$ alkenyl group (which may be mono- or poly-substituted by halogen atoms or cyano groups), a $C_3$-$C_6$ alkynyl group (which may be mono- or poly-substituted by halogen atoms or cyano groups), a $C_3$-$C_6$ cycloalkyl group (which may be mono- or poly-substituted by halogen atoms, hydroxyl groups, cyano groups, $C_2$-$C_7$ alkoxycarbonyl groups or $C_1$-$C_6$ alkoxy groups) an arylalkyl group (which may be mono- or poly-substituted by halogen atoms, cyano groups, $C_1$-$C_6$ alkyl groups, $C_1$-$C_6$ haloalkyl groups, $C_2$-$C_7$ alkoxycarbonyl groups or $C_1$-$C_6$ alkoxy groups), a heteroarylalkyl group (which may be mono- or poly-substituted by halogen atoms, cyano groups, $C_1$-$C_6$ alkyl groups, $C_1$-$C_6$ haloalkyl groups, $C_2$-$C_7$ alkoxycarbonyl groups or $C_1$-$C_6$ alkoxy groups), an aryl group (which may be mono- or poly-substituted by halogen atoms, cyano groups, $C_1$-$C_6$ alkyl groups, $C_1$-$C_6$ haloalkyl groups, $C_2$-$C_7$ alkoxycarbonyl groups, $C_1$-$C_6$ alkoxy groups or hydroxyl groups), a heteroaryl group (which may be mono- or poly-substituted by halogen atoms, cyano groups, $C_1$-$C_6$ alkyl groups, $C_1$-$C_6$ haloalkyl groups, $C_2$-$C_7$ alkoxycarbonyl groups or $C_1$-$C_6$ alkoxy groups), a $C_1$-$C_6$ alkoxy group, a $C_1$-$C_6$ alkylthio group, an amino group, a $C_1$-$C_6$ monoalkylamino group or a $C_2$-$C_{12}$ dialkylamino group;

each of $R_2$ and $R_2'$ is a hydrogen atom, a $C_1$-$C_6$ alkyl group (which may be mono- or poly-substituted by halogen atoms, hydroxyl groups, cyano groups, $C_2$-$C_7$ alkoxycarbonyl groups or $C_1$-$C_6$ alkoxy groups), a $C_3$-$C_6$ alkenyl group (which may be mono- or poly-substituted by halogen atoms or cyano groups), a $C_3$-$C_6$ alkynyl group (which may be mono- or poly-substituted by halogen atoms or cyano groups), a $C_3$-$C_6$ cycloalkyl group (which may be mono- or poly-substituted by halogen atoms, hydroxyl groups, cyano groups, $C_2$-$C_7$ alkoxycarbonyl groups or $C_1$-$C_6$ alkoxy groups) an amino group, a $C_1$-$C_6$ monoalkylamino group, a $C_2$-$C_{12}$ dialkylamino group, an arylalkyl group (which may be mono- or poly-substituted by halogen atoms, cyano groups, $C_1$-$C_6$ alkyl groups, $C_1$-$C_6$ haloalkyl groups, $C_2$-$C_7$ alkoxycarbonyl groups or $C_1$-$C_6$ alkoxy groups), a heteroarylalkyl group (which may be mono- or poly-substituted by halogen atoms, cyano groups, $C_1$-$C_6$ alkyl groups, $C_1$-$C_6$ haloalkyl groups, $C_2$-$C_7$ alkoxycarbonyl groups or $C_1$-$C_6$ alkoxy groups), an aryl group (which may be mono- or poly-substituted by halogen atoms, cyano groups, $C_1$-$C_6$ alkyl groups, $C_1$-$C_6$ haloalkyl groups, $C_2$-$C_7$ alkoxycarbonyl groups or $C_1$-$C_6$ alkoxy groups) or a heteroaryl group (which may be mono- or poly-substituted by halogen atoms, cyano groups, $C_1$-$C_6$ alkyl groups, $C_1$-$C_6$ haloalkyl groups, $C_2$-$C_7$ alkoxycarbonyl groups or $C_1$-$C_6$ alkoxy groups);

each of $R_3$ and $R_3'$ is a hydrogen atom, a $C_1$-$C_6$ alkyl group (which may be mono- or poly-substituted by halogen atoms, hydroxyl groups, cyano groups, $C_2$-$C_7$ alkoxycarbonyl groups or $C_1$-$C_6$ alkoxy groups), a $C_3$-$C_6$ alkenyl group (which may be mono- or poly-substituted by halogen atoms or cyano groups), a $C_3$-$C_6$ alkynyl group (which may be mono- or poly-substituted by halogen atoms or cyano groups) or a $C_3$-$C_6$ cycloalkyl group (which may be mono- or poly-substituted by halogen atoms, hydroxyl groups, cyano groups, $C_2$-$C_7$ alkoxycarbonyl groups or $C_1$-$C_6$ alkoxy groups); and Q is an oxygen atom or a sulfur atom;

provided that $R_1$ and $R_2$ in the —N=$CR_1R_2$ group may form a 5 to 6-membered ring together with the carbon atom to which they are bonded, $R_2$ and $R_3$, or $R_2'$ and $R_3'$, in the —N=C($NR_2'R_3'$)$NR_2R_3$ group may form a 5 to 6-membered ring together with the nitrogen atom to which they are bonded, and $R_2$ and $R_3$ in the —$NR_2R_3$ group may form a 5 to 6-membered ring together with the nitrogen atom to which they are bonded.

(2) The 3-triazolylphenyl sulfide derivative according to the above (1), wherein R is a trifluoroethyl group;

n is an integer of from 0 to 1;

$A_1$ is a $C_1$-$C_6$ alkyl group (which may be mono- or poly-substituted by halogen atoms or cyano groups), a $C_1$-$C_6$ alkylthio group (which may be mono- or poly-substituted by halogen atoms) or a $C_1$-$C_6$ alkylsulfinyl group (which may be mono- or poly-substituted by halogen atoms or $C_1$-$C_3$ alkoxy groups);

$A_3$ is the group —$NR_2R_3$ or the group —N(COR$_2$)$R_3$;

each of $R_2$ and $R_3$ which are independent of each other, is a hydrogen atom, a $C_1$-$C_6$ alkylamino group, a $C_1$-$C_6$ alkyl group (which may be mono- or poly-substituted by halogen atoms or cyano groups) or a $C_3$-$C_6$ alkynyl group (which may be mono- or poly-substituted by halogen atoms or cyano groups), provided that $R_2$ and $R_3$ are not simultaneously hydrogen atoms;

$B_2$ is a hydrogen atom, a halogen atom or a methyl group; and $B_4$ is a cyano group or a $C_1$-$C_6$ alkyl group (which may be mono- or poly-substituted by halogen atoms).

(3) The 3-triazolylphenyl sulfide derivative according to the above (1), wherein R is a trifluoroethyl group;

n is an integer of from 0 to 1;

$A_1$ is a $C_1$-$C_6$ alkyl group (which may be mono- or poly-substituted by halogen atoms or cyano groups), a $C_1$-$C_6$ alkylthio group (which may be mono- or poly-substituted by halogen atoms) or a $C_1$-$C_6$ alkylsulfinyl group (which may be mono- or poly-substituted by halogen atoms or $C_1$-$C_3$ alkoxy groups);

$A_3$ is an amino group;

$B_2$ is a halogen atom or a methyl group; and $B_4$ is a cyano group or a $C_1$-$C_6$ alkyl group (which may be mono- or poly-substituted by halogen atoms).

(4) The 3-triazolylphenyl sulfide derivative according to the above (2), wherein $A_1$ is an isopropyl group, a t-butyl group, a difluoromethyl group, a trifluoromethyl group, a trifluoromethylthio group, a 2,2,2-trifluoroethylthio group, a 1,1,2,2-tetrafluoroethylthio group, a pentafluoroethylthio group, a trifluoromethylsulfinyl group, a 2,2,2-trifluoroethylsulfinyl group or a pentafluoroethylsulfinyl group; and $A_3$ is a methylamino group, an ethylamino group, a propylamino group, a cyanomethylamino group, a propargylamino group, an acetylamino group, a propionylamino group, a trifluoroacetylamino group or a difluoroacetylamino group.

(5) The 3-triazolylphenyl sulfide derivative according to the above (3), wherein $A_1$ is an isopropyl group, a t-butyl group, a difluoromethyl group, a trifluoromethyl group, a trifluoromethylthio group, a 2,2,2-trifluoroethylthio group, a 1,1,2,2-tetrafluoroethylthio group, a pentafluoroethylthio group, a trifluoromethylsulfinyl group, a 2,2,2-trifluoroethylsulfinyl group or a pentafluoroethylsulfinyl group; and $A_3$ is an amino group.

(6) The 3-triazolylphenyl sulfide derivative according to the above (2), wherein $A_1$ is a trifluoromethyl group, a trifluoromethylthio group or a 2,2,2-trifluoroethylsulfinyl group; and $A_3$ is a methylamino group or a trifluoroacetylamino group.

(7) The 3-triazolylphenyl sulfide derivative according to the above (2), wherein $A_1$ is a trifluoromethyl group, a trifluoromethylthio group or a 2,2,2-trifluoroethylsulfinyl group; and $A_3$ is an amino group.

(8) An aniline derivative represented by the formula [I-a] which is an intermediate for production of the 3-triazolylphenyl sulfide derivative as defined in any one of the above (1) to (7):

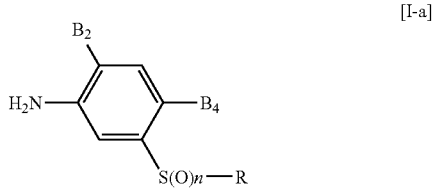

[I-a]

wherein $B_2$ is a halogen atom or a methyl group, and $B_4$ is a $C_1$-$C_6$ alkyl group.
(9) The aniline derivative according to the above (8), wherein $B_4$ is a methyl group.
10. An insecticide, miticide or nematicide for agricultural and horticultural containing the 3-triazolylphenyl sulfide derivative as defined in any one of the above (1) to (7) as an active ingredient.

EFFECTS OF THE INVENTION

The compounds of the present invention exhibit excellent pesticidal effects against a wide range of pests including pest hemiptera, pest lepidoptera, pest coleoptera, pest diptera, pest hymenoptera, pest orthoptera, pest isoptera, pest thysanoptera, mites and plant-parasitic nematodes, and they are also capable of controlling pests which have acquired resistance to conventional pesticides.

Particularly, the compounds of the present invention exhibit outstanding effects on various pests, especially on farm and garden pests including mites represented by twospotted spider mite, Kanazawa spider mite and citrus red mite, pest lepidopterans represented by diamondbackmoth, Asiatic rice borer and beat armyworm, pest hemipterans represented by brown rice planthopper, green rice leafhopper and cotton aphid, pest coleoptera represented by adzuki bean weevil and nematodes represented by southern root-knot nematode, and they are excellent in systemic action. Accordingly, they can be used for a safe and labor-saving application by a soil treatment.

BEST MODE FOR CARRYING OUT THE INVENTION

The symbols and the terms used in this specification will be defined below.

The halogen atom represents a fluorine atom, a chlorine atom, a bromine atom or a iodine atom.

The expression $C_1$-$C_6$, etc. represents that the subsequent substituent has from 1 to 6 carbon atoms in this case.

The $C_1$-$C_6$ alkyl group means, unless otherwise specified, a linear or branched alkyl group having from 1 to 6 carbon atoms, such as a methyl, ethyl, n-propyl, i-propyl, n-butyl, s-butyl, i-butyl, t-butyl, n-pentyl, 1-methylbutyl, 2-methylbutyl, 3-methylbutyl, 1-ethylpropyl, 1,1-dimethylpropyl, 1,2-dimethylpropyl, neopentyl, n-hexyl, 1-methylpentyl, 2-methylpentyl, 3-methylpentyl, 4-methylpentyl, 1-ethylbutyl, 2-ethylbutyl, 1,1-dimethylbutyl, 1,2-dimethylbutyl, 1,3-dimethylbutyl, 2,2-dimethylbutyl, 2,3-dimethylbutyl, 3,3-dimethylbutyl, 1,1,2-trimethylpropyl, 1,2,2-trimethylpropyl, 1-ethyl-1-methylpropyl or 1-ethyl-2-methylpropyl group.

The $C_3$-$C_6$ cycloalkyl group means, unless otherwise specified, a cycloalkyl group having from 3 to 6 carbon atoms, such as a cyclopropyl, cyclobutyl, cyclopentyl or cyclohexyl group.

The $C_2$-$C_6$ alkenyl group means, unless otherwise specified, a linear or branched alkenyl group having from 2 to 6 carbon atoms, such as a vinyl, 1-propenyl, i-propenyl, 2-propenyl, 1-butenyl, 1-methyl-1-propenyl, 2-butenyl, 1-methyl-2-propenyl, 3-butenyl, 2-methyl-1-propenyl, 2-methyl-2-propenyl, 1,3-butadienyl, 1-pentenyl, 1-ethyl-2-propenyl, 2-pentenyl, 1-methyl-1-butenyl, 3-pentenyl, 1-methyl-2-butenyl, 4-pentenyl, 1-methyl-3-butenyl, 3-methyl-1-butenyl, 1,2-dimethyl-2-propenyl, 1,1-dimethyl-2-propenyl, 2-methyl-2-butenyl, 3-methyl-2-butenyl, 1,2-dimethyl-1-propenyl, 2-methyl-3-butenyl, 3-methyl-3-butenyl, 1,3-pentadienyl, 1-vinyl-2-propenyl, 1-hexenyl, 1-propyl-2-propenyl, 2-hexenyl, 1-methyl-1-pentenyl, 1-ethyl-2-butenyl, 3-hexenyl, 4-hexenyl, 5-hexenyl, 1-methyl-4-pentenyl, 1-ethyl-3-butenyl, 1-(i-butyl)vinyl, 1-ethyl-1-methyl-2-propenyl, 1-ethyl-2-methyl-2-propenyl, 1-(i-propyl)-2-propenyl, 2-methyl-2-pentenyl, 3-methyl-3-pentenyl, 4-methyl-3-pentenyl, 1,3-dimethyl-2-butenyl, 1,1-dimethyl-3-butenyl, 3-methyl-4-pentenyl, 4-methyl-4-pentenyl, 1,2-dimethyl-3-butenyl, 1,3-dimethyl-3-butenyl, 1,1,2-trimethyl-2-propenyl, 1,5-hexadienyl, 1-vinyl-3-butenyl or 2,4-hexadienyl group.

The $C_3$-$C_6$ alkynyl group means, unless otherwise specified, a linear or branched alkynyl group having from 2 to 6 carbon atoms, such as an ethynyl, 1-propynyl, 2-propynyl, 1-butynyl, 1-methyl-2-propynyl, 2-butynyl, 3-butynyl, 1-pentynyl, 1-ethyl-2-propynyl, 2-pentynyl, 3-pentynyl, 1-methyl-2-butynyl, 4-pentynyl, 1-methyl-3-butynyl, 2-methyl-3-butynyl, 1-hexynyl, 1-(n-propyl)-2-propynyl, 2-hexynyl, 1-ethyl-2-butynyl, 3-hexynyl, 1-methyl-2-pentynyl, 1-methyl-3-pentynyl, 4-methyl-1-pentynyl, 3-methyl-1-pentynyl, 5-hexynyl, 1-ethyl-3-butynyl, 1-ethyl-1-methyl-2-propynyl, 1-(i-propyl)-2-propynyl, 1,1-dimethyl-2-butynyl or 2,2-dimethyl-3-butynyl group.

The $C_1$-$C_6$ haloalkyl group means, unless otherwise specified, a $C_1$-$C_4$ linear or branched alkyl group substituted by from 1 to 9 identical or different halogen atoms, such as a fluoromethyl, chloromethyl, bromomethyl, difluoromethyl, dichloromethyl, trifluoromethyl, trichloromethyl, chlorodifluoromethyl, bromodifluoromethyl, 2-fluoroethyl, 1-chloroethyl, 2-chloroethyl, 1-bromoethyl, 2-bromoethyl, 2,2-difluoroethyl, 1,2-dichloroethyl, 2,2-dichloroethyl, 2,2,2-trifluoroethyl, 2,2,2-trichloroethyl, 1,1,2,2-tetrafluoroethyl, pentafluoroethyl, 2-bromo-2-chloroethyl, 2-chloro-1,1,2,2-tetrafluoroethyl, 1-chloro-1,2,2,2-tetrafluoroethyl, 1-chloropropyl, 2-chloropropyl, 3-chloropropyl, 2-bromopropyl, 3-bromopropyl, 2-bromo-1-methylethyl, 3-iodopropyl, 2,3-dichloropropyl, 2,3-dibromopropyl, 3,3,3-trifluoropropyl, 3,3,3-trichloropropyl, 3-bromo-3,3-difluoropropyl, 3,3-dichloro-3-fluoropropyl, 2,2,3,3-tetrafluoropropyl, 1-bromo-3,3,3-trifluoropropyl, 2,2,3,3,3-pentafluoropropyl, 2,2,2-trifluoro-1-trifluoromethylethyl, heptafluoropropyl, 1,2,2,2-tetrafluoro-1-trifluoromethylethyl, 2,3-dichloro-1,1,2,3,3-pentafluoropropyl, 2-chlorobutyl, 3-chlorobutyl, 4-chlorobutyl, 2-chloro-1,1-dimethylethyl, 4-bromobutyl, 3-bromo-2-methylpropyl, 2-bromo-1,1-dimethylethyl, 2,2-dichloro-1,1-dimethylethyl, 2-chloro-1-chloromethyl-2-methylethyl, 4,4,4-trifluorobutyl, 3,3,3-trifluoro-1-methylpropyl, 3,3,3-trifluoro-2-methylpropyl, 2,3,4-trichlorobutyl, 2,2,2-trichloro-1,1-dimethylethyl, 4-chloro-4,4-difluorobutyl, 4,4-dichloro-4-fluorobutyl, 4-bromo-4,4-difluorobutyl, 2,4-dibromo-4,4-difluorobutyl, 3,4-dichloro-3,4,4-trifluorobutyl, 3,3-dichloro-4,4,4-trifluorobutyl, 4-bromo-3,3,4,4-tetrafluorobutyl, 4-bromo-3-chloro-3,4,4-trifluorobutyl, 2,2,3, 3,4,4-hexafluorobutyl, 2,2,3,4,4,4-hexafluorobutyl, 2,2,2-trifluoro-1-methyl-1-trifluoromethylethyl, 3,3,3-trifluoro-2-trifluoromethylpropyl, 2,2,3,3,4,4,4-heptafluorobutyl, 2,3,3,3-tetrafluoro-2-trifluoromethylpropyl, 1,1,2,2,3,3,4,4-octafluorobutyl, nonafluorobutyl or 4-chloro-1,1,2,2,3,3,4,4-octafluorobutyl group.

The $C_1$-$C_6$ alkoxy group means an (alkyl)-O— group wherein the alkyl moiety is as defined above, such as a methoxy, ethoxy, n-propoxy, i-propoxy, n-butoxy, i-butoxy, t-butoxy, pentyloxy, i-pentyloxy or hexyloxy group.

The $C_1$-$C_6$ alkoxy $C_1$-$C_6$ alkyl group means an alkyl group having from 1 to 6 carbon atoms substituted by an alkoxy having from 1 to 6 carbon atoms wherein the alkyl moiety and the alkoxy moiety are as defined above, such as a methoxymethyl, ethoxymethyl, i-propoxymethyl, n-butoxymethyl, i-butoxymethyl, pentyloxymethyl, methoxyethyl, n-butoxyethyl or i-butoxyethyl group.

The $C_1$-$C_6$ alkylthio group means an (alkyl)-S— group having from 1 to 6 carbon atoms wherein the alkyl moiety is as defined above, such as methylthio, ethylthio, n-propylthio or isopropylthio.

The $C_1$-$C_6$ alkylsulfinyl group means an (alkyl)-SO— group having from 1 to 6 carbon atoms wherein the alkyl moiety is as defined above, such as methylsulfinyl, ethylsulfinyl, n-propylsulfinyl or i-propylsulfinyl.

The $C_1$-$C_6$ alkylsulfonyl group means an (alkyl)-$SO_2$— group having from 1 to 6 carbon atoms wherein the alkyl moiety is as defined above, such as methylsulfonyl, ethylsulfonyl, n-propylsulfonyl or isopropylsulfonyl.

The $C_1$-$C_7$ acyl group means a formyl group or an (alkyl)-C(=O)— group having from 1 to 6 carbon atoms wherein the alkyl moiety is as defined above, such as acetyl or propionyl.

The $C_2$-$C_7$ alkoxycarbonyl group means an (alkyl)-O—C(=O)— group having from 1 to 6 carbon atoms wherein the alkyl moiety is as defined above, such as methoxycarbonyl, ethoxycarbonyl, n-propoxycarbonyl or isopropoxycarbonyl.

The $C_1$-$C_4$ haloalkylcarbonyl group means a (haloalkyl)-C(=O)— group having from 1 to 4 carbon atoms wherein the haloalkyl moiety is as defined above, such as chloroacetyl, trifluoroacetyl, pentafluoropropionyl or difluoromethylthio.

The $C_1$-$C_6$ monoalkylamino group means an amino group mono-substituted by an alkyl group wherein the alkyl moiety is as defined above, such as methylamino, ethylamino or n-propylamino.

The $C_2$-$C_{12}$ dialkylamino group means an amino group di-substituted by alkyl groups wherein the alkyl moieties are as defined above, such as dimethylamino, diethylamino or N-ethyl-N-methylamino.

The aryl group means an aromatic hydrocarbon group, such as phenyl or naphthyl.

The arylalkyl group means an (aryl)-(alkyl) group wherein the aryl and alkyl moieties are as defined above, such as benzyl, phenethyl or naphthylmethyl.

The heteroaryl group means an aromatic heterocyclic group, such as thienyl, pyridyl or benzothiazolyl.

The heteroarylalkyl group means a (heteroaryl)-(alkyl) group wherein the heteroaryl and alkyl moieties are as defined above, such as thienylmethyl or pyridylmethyl.

Preferred compounds of the above formula [I] are compounds wherein R is a 2,2,2-trifluoroethyl group, and n is 0 or 1.

More preferred compounds are compounds wherein R is a 2,2,2-trifluoroethyl group, $B_2$ is a halogen atom, $B_4$ is an alkyl group or a haloalkyl group, and n is 0 or 1.

Now, specific examples of the compounds of the present invention represented by the formula [I] will be given in Tables 1 to 6. However, the compounds of the present invention are not limited to these compounds. Further, these compounds include compounds having an optical isomer. The compound numbers will be referred to in the subsequent description.

The symbols in the Tables in this specification denote the following respective corresponding groups.

| | |
|---|---|
| Me: methyl, | Et: ethyl, |
| Pr: n-propyl, | Pr-i: isopropyl, |
| Pr-c: cyclopropyl, | Bu: n-butyl, |
| Bu-i: isobutyl, | Bu-s: sec-butyl, |
| Bu-t: tert-butyl, | Bu-c: cyclobutyl, |
| Pen: n-pentyl, | Pen-i: isopentyl, |
| Pen-c: cyclopentyl, | Hex-c: cyclohexyl, |
| Ph: phenyl, | Py: pyridyl. |

For example, Ph-4-Cl means 4-chlorophenyl, and 3-Py-6-Cl means 6-chloro-3-pyridyl.

TABLE 1

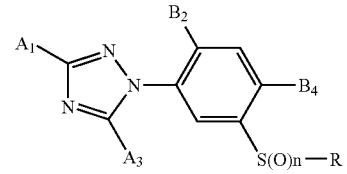

| Comp No. | $A_1$ | $A_3$ | $B_2$ | $B_4$ | R | n |
|---|---|---|---|---|---|---|
| 1 | $CF_3$ | $NH_2$ | F | Me | $CH_2CF_3$ | 0 |
| 2 | $CF_3$ | $NH_2$ | F | Me | $CH_2CF_3$ | 1 |
| 3 | $CF_3$ | $NH_2$ | F | Me | $CH_2$Pr-c | 0 |
| 4 | $CF_3$ | $NH_2$ | F | Me | $CH_2$Pr-c | 1 |
| 5 | $CF_3$ | $NHCOCF_3$ | F | Me | $CH_2CF_3$ | 0 |
| 6 | $CF_3$ | $NHCOCF_3$ | F | Me | $CH_2CF_3$ | 1 |
| 7 | $CF_3$ | $NH_2$ | Cl | Me | $CH_2CF_3$ | 0 |
| 8 | $CF_3$ | $NH_2$ | Cl | Me | $CH_2CF_3$ | 1 |
| 9 | $CF_3$ | $NH_2$ | Me | Cl | $CH_2CF_3$ | 0 |
| 10 | $CF_3$ | $NH_2$ | Me | Cl | $CH_2CF_3$ | 1 |
| 11 | $NO_2$ | H | H | $CHF_2$ | $CH_2CF_3$ | 0 |
| 12 | $NO_2$ | H | H | $CHF_2$ | $CH_2CF_3$ | 1 |
| 13 | $NO_2$ | H | H | CN | $CH_2CF_3$ | 0 |
| 14 | $NO_2$ | H | H | CN | $CH_2CF_3$ | 1 |
| 15 | SMe | $NH_2$ | F | Me | $CH_2CF_3$ | 0 |
| 16 | SMe | $NH_2$ | F | Me | $CH_2CF_3$ | 1 |
| 17 | SOMe | $NH_2$ | F | Me | $CH_2CF_3$ | 0 |
| 18 | SOMe | $NH_2$ | F | Me | $CH_2CF_3$ | 1 |
| 19 | $SO_2$Me | $NH_2$ | F | Me | $CH_2CF_3$ | 0 |
| 20 | $SO_2$Me | $NH_2$ | F | Me | $CH_2CF_3$ | 1 |
| 21 | SEt | $NH_2$ | F | Me | $CH_2CF_3$ | 0 |
| 22 | SEt | $NH_2$ | F | Me | $CH_2CF_3$ | 1 |
| 23 | SOEt | $NH_2$ | F | Me | $CH_2CF_3$ | 0 |
| 24 | SOEt | $NH_2$ | F | Me | $CH_2CF_3$ | 1 |
| 25 | $SO_2$Et | $NH_2$ | F | Me | $CH_2CF_3$ | 0 |
| 26 | $SO_2$Et | $NH_2$ | F | Me | $CH_2CF_3$ | 1 |
| 27 | $SCHF_2$ | $NH_2$ | F | Me | $CH_2CF_3$ | 0 |
| 28 | $SCHF_2$ | $NH_2$ | F | Me | $CH_2CF_3$ | 1 |
| 29 | $S(O)CHF_2$ | $NH_2$ | F | Me | $CH_2CF_3$ | 0 |
| 30 | $S(O)CHF_2$ | $NH_2$ | F | Me | $CH_2CF_3$ | 1 |
| 31 | $SCF_3$ | $NH_2$ | F | Me | $CH_2CF_3$ | 0 |
| 32 | $SCF_3$ | $NH_2$ | F | Me | $CH_2CF_3$ | 1 |
| 33 | CN | H | F | Me | $CH_2CF_3$ | 0 |

Comp No.: Compound No.

TABLE 2

| Comp No. | $A_1$ | $A_3$ | $B_2$ | $B_4$ | R | n |
|---|---|---|---|---|---|---|
| 34 | CN | H | F | Me | $CH_2CF_3$ | 1 |
| 35 | CN | $NH_2$ | F | Me | $CH_2CF_3$ | 0 |

TABLE 2-continued

| Comp No. | $A_1$ | $A_3$ | $B_2$ | $B_4$ | R | n |
|---|---|---|---|---|---|---|
| 36 | CN | $NH_2$ | F | Me | $CH_2CF_3$ | 1 |
| 37 | $CF_3$ | NHMe | H | Me | $CH_2CF_3$ | 0 |
| 38 | $CF_3$ | NHMe | H | Me | $CH_2CF_3$ | 1 |
| 39 | $CF_3$ | NHMe | F | Me | $CH_2CF_3$ | 0 |
| 40 | $CF_3$ | NHMe | F | Me | $CH_2CF_3$ | 1 |
| 41 | $CF_3$ | $N(Me)_2$ | H | Me | $CH_2CF_3$ | 0 |
| 42 | $CF_3$ | $N(Me)_2$ | H | Me | $CH_2CF_3$ | 1 |
| 43 | $CF_3$ | $N(Me)_2$ | F | Me | $CH_2CF_3$ | 0 |
| 44 | $CF_3$ | $N(Me)_2$ | F | Me | $CH_2CF_3$ | 1 |
| 45 | $CF_3$ | $NHSO_2Me$ | H | Me | $CH_2CF_3$ | 0 |
| 46 | $CF_3$ | $NHSO_2Me$ | H | Me | $CH_2CF_3$ | 1 |
| 47 | $CF_3$ | $NHSO_2Me$ | F | Me | $CH_2CF_3$ | 0 |
| 48 | $CF_3$ | $NHSO_2Me$ | F | Me | $CH_2CF_3$ | 1 |
| 49 | Et | $NH_2$ | F | Me | $CH_2CF_3$ | 0 |
| 50 | Et | $NH_2$ | F | Me | $CH_2CF_3$ | 1 |
| 51 | Cl | $NH_2$ | F | Me | $CH_2CF_3$ | 0 |
| 52 | Cl | $NH_2$ | F | Me | $CH_2CF_3$ | 1 |
| 53 | Br | $NH_2$ | F | Me | $CH_2CF_3$ | 0 |
| 54 | Br | $NH_2$ | F | Me | $CH_2CF_3$ | 1 |
| 55 | $CF_3$ | $NH_2$ | Me | Me | $CH_2CF_3$ | 0 |
| 56 | $CF_3$ | $NH_2$ | Me | Me | $CH_2CF_3$ | 1 |
| 57 | $CF_3$ |  | F | Me | $CH_2CF_3$ | 0 |
| 58 | $CF_3$ |  | F | Me | $CH_2CF_3$ | 1 |
| 59 | $CF_3$ | NHEt | F | Me | $CH_2CF_3$ | 0 |
| 60 | $CF_3$ | NHEt | F | Me | $CH_2CF_3$ | 1 |
| 61 | $CF_3$ | NHPr | F | Me | $CH_2CF_3$ | 0 |
| 62 | $CF_3$ | NHPr | F | Me | $CH_2CF_3$ | 1 |
| 63 | $CF_3$ | $NHCH_2CH=CH_2$ | F | Me | $CH_2CF_3$ | 0 |
| 64 | $CF_3$ | $NHCH_2CH=CH_2$ | F | Me | $CH_2CF_3$ | 1 |
| 65 | $CF_3$ | $NHCH_2C\equiv CH$ | F | Me | $CH_2CF_3$ | 0 |
| 66 | $CF_3$ | $NHCH_2C\equiv CH$ | F | Me | $CH_2CF_3$ | 1 |
| 67 | $CF_3$ | $NHCH_2Ph$-4-Cl | F | Me | $CH_2CF_3$ | 0 |
| 68 | $CF_3$ | $NHCH_2Ph$-4-Cl | F | Me | $CH_2CF_3$ | 1 |

TABLE 3

| Comp No. | $A_1$ | $A_3$ | $B_2$ | $B_4$ | R | n |
|---|---|---|---|---|---|---|
| 69 | $CF_3$ | $NHCH_2$-3-Py-6-Cl | F | Me | $CH_2CF_3$ | 0 |
| 70 | $CF_3$ | $NHCH_2$-3-Py-6-Cl | F | Me | $CH_2CF_3$ | 1 |
| 71 | $CF_3$ | NH—Ph-2,6-$Cl_2$-4-$CF_3$ | F | Me | $CH_2CF_3$ | 0 |
| 72 | $CF_3$ | NH—Ph-2,6-$Cl_2$-4-$CF_3$ | F | Me | $CH_2CF_3$ | 1 |
| 73 | $CF_3$ | NH-2-Py-3-Cl-5-$CF_3$ | F | Me | $CH_2CF_3$ | 0 |
| 74 | $CF_3$ | NH-2-Py-3-Cl-5-$CF_3$ | F | Me | $CH_2CF_3$ | 1 |
| 75 | $CF_3$ | NHCOMe | F | Me | $CH_2CF_3$ | 0 |
| 76 | $CF_3$ | NHCOMe | F | Me | $CH_2CF_3$ | 1 |
| 77 | $CF_3$ | $NHCOCH_2OMe$ | F | Me | $CH_2CF_3$ | 0 |
| 78 | $CF_3$ | $NHCOCH_2OMe$ | F | Me | $CH_2CF_3$ | 1 |
| 79 | $CF_3$ | NHCOOMe | F | Me | $CH_2CF_3$ | 0 |
| 80 | $CF_3$ | NHCOOMe | F | Me | $CH_2CF_3$ | 1 |
| 81 | $CF_3$ | $NHCONH_2$ | F | Me | $CH_2CF_3$ | 0 |
| 82 | $CF_3$ | $NHCONH_2$ | F | Me | $CH_2CF_3$ | 1 |
| 83 | $CF_3$ | $NHCONMe_2$ | F | Me | $CH_2CF_3$ | 0 |
| 84 | $CF_3$ | $NHCONMe_2$ | F | Me | $CH_2CF_3$ | 1 |
| 85 | $CF_3$ | $NHSO_2NMe_2$ | F | Me | $CH_2CF_3$ | 0 |
| 86 | $CF_3$ | $NHSO_2NMe_2$ | F | Me | $CH_2CF_3$ | 1 |
| 87 | $CF_3$ | $NHSO_2CF_3$ | F | Me | $CH_2CF_3$ | 0 |
| 88 | $CF_3$ | $NHSO_2CF_3$ | F | Me | $CH_2CF_3$ | 1 |
| 89 | $CF_3$ | N=CH—Ph-4-OH-3-OMe | F | Me | $CH_2CF_3$ | 0 |
| 90 | $CF_3$ | N=CH—Ph-4-OH-3-OMe | F | Me | $CH_2CF_3$ | 1 |
| 91 | $CF_3$ | $N=CMe_2$ | F | Me | $CH_2CF_3$ | 0 |
| 92 | $CF_3$ | $N=CMe_2$ | F | Me | $CH_2CF_3$ | 1 |
| 93 | $CF_3$ | $N=C(NH_2)_2$ | F | Me | $CH_2CF_3$ | 0 |
| 94 | $CF_3$ | $N=C(NH_2)_2$ | F | Me | $CH_2CF_3$ | 1 |
| 95 | $CF_3$ | 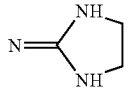 | F | Me | $CH_2CF_3$ | 0 |
| 96 | $CF_3$ | 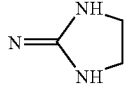 | F | Me | $CH_2CF_3$ | 1 |
| 97 | $CF_3$ | NHMe | Cl | Me | $CH_2CF_3$ | 0 |
| 98 | $CF_3$ | NHMe | Cl | Me | $CH_2CF_3$ | 1 |
| 99 | $SCF_3$ | $NHCOCF_3$ | F | Me | $CH_2CF_3$ | 0 |
| 100 | $SCF_3$ | $NHCOCF_3$ | F | Me | $CH_2CF_3$ | 1 |
| 101 | $SC_2F_5$ | NHMe | F | Me | $CH_2CF_3$ | 0 |
| 102 | $SC_2F_5$ | NHMe | F | Me | $CH_2CF_3$ | 1 |
| 103 | $C(Me)_2CN$ | $NH_2$ | F | Me | $CH_2CF_3$ | 0 |
| 104 | $C(Me)_2CN$ | $NH_2$ | F | Me | $CH_2CF_3$ | 1 |

TABLE 4

| Comp No. | $A_1$ | $A_3$ | $B_2$ | $B_4$ | R | n |
|---|---|---|---|---|---|---|
| 105 | Me | $NH_2$ | F | Me | $CH_2CF_3$ | 0 |
| 106 | Me | $NH_2$ | F | Me | $CH_2CF_3$ | 1 |
| 106 | $CH_2$Bu-t | $NH_2$ | F | Me | $CH_2CF_3$ | 1 |
| 107 | $CH_2$Bu-t | $NH_2$ | F | Me | $CH_2CF_3$ | 1 |
| 108 | $CF_3$ | NHCOMe | Cl | Me | $CH_2CF_3$ | 0 |
| 109 | $CF_3$ | NHCOMe | Cl | Me | $CH_2CF_3$ | 1 |
| 110 | Pr-i | $NH_2$ | F | Me | $CH_2CF_3$ | 0 |
| 111 | Pr-i | $NH_2$ | F | Me | $CH_2CF_3$ | 1 |
| 112 | Bu-t | NHCOMe | F | Me | $CH_2CF_3$ | 0 |
| 113 | Bu-t | NHCOMe | F | Me | $CH_2CF_3$ | 1 |
| 114 | Bu-t | NHMe | F | Me | $CH_2CF_3$ | 0 |
| 115 | Bu-t | NHMe | F | Me | $CH_2CF_3$ | 1 |
| 116 | Et | $NH_2$ | F | Me | $CH_2CF_3$ | 0 |
| 117 | Et | $NH_2$ | F | Me | $CH_2CF_3$ | 1 |
| 118 | $C(Me)_2Et$ | $NH_2$ | F | Me | $CH_2CF_3$ | 0 |
| 119 | $C(Me)_2Et$ | $NH_2$ | F | Me | $CH_2CF_3$ | 1 |
| 120 | $CF_3$ | $NH_2$ | H | CN | $CH_2CF_3$ | 0 |
| 121 | $CF_3$ | $NH_2$ | H | CN | $CH_2CF_3$ | 1 |
| 122 | $CF_3$ | $NH_2$ | H | $CHF_2$ | $CH_2CF_3$ | 0 |
| 123 | $CF_3$ | $NH_2$ | H | $CHF_2$ | $CH_2CF_3$ | 1 |
| 124 | $CF_3$ | $NH_2$ | H | Me | $CH_2CF_3$ | 0 |
| 125 | $CF_3$ | $NH_2$ | H | Me | $CH_2CF_3$ | 1 |
| 126 | $CF_3$ | $NH_2$ | H | Cl | $CH_2CF_3$ | 0 |
| 127 | $CF_3$ | $NH_2$ | H | Cl | $CH_2CF_3$ | 1 |
| 128 | $CF_3$ | $N(Et)_2$ | F | Me | $CH_2CF_3$ | 0 |
| 129 | $CF_3$ | $N(Et)_2$ | F | Me | $CH_2CF_3$ | 1 |
| 130 | $SCH_2CF_3$ | $NH_2$ | F | Me | $CH_2CF_3$ | 0 |
| 131 | $SCH_2CF_3$ | $NH_2$ | F | Me | $CH_2CF_3$ | 1 |
| 132 | $S(O)CH_2CF_3$ | $NH_2$ | F | Me | $CH_2CF_3$ | 0 |
| 133 | $S(O)CH_2CF_3$ | $NH_2$ | F | Me | $CH_2CF_3$ | 1 |
| 134 | SPr | $NH_2$ | F | Me | $CH_2CF_3$ | 0 |
| 135 | SPr | $NH_2$ | F | Me | $CH_2CF_3$ | 1 |
| 136 | S(O)Pr | $NH_2$ | F | Me | $CH_2CF_3$ | 0 |
| 137 | S(O)Pr | $NH_2$ | F | Me | $CH_2CF_3$ | 1 |
| 138 | $S(O)_2$Pr | $NH_2$ | F | Me | $CH_2CF_3$ | 0 |
| 139 | $S(O)_2$Pr | $NH_2$ | F | Me | $CH_2CF_3$ | 1 |
| 140 | $SCH_2CN$ | $NH_2$ | F | Me | $CH_2CF_3$ | 0 |
| 141 | $SCH_2CN$ | $NH_2$ | F | Me | $CH_2CF_3$ | 1 |
| 142 | $S(O)CH_2CN$ | $NH_2$ | F | Me | $CH_2CF_3$ | 0 |
| 143 | $S(O)CH_2CN$ | $NH_2$ | F | Me | $CH_2CF_3$ | 1 |
| 144 | Bu-t | $NH_2$ | F | Me | $CH_2CF_3$ | 0 |

TABLE 5

| Comp No. | A₁ | A₃ | B₂ | B₄ | R | n |
|---|---|---|---|---|---|---|
| 145 | Bu-t | $NH_2$ | F | Me | $CH_2CF_3$ | 1 |
| 146 | $CF_3$ | NHMe | Me | Me | $CH_2CF_3$ | 0 |
| 147 | $CF_3$ | NHMe | Me | Me | $CH_2CF_3$ | 1 |
| 148 | $SCH_2C\equiv CH$ | $NH_2$ | F | Me | $CH_2CF_3$ | 0 |
| 149 | $SCH_2C\equiv CH$ | $NH_2$ | F | Me | $CH_2CF_3$ | 1 |
| 150 | $S(O)CH_2C\equiv CH$ | $NH_2$ | F | Me | $CH_2CF_3$ | 0 |
| 151 | $S(O)CH_2C\equiv CH$ | $NH_2$ | F | Me | $CH_2CF_3$ | 1 |
| 152 | $CF_3$ | $NHCOCF_3$ | H | Me | $CH_2CF_3$ | 0 |
| 153 | $CF_3$ | $NHCOCF_3$ | H | Me | $CH_2CF_3$ | 1 |
| 154 | $SCH_2CF_3$ | NHCOMe | F | Me | $CH_2CF_3$ | 0 |
| 155 | $SCH_2CF_3$ | NHCOMe | F | Me | $CH_2CF_3$ | 1 |
| 156 | $S(O)CH_2CF_3$ | NHCOMe | F | Me | $CH_2CF_3$ | 0 |
| 157 | $S(O)CH_2CF_3$ | NHCOMe | F | Me | $CH_2CF_3$ | 1 |
| 158 | $SCH_2CF_3$ | N(Me)COMe | F | Me | $CH_2CF_3$ | 0 |
| 159 | $SCH_2CF_3$ | N(Me)COMe | F | Me | $CH_2CF_3$ | 1 |
| 160 | $SCH_2CF_3$ | NHMe | F | Me | $CH_2CF_3$ | 0 |
| 161 | $SCH_2CF_3$ | NHMe | F | Me | $CH_2CF_3$ | 1 |
| 162 | $CF_3$ | $NHNH_2$ | F | Me | $CH_2CF_3$ | 0 |
| 163 | $CF_3$ | $NHNH_2$ | F | Me | $CH_2CF_3$ | 1 |
| 164 | $CF_3$ | $NHCH_2CN$ | F | Me | $CH_2CF_3$ | 0 |
| 165 | $CF_3$ | $NHCH_2CN$ | F | Me | $CH_2CF_3$ | 1 |
| 166 | $CF_3$ | NHPr-i | F | Me | $CH_2CF_3$ | 0 |
| 167 | $CF_3$ | NHPr-i | F | Me | $CH_2CF_3$ | 1 |
| 168 | $CF_3$ | NHCONHMe | F | Me | $CH_2CF_3$ | 0 |
| 169 | $CF_3$ | NHCONHMe | F | Me | $CH_2CF_3$ | 1 |
| 170 | $CF_3$ | $N(Me)NH_2$ | F | Me | $CH_2CF_3$ | 0 |
| 171 | $CF_3$ | $N(Me)NH_2$ | F | Me | $CH_2CF_3$ | 1 |
| 172 | $SC_3F_7$ | $NH_2$ | F | Me | $CH_2CF_3$ | 0 |
| 173 | $SC_3F_7$ | $NH_2$ | F | Me | $CH_2CF_3$ | 1 |
| 174 | $C_3F_7$ | $NH_2$ | F | Me | $CH_2CF_3$ | 0 |
| 175 | $C_3F_7$ | $NH_2$ | F | Me | $CH_2CF_3$ | 1 |
| 176 | $SC_2F_5$ | $NH_2$ | F | Me | $CH_2CF_3$ | 0 |
| 177 | $SC_2F_5$ | $NH_2$ | F | Me | $CH_2CF_3$ | 1 |
| 178 | 1-methylcyclopropyl | $NH_2$ | F | Me | $CH_2CF_3$ | 0 |
| 179 | 1-methylcyclopropyl | $NH_2$ | F | Me | $CH_2CF_3$ | 1 |
| 180 | 1-methylcyclohexyl | $NH_2$ | F | Me | $CH_2CF_3$ | 0 |

TABLE 6

| Comp No. | A₁ | A₃ | B₂ | B₄ | R | n |
|---|---|---|---|---|---|---|
| 181 | 1-methylcyclohexyl | $NH_2$ | F | Me | $CH_2CF_3$ | 1 |
| 182 | $CH(CF_3)_2$ | $NH_2$ | F | Me | $CH_2CF_3$ | 0 |
| 183 | $CH(CF_3)_2$ | $NH_2$ | F | Me | $CH_2CF_3$ | 1 |
| 184 | $SCH_2CF_3$ | $NHCH_2C\equiv CH$ | F | Me | $CH_2CF_3$ | 0 |
| 185 | $SCH_2CF_3$ | $NHCH_2C\equiv CH$ | F | Me | $CH_2CF_3$ | 1 |
| 186 | $CF_3$ | NHCOEt | F | Me | $CH_2CF_3$ | 0 |
| 187 | $CF_3$ | NHCOEt | F | Me | $CH_2CF_3$ | 1 |
| 189 | $CF_3$ | $NHCOCH_2Cl$ | F | Me | $CH_2CF_3$ | 0 |
| 190 | $CF_3$ | $NHCOCH_2Cl$ | F | Me | $CH_2CF_3$ | 1 |
| 191 | $CF_3$ | $NHCOCF_2Cl$ | F | Me | $CH_2CF_3$ | 0 |
| 192 | $CF_3$ | $NHCOCF_2Cl$ | F | Me | $CH_2CF_3$ | 1 |
| 193 | $SC_2F_5$ | $NHCH_2C\equiv CH$ | F | Me | $CH_2CF_3$ | 0 |
| 194 | $SC_2F_5$ | $NHCH_2C\equiv CH$ | F | Me | $CH_2CF_3$ | 1 |
| 195 | S-CH₂-(2,2-difluorocyclopropyl) | $NH_2$ | F | Me | $CH_2CF_3$ | 0 |
| 196 | SO-CH₂-(2,2-difluorocyclopropyl) | $NH_2$ | F | Me | $CH_2CF_3$ | 0 |
| 197 | SO-CH₂-(2,2-difluorocyclopropyl) | $NH_2$ | F | Me | $CH_2CF_3$ | 1 |
| 198 | SO₂-CH₂-(2,2-difluorocyclopropyl) | $NH_2$ | F | Me | $CH_2CF_3$ | 1 |
| 199 | $CF_3$ | $NHCOCHF_2$ | F | Me | $CH_2CF_3$ | 0 |
| 200 | $CF_3$ | $NHCOCHF_2$ | F | Me | $CH_2CF_3$ | 1 |
| 201 | $CF_3$ | NHCONHPr-i | F | Me | $CH_2CF_3$ | 0 |
| 202 | $CF_3$ | NHCONHPr-i | F | Me | $CH_2CF_3$ | 1 |
| 203 | $CF_3$ | COOMe | F | Me | $CH_2CF_3$ | 0 |
| 204 | $CF_3$ | COOMe | F | Me | $CH_2CF_3$ | 1 |
| 205 | $CF_3$ | COOEt | F | Me | $CH_2CF_3$ | 0 |
| 206 | $CF_3$ | COOEt | F | Me | $CH_2CF_3$ | 1 |
| 207 | $CF_3$ | $CONH_2$ | F | Me | $CH_2CF_3$ | 0 |
| 208 | $CF_3$ | $CONH_2$ | F | Me | $CH_2CF_3$ | 1 |
| 209 | $CF_3$ | CN | F | Me | $CH_2CF_3$ | 0 |
| 210 | $CF_3$ | CN | F | Me | $CH_2CF_3$ | 1 |
| 211 | $CF_3$ | $N(Me)COCF_3$ | F | Me | $CH_2CF_3$ | 0 |
| 212 | $CF_3$ | $N(Me)COCF_3$ | F | Me | $CH_2CF_3$ | 1 |

The compounds of the present invention represented by the formula [I] can be produced in accordance with the following production processes. However, their production is not restricted to these processes.

<Production Process 1>

A compound of the present invention of the formula [I-1] can be produced by a process exemplified by the following scheme:

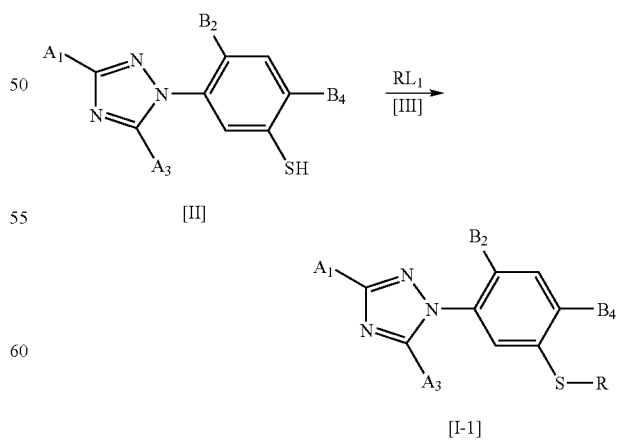

wherein $L_1$ is a halogen atom, an alkylsulfonyloxy group, a phenylsulfonyloxy group or $SO_2M$, M is an alkali metal or an alkaline earth metal, the alkali metal is preferably sodium or potassium, and $A_1$, $A_3$, $B_2$, $B_4$ and R are as defined above.

That is, a 3-triazolylphenyl sulfide derivative of the formula [I-1] which is a compound of the present invention can be produced by reacting a compound of the formula [II] with a compound of the formula [III] in a solvent in the presence of a base or in the presence of a radical initiator.

The amount of the compound of the formula [III] to be used may suitably be selected from a range of from 1 to 5 mols per 1 mol of the compound of the formula [I], and it is preferably from 1.2 to 2.0 mols.

The solvent to be used in this reaction may, for example, be an ether such as diethyl ether, tetrahydrofuran or dioxane, an aromatic hydrocarbon such as benzene, toluene, xylene or chlorobenzene, a halogenated hydrocarbon such as dichloromethane, chloroform or dichloroethane, an aprotic polar solvent such as acetonitrile, N,N-dimethylformamide, N,N-dimethylacetamide, N-methyl-2-pyrrolidone, dimethyl sulfoxide or sulfolane, an alcohol such as methanol, ethanol or isopropyl alcohol, a nitrile such as acetonitrile or propionitrile, an ester such as ethyl acetate or ethyl propionate, an aliphatic hydrocarbon such as pentane, hexane, cyclohexane or heptane, a pyridine such as pyridine or picoline, or water, or a solvent mixture thereof.

The base to be used in this reaction may, for example, be an inorganic base such as a hydroxide of an alkali metal such as sodium hydroxide or potassium hydroxide, a hydroxide of an alkaline earth metal such as calcium hydroxide or magnesium hydroxide, a carbonate of an alkali metal such as sodium carbonate or potassium carbonate, or an alkali metal bicarbonate such as sodium hydrogen carbonate or potassium hydrogen carbonate, a metal hydride such as sodium hydride or potassium hydride, a metal salt of an alcohol such as sodium methoxide, sodium ethoxide or potassium tert-butoxide, or an organic base such as triethylamine, N,N-dimethylaniline, pyridine, 4-N,N-dimethylaminopyridine or 1,8-diazabicyclo[5.4.0]-7-undecene.

The amount of the base to be used may suitably be selected from a range of from 0 to 5 mols per 1 mol of the compound of the formula [II], and it is preferably from 0 to 1.2 mols.

The radical initiator to be used in this reaction may, for example, be sulfurous acid, a sulfite salt or a sulfite adduct such as Rongalit (sodium formaldehyde sulfoxylate). The base and the radical initiator may be used together.

In a case where the radical initiator is used, its amount may suitably be selected from a range of from 0.01 to 5 mols per 1 mol of the compound [II], and it is preferably from 0.05 to 1.2 mols.

The reaction temperature may be optionally selected from a range of from −30° C. to the reflux temperature of the reaction system, and it is preferably within a range of from 0° C. to 150° C. The reaction time varies depending upon the reaction temperature, the reaction substrate, the reaction amount, etc., and it is usually from 10 minutes to 20 hours.

<Production Process 2>

A compound of the present invention of the formula [I-1] can be produced also by using a compound of the formula [IV], which is the oxidative dimer of a compound of the formula [II] used in Production Process 1, as the starting material:

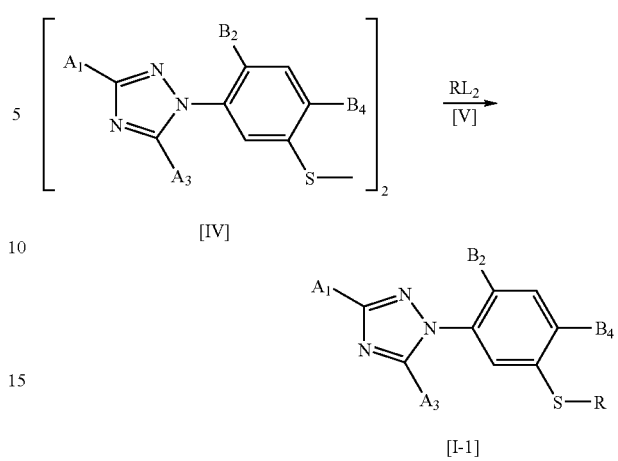

wherein $L_2$ is a halogen atom or a sulfinate salt, and $A_1$, $A_3$, $B_2$, $B_4$ and R are as defined above.

That is, an aimed 3-triazolylphenyl sulfide derivative of the formula [I-1] can be produced by reacting a compound of the formula [IV] with a compound of the formula [V] in a solvent in the presence of a radical initiator.

The amount of the compound of the formula [V] to be used in this reaction may suitably be selected from a range of from 1 to 5 mols per 1 mol of the compound of the formula [IV], and it is preferably from 1.2 to 2.0 mols.

The solvent to be used in this reaction may, for example, be an ether such as diethyl ether, tetrahydrofuran or dioxane, an aromatic hydrocarbon such as benzene, toluene, xylene or chlorobenzene, an aprotic polar solvent such as N,N-dimethylformamide, N,N-dimethylacetamide, N-methyl-2-pyrrolidone, dimethyl sulfoxide or sulfolane, a nitrile such as acetonitrile or propionitrile, an ester such as ethyl acetate or ethyl propionate, an aliphatic hydrocarbon such as pentane, hexane, cyclohexane or heptane, a pyridine such as pyridine or picoline, or water, or a solvent mixture thereof.

The radical initiator may, for example, be sulfurous acid, a sulfite salt or a sulfite adduct such as Rongalit (sodium formaldehyde sulfoxylate).

In a case where the radical initiator is used, its amount may suitably be selected from a range of from 0.01 to 5 mols per 1 mol of the compound [II], and it is preferably from 0.05 to 1.2 mols.

The reaction temperature may be optionally selected from a range of from −30° C. to the reflux temperature of the reaction system, and it is preferably within a range of from 0° C. to 150° C. The reaction time varies depending upon the reaction temperature, the reaction substrate, the reaction amount, etc., and it is usually from 10 minutes to 20 hours.

<Production Process 3>

A compound of the formula [I-2] which is a compound of the present invention can be produced by a process exemplified by the following scheme:

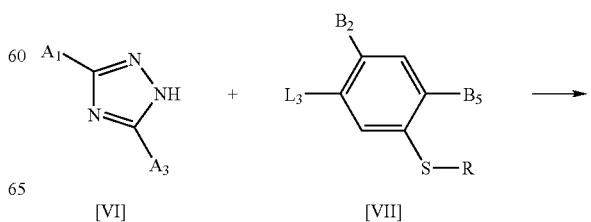

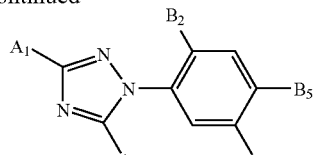

[I-2]

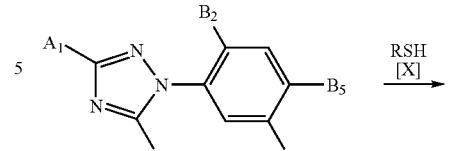

[IX]

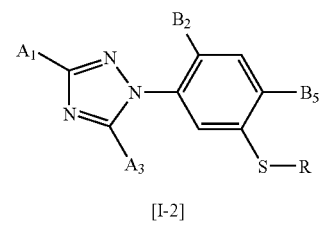

[I-2]

wherein $B_5$ is an electron-withdrawing group, $A_1$, $A_3$, $B_2$ and R are as defined above, $L_3$ is a leaving group such as a halogen atom, an alkylsulfonyloxy group or a phenylsulfonyloxy group, and the electron-withdrawing group is a cyano group, a nitro group or the like.

That is, a compound of the present invention of the formula [I-2] can be produced by reacting a compound of the formula [VI] with a compound of the formula [VII] in a solvent in the presence of a base.

The amount of the compound of the formula [VII] may suitably be selected from a range of from 1 to 5 mols per 1 mol of the compound of the formula [VI], and it is preferably from 1.0 to 1.2 mols.

The solvent to be used in this reaction is not limited so long as it does not inhibit the reaction, and it may, for example, be an aromatic hydrocarbon such as benzene, toluene or xylene, an ether such as diethyl ether, tetrahydrofuran, 1,2-dimethoxyethane or dioxane, a ketone such as acetone or methyl ethyl ketone, a nitrile such as acetonitrile or propionitrile, an aprotic polar solvent such as dimethyl sulfoxide, N,N-dimethylformamide or N,N-dimethylacetamide, an aliphatic hydrocarbon such as pentane, hexane, cyclohexane or heptane or a pyridine such as pyridine or picoline, or a solvent mixture thereof.

The base to be used in this reaction may, for example, be an inorganic base such as a hydroxide of an alkali metal such as sodium hydroxide or potassium hydroxide, a hydroxide of an alkaline earth metal such as calcium hydroxide or magnesium hydroxide, a carbonate of an alkali metal such as sodium carbonate or potassium carbonate, or an alkali metal bicarbonate such as sodium hydrogencarbonate or potassium hydrogencarbonate, a metal hydride such as sodium hydride or potassium hydride, a metal salt of an alcohol such as sodium methoxide, sodium ethoxide or potassium tert-butoxide, or an organic base such as triethylamine, N,N-dimethylaniline, pyridine, 4-N,N-dimethylaminopyridine or 1,8-diazabicyclo[5.4.0]-7-undecene.

The amount of the base to be used may suitably be selected from a range of from 1 to 5 mols per 1 mol of the compound of the formula [II], and it is preferably from 1.1 to 1.2 mols.

The reaction temperature may be optionally selected from a range of from −70° C. to the reflux temperature of the reaction system, and it is preferably within a range of from −20° C. to 150° C. The reaction time varies depending upon the reaction temperature, the reaction substrate, the reaction amount, etc., and it is usually from 10 minutes to 20 hours.

<Production Process 4>

A compound of the formula [I-2] which is a compound of the present invention can be produced also by the following substitution reaction:

wherein $A_1$, $A_3$, $B_2$, $B_5$ and R are as defined above, and $L_4$ is a halogen atom, an alkylsulfonyloxy group, a phenylsulfonyloxy group, an alkylsulfonyl group, a phenylsulfonyl group or a nitro group.

That is, a 3-triazolylphenyl sulfide derivative of the formula [I-2] which is a compound of the present invention can be produced by reacting a compound of the formula [IX] with a compound of the formula [X] in a solvent in the presence of a base or copper(I)oxide.

The solvent to be used in this reaction may, for example, be an ether such as diethyl ether, tetrahydrofuran or dioxane, an aromatic hydrocarbon such as benzene, toluene, xylene or chlorobenzene, an aprotic polar solvent such as N,N-dimethylformamide, N,N-dimethylacetamide, N-methyl-2-pyrrolidone, dimethyl sulfoxide or sulfolane, an alcohol such as methanol, ethanol or methyl cellosolve, an aliphatic hydrocarbon such as pentane, hexane, cyclohexane or heptane, a pyridine such as pyridine or picoline, or water, or a solvent mixture thereof.

The base to be used in this reaction may, for example, be an inorganic base such as a hydroxide of an alkali metal such as sodium hydroxide or potassium hydroxide, a hydroxide of an alkaline earth metal such as calcium hydroxide or magnesium hydroxide, a carbonate of an alkali metal such as sodium carbonate or potassium carbonate, or a bicarbonate of an alkali metal such as sodium hydrogencarbonate or potassium hydrogencarbonate, a metal hydride such as sodium hydride or potassium hydride, a metal salt of an alcohol such as sodium methoxide, sodium ethoxide or potassium tert-butoxide, or an organic base such as triethylamine, N,N-dimethylaniline, pyridine, 4-N,N-dimethylaminopyridine or 1,8-diazabicyclo[5.4.0]-7-undecene.

The amount of the base or copper(I)oxide to be used may suitably be selected from a range of from 1 to 5 mols per 1 mol of the compound of the formula [IX], and it is preferably from 1.0 to 1.2 mols.

The reaction temperature may be optionally selected from a range of from −70° C. to the reflux temperature of the reaction system, and it is preferably within a range of from 0° C. to 150° C. The reaction time varies depending upon the reaction temperature, the reaction substrate, the reaction amount, etc., and it is usually from 10 minutes to 20 hours.

<Production Process 5>

A compound of the formula [I] which is a compound of the present invention can be produced by a process exemplified by the following scheme:

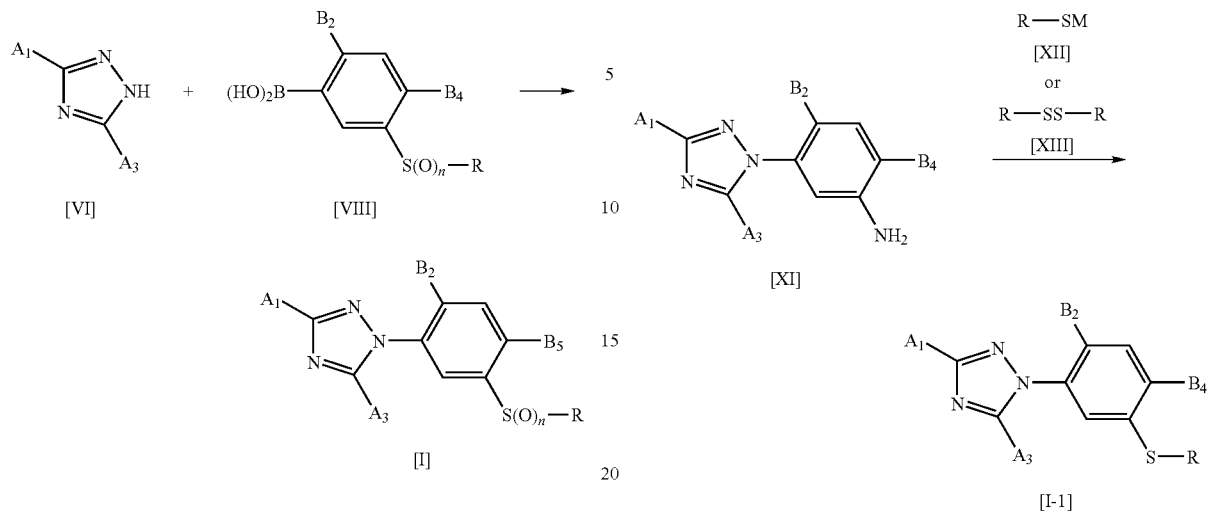

wherein $A_1$, $A_3$, $B_2$, $B_4$, R and n are as defined above.

That is, a compound of the present invention represented by the formula [I] can be produced by reacting a compound of the formula [VI], a compound of the formula [VIII] and an anhydrous copper salt in a solvent in the presence of an organic base.

The amount of the compound of the formula [VIII] to be used may suitably be selected from a range of from 1 to 5 mols per 1 mol of the compound of the formula [VI], and it is preferably from 1.0 to 2.0 mols.

The solvent to be used in this reaction is not limited so long as it does not inhibit the reaction, and it may, for example, be a halogenated alkane such as chloroform or dichloromethane, an aromatic hydrocarbon such as benzene, toluene or xylene, an ether such as diethyl ether, tetrahydrofuran, 1,2-dimethoxyethane or dioxane, a ketone such as acetone or methyl ethyl ketone, a nitrile such as acetonitrile or propionitrile, an aprotic polar solvent such as N,N-dimethylformamide or N,N-dimethylacetamide, an aliphatic hydrocarbon such as pentane, hexane, cyclohexane or heptane, or a pyridine such as pyridine or picoline, or a solvent mixture thereof.

The anhydrous copper salt to be used in this reaction may, for example, be anhydrous copper acetate. The amount of the anhydrous copper salt to be used may suitably be selected from a range of from 1 to 5 mols per 1 mol of the compound of the formula [VI], and it is preferably from 1.2 to 2.2 mols.

The organic base to be used in this reaction may, for example, be triethylamine, N,N-dimethylaniline, pyridine, 4-N,N-dimethylaminopyridine or 1,8-diazabicyclo[5.4.0]-7-undecene.

The amount of the organic base to be used may suitably be selected from a range of from 1 to 5 mols per 1 mol of the compound of the formula [VI], and it is preferably from 1.2 to 4.4 mols.

The reaction temperature may be optionally selected from a range of from 0° C. to the reflux temperature of the reaction system, and it is preferably within a range of from 10° C. to 30° C.

The reaction time varies depending upon the reaction temperature, the reaction substrate, the reaction amount, etc., and it is usually from 8 to 48 hours.

<Production Process 6>

A compound of the formula [I-1] which is a compound of the present invention can be produced also by a process exemplified by the following scheme:

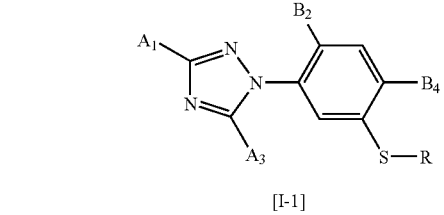

wherein $A_1$, $A_3$, $B_2$, $B_4$, R and M are as defined above.

That is, an aimed 3-triazolylphenyl sulfide derivative of the formula [I-1] can be produced by converting a compound of the formula [XI] into a diazonium salt in a solvent by means of a conventional method (a method by using a mineral acid (such as hydrochloric acid or sulfuric acid) and a nitrite salt or an alkyl nitrite) and reacting the diazonium salt with a mercaptan salt of the formula [XII] or a disulfide of the formula [XIII].

The amount of the compound of the formula [XII] or the compound of the formula [XIII] to be used in this reaction may suitably be selected from a range of from 1 to 5 mols per 1 mol of the compound of the formula [XI], and it is preferably from 1.0 to 2.0 mols.

The solvent to be used in this reaction may, for example, be an ether such as diethyl ether, tetrahydrofuran or dioxane, an aromatic hydrocarbon such as benzene, toluene, xylene or chlorobenzene, a halogenated hydrocarbon such as dichloromethane, chloroform or dichloroethane, an aprotic polar solvent such as acetonitrile, N,N-dimethylformamide, N,N-dimethylacetamide, N-methyl-2-pyrrolidone, dimethyl sulfoxide or sulfolane, an alcohol such as methanol, ethanol or isopropyl alcohol, a nitrile such as acetonitrile or propionitrile, an ester such as ethyl acetate or ethyl propionate, an aliphatic hydrocarbon such as pentane, hexane, cyclohexane or heptane, a pyridine such as pyridine or picoline, or water, or a solvent mixture thereof.

The reaction temperature may be optionally selected from a range of from −30° C. to the reflux temperature of the reaction system, and it is preferably within a range of from −10° C. to 100° C.

The reaction time varies depending upon the reaction temperature, the reaction substrate, the reaction amount, etc., and it is usually from 10 minutes to 20 hours.

<Production Process 7>

A compound of the formula [I] which is a compound of the present invention can be produced also by a process exemplified by the following scheme:

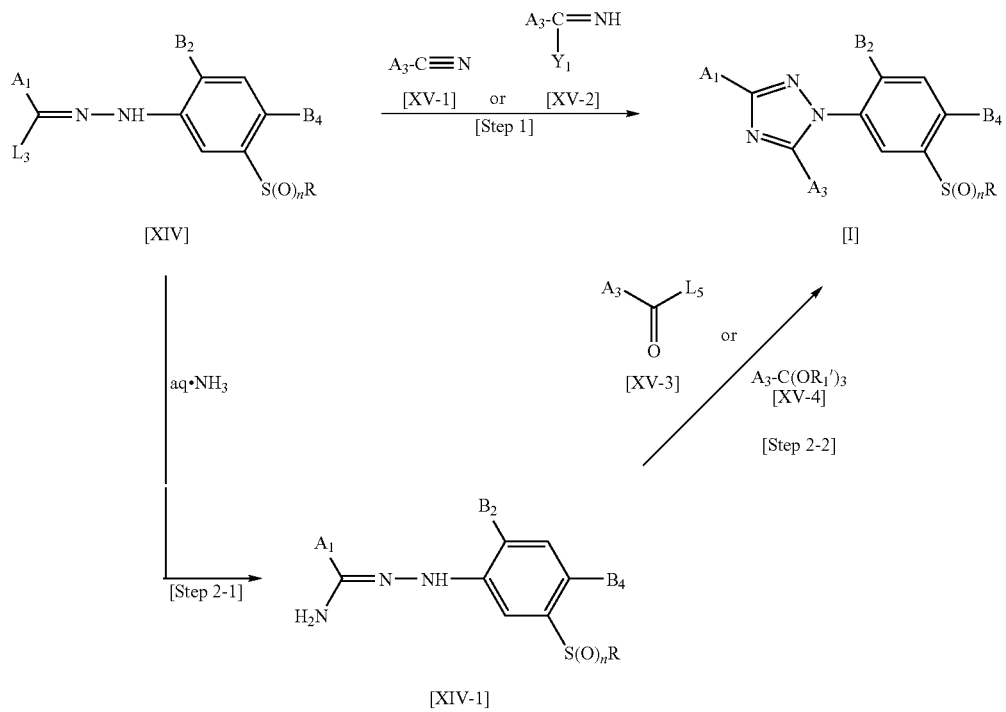

wherein $L_3$, $A_1$, $A_3$, $B_2$, $B_4$, R and n are as defined above, $Y_1$ is an alkoxy group or an alkylthio group, $L_5$ is a leaving group such as a halogen atom, an acyloxy group, an alkylsulfonyloxy group or a phenylsulfonyloxy group, and $R_1'$ is an alkyl group.

[Step 1]

That is, a compound of the present invention of the formula [I] can be produced by reacting a compound of the formula [XIV] with a compound of the formula [XV-1] or [XV-2] in a solvent in the presence of a base.

The amount of the compound of the formula [XV-1] or [XV-2] to be used in this reaction is within a range of from 1 mol to large excess per 1 mol of the compound of the formula [XIV], and it is preferably from 1.2 to 2.0 mols.

The solvent to be used in this reaction may, for example, be an ether such as diethyl ether, tetrahydrofuran or dioxane, an aromatic hydrocarbon such as benzene, toluene, xylene or chlorobenzene, a halogenated hydrocarbon such as dichloromethane, chloroform or dichloroethane, an aprotic polar solvent such as acetonitrile, N,N-dimethylformamide, N,N-dimethylacetamide, N-methyl-2-pyrrolidone, dimethyl sulfoxide or sulfolane, an alcohol such as methanol, ethanol or isopropyl alcohol, a nitrile such as acetonitrile or propionitrile, an ester such as ethyl acetate or ethyl propionate, an aliphatic hydrocarbon such as pentane, hexane, cyclohexane or heptane, a pyridine such as pyridine or picoline, or water, or a solvent mixture thereof.

The base to be used in this reaction may, for example, be an inorganic base such as a hydroxide of an alkali metal such as sodium hydroxide or potassium hydroxide, a hydroxide of an alkaline earth metal such as calcium hydroxide or magnesium hydroxide, a carbonate of an alkali metal such as sodium carbonate or potassium carbonate, or a bicarbonate of an alkali metal such as sodium hydrogencarbonate or potassium hydrogencarbonate, a metal hydride such as sodium hydride or potassium hydride, a metal salt of an alcohol such as sodium methoxide, sodium ethoxide or potassium tert-butoxide, or an organic base such as triethylamine, N,N-dimethylaniline, pyridine, 4-N,N-dimethylaminopyridine or 1,8-diazabicyclo[5.4.0]-7-undecene.

The amount of the base to be used may suitably be selected from a range of from 2 to 5 mols per 1 mol of the compound of the formula [XIV], and it is preferably from 2.2 to 3.0 mols.

The reaction temperature may be optionally selected from a range of from 0° C. to the reflux temperature of the reaction system, and it is preferably within a range of from 10° C. to 150° C. The reaction time varies depending upon the reaction temperature, the reaction substrate, the reaction amount, etc., and it is usually from 3 to 12 hours.

As another process, an aimed 3-triazolylphenyl sulfide derivative of the formula [I] can be produced by reacting a compound of the formula [XIV] with aqueous ammonia to produce a compound of the formula [XIV-1] (Step 2-1), and reacting this compound with a compound of the formula [XV-3] or [XV-4] in a solvent in the presence of a base or in the presence of an acid catalyst (Step 2-2).

(Step 2-1)

The amount of aqueous ammonia to be used in this step may suitably be selected from a range of from 1 to 10 mols per 1 mol of the compound of the formula [XIV], and it is preferably from 2.0 to 5.0 mols.

The solvent to be used in this step may, for example, be an ether such as diethyl ether, tetrahydrofuran or dioxane, an aromatic hydrocarbon such as benzene, toluene, xylene or chlorobenzene, a halogenated hydrocarbon such as dichloromethane, chloroform or dichloroethane, an aprotic polar solvent such as acetonitrile, N,N-dimethylformamide, N,N-dimethylacetamide, N-methyl-2-pyrrolidone, dimethyl sulfoxide or sulfolane, an alcohol such as methanol, ethanol or isopropyl alcohol, a nitrile such as acetonitrile or propionitrile, an ester such as ethyl acetate or ethyl propionate, an aliphatic hydrocarbon such as pentane, hexane, cyclohexane or heptane, a pyridine such as pyridine or picoline, or water, or a solvent mixture thereof.

The reaction temperature may be optionally selected from a range of from −30° C. to the reflux temperature of the reaction system, and it is preferably within a range of from −10° C. to 100° C.

The reaction time varies depending upon the reaction temperature, the reaction substrate, the reaction amount, etc., and it is usually from 10 minutes to 20 hours.

(Step 2-2)

Further, the amount of the compound of the formula [XV-3] or the compound of the formula [XV-4] to be used in this step is within a range of from 1 mol to large excess per 1 mol of the compound of the formula [XIV-1], and it is preferably from 1.0 to 2.0 mols.

The acid catalyst to be used in this step may, for example, be a sulfonic acid such as methanesulfonic acid or p-toluenesulfonic acid, an inorganic acid such as hydrochloric acid or sulfuric acid, or a carboxylic acid such as acetic acid or trifluoroacetic acid.

The amount of the acid catalyst to be used may suitably be selected from a range of from 0.01 mol to large excess per 1 mol of the compound of the formula [XIV-1], and it is preferably from 0.05 to 1.0 mols.

The solvent to be used in this step may be the same solvent as defined for the above Step 1.

The base to be used in this reaction may, for example, be an inorganic base such as a hydroxide of an alkali metal such as sodium hydroxide or potassium hydroxide, a hydroxide of an alkaline earth metal such as calcium hydroxide or magnesium hydroxide, a carbonate of an alkali metal such as sodium carbonate or potassium carbonate, or a bicarbonate of an alkali metal such as sodium hydrogencarbonate or potassium hydrogencarbonate, a metal hydride such as sodium hydride or potassium hydride, a metal salt of an alcohol such as sodium methoxide, sodium ethoxide or potassium tert-butoxide, or an organic base such as triethylamine, N,N-dimethylaniline, pyridine, 4-N,N-dimethylaminopyridine or 1,8-diazabicyclo[5.4.0]-7-undecene.

The amount of the base to be used may suitably be selected from a range of from 1 mol to large excess per 1 mol of the compound of the formula [XIV-1], and it is preferably from 1.0 to 1.5 mols.

The reaction temperature may be optionally selected from a range of from −30° C. to the reflux temperature of the reaction system, and it is preferably within a range of from −10° C. to 100° C.

The reaction time varies depending upon the reaction temperature, the reaction substrate, the reaction amount, etc., and it is usually from 10 minutes to 20 hours.

<Production Process 8>

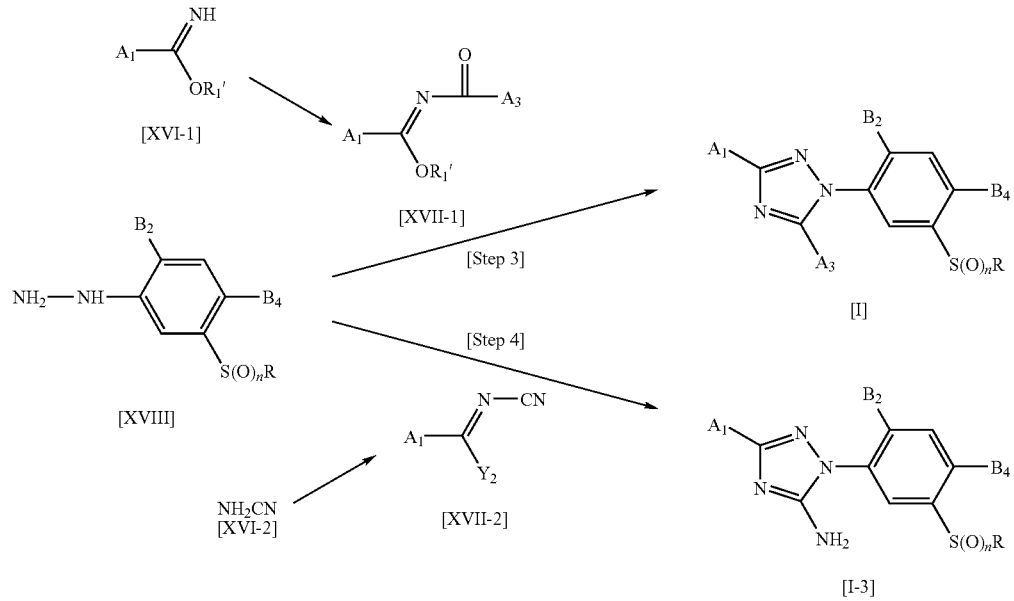

wherein $Y_2$ is a halogen atom, an alkoxy group or an alkylthio group which may be substituted by halogen, and $R_1'$, $A_1$, $A_3$, $B_2$, $B_4$, R and n are as defined above.

(Step 3)

A compound of the present invention of the formula [I] can be produced by reacting a compound of the formula [XVII-1] derived from a compound of the formula [XVI-1] and an acid halide, an acid anhydride or the like, with a compound of the formula [XVIII].

The amount of the compound of the formula [XVII-1] may suitably be selected from a range of from 1.0 to 5.0 mols per 1 mol of the compound of the formula [XVIII], and it is preferably from 1.0 to 1.5 mols.

The solvent to be used in this step may, for example, be an ether such as diethyl ether, tetrahydrofuran or dioxane, an aromatic hydrocarbon such as benzene, toluene, xylene or chlorobenzene, an aprotic polar solvent such as acetonitrile, N,N-dimethylformamide, N,N-dimethylacetamide, N-methyl-2-pyrrolidone, dimethyl sulfoxide or sulfolane, an alcohol such as methanol, ethanol or isopropyl alcohol, a halogenated hydrocarbon such as methylene chloride, chloroform or dichloroethane, an aliphatic hydrocarbon such as pentane, hexane, cyclohexane or heptane, a ketone such as acetone, methyl ethyl ketone or cyclohexanone, or water.

The reaction temperature may be optionally selected from a range of from −30° C. to the reflux temperature of the reaction system, and it is preferably within a range of from −10° C. to 100° C. The reaction time varies depending upon the reaction temperature, the reaction substrate, the reaction amount, etc., and it is usually from 10 minutes to 20 hours.

(Step 4)

Further, an aimed 3-triazilylphenyl sulfide derivative of the formula [I-3] can be produced by reacting a compound of the formula [XVII-2] derived from a compound of the formula [XVI-2] and carbon disulfide, an alkyl halide or the like, with a compound of the formula [XVIII].

The amount of the compound of the formula [XVII-2] may suitably be selected from a range of from 1.0 to 10 mols per 1 mol of the compound of the formula [XVIII], and it is preferably from 1.0 to 1.5 mols.

The solvent to be used in this step may be the same solvent as defined for the above Step 3.

The reaction temperature may be optionally selected from a range of from −30° C. to the reflux temperature of the reaction system, and it is preferably within a range of from −10° C. to 100° C.

The reaction time varies depending upon the reaction temperature, the reaction substrate, the reaction amount, etc., and it is usually from 10 minutes to 20 hours.

<Production Process 9>

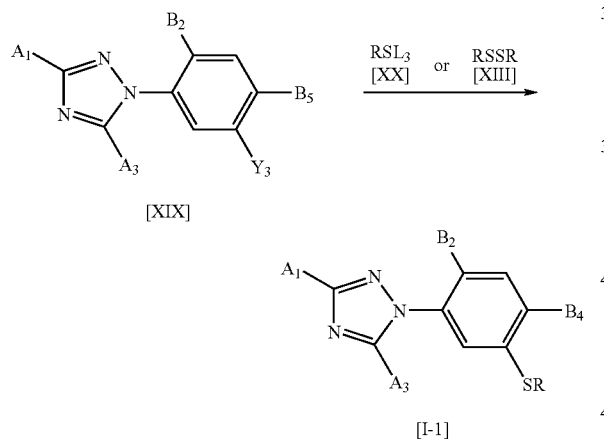

wherein $Y_3$ is a hydrogen atom or a halogen atom, and $L_3$, $A_1$, $A_3$, $B_2$, $B_4$ and R are as defined above.

A compound of the present invention of the formula [I-1] can be produced by reacting a compound of the formula [XIX] with a metal or an organic metal compound, followed by reaction with a compound of the formula [XX] or [XIII].

The amount of the compound of the formula [XX] or [XIII] to be used may suitably be selected from a range of from 1 to 5 mols per 1 mol of the compound of the formula [XIX], and it is preferably from 1.0 to 2.0 mols.

The solvent to be used in this reaction may, for example, be an ether such as diethyl ether, tetrahydrofuran or dioxane, an aromatic hydrocarbon such as benzene, toluene, xylene or chlorobenzene, an aliphatic hydrocarbon such as pentane, hexane, cyclohexane or heptane, or a pyridine such as pyridine or picoline, or a solvent mixture thereof.

The metal to be used in this reaction may, for example, be an alkali metal such as lithium or an alkaline earth metal such as magnesium, and its amount to be used may suitably be selected from a range of from 1 to 3 mols per 1 mol of the compound of the formula [XIX], and it is preferably from 1.0 to 1.1 mols.

The organic metal compound to be used in this reaction may, for example, be an alkyllithium such as n-butyllithium, and its amount to be used may suitably be selected from a range of from 1 to 3 mols per 1 mol of the compound of the formula [XIX], and it is preferably from 1.0 to 1.1 mols.

The reaction temperature may be optionally selected from a range of from −90° C. to the reflux temperature of the reaction system, and it is preferably within a range of from −78° C. to 70° C.

The reaction time varies depending upon the reaction temperature, the reaction substrate, the reaction amount, etc., and it is usually from 10 minutes to 20 hours.

<Production Process 10>

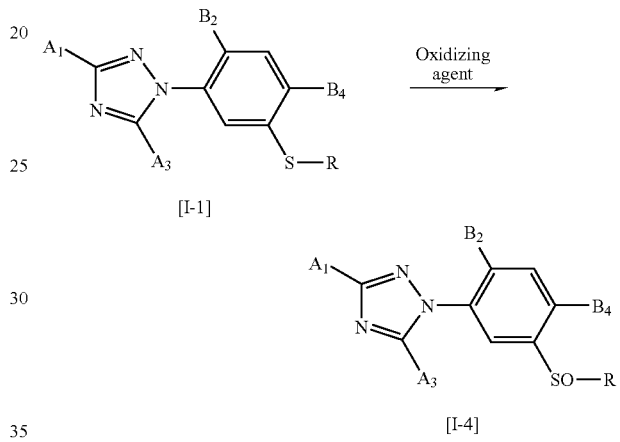

wherein $A_1$, $A_3$, $B_2$, $B_4$ and R are as defined above.

A compound of the present invention of the formula [I-4] can be produced by reacting a compound of the formula [I-1] with an oxidizing agent in the presence or absence of a catalyst.

The oxidizing agent may, for example, be hydrogen peroxide, m-chloroperbenzoic acid, sodium periodate, OXONE (tradename, manufactured by E.I. du Pont; containing potassium hydrogenperoxosulfate), N-chlorosuccinimide, N-bromosuccinimide, tert-butyl hypochlorite or sodium hypochlorite.

The amount of the oxidizing agent to be used may suitably be selected from a range of from 1 to 6 mols per 1 mol of the compound of the formula [I-1], and it is preferably from 1.0 to 1.2 mols.

The catalyst to be used in this reaction may, for example, be sodium tungstate.

The amount of the catalyst to be used may suitably be selected from a range of from 0 to 1 mol per 1 mol of the compound of the formula [I-1], and it is preferably from 0.01 to 0.1 mol.

The solvent to be used in this reaction may, for example, be an ether such as diethyl ether, tetrahydrofuran or dioxane, an aromatic hydrocarbon such as benzene, toluene, xylene or chlorobenzene, an aprotic polar solvent such as acetonitrile, N,N-dimethylformamide, N,N-dimethylacetamide, N-methyl-2-pyrrolidone, dimethyl sulfoxide or sulfolane, an alcohol such as methanol, ethanol or isopropyl alcohol, a halogenated hydrocarbon such as methylene chloride, chloroform or dichloroethane, an aliphatic hydrocarbon such as pentane, hexane, cyclohexane or heptane, ketone such as acetone, methyl ethyl ketone or cyclohexanone, acetic acid, or water, or a solvent mixture thereof.

The reaction temperature may be optionally selected from a range of from −30° C. to the reflux temperature of the reaction system, and it is preferably within a range of from −10° C. to 100° C.

The reaction time varies depending upon the reaction temperature, the reaction substrate, the reaction amount, etc., and it is usually from 10 minutes to 20 hours.

<Production Process 11>

A compound of the present invention of the formula [I] can be produced from a 3-triazolylphenyl sulfide derivative by converting a functional group by a generally known method:

The phenylalkyl halide to be used in this step may, for example, be benzyl bromide, 4-methoxybenzyl chloride or 4-chlorobenzyl bromide.

The heterocyclic alkyl halide to be used in this step may, for example, be 2-chloro-5-chloromethylpyridine.

The acyl halide to be used in this step may, for example, be acetyl chloride, propionyl chloride, difluoroacetyl chloride, trifluoroacetyl chloride, methyl chloroformate, ethyl chloroformate or N,N-dimethylcarbamoyl chloride.

The acid anhydride to be used in this step may, for example, be acetic anhydride, trifluoroacetic anhydride or chlorodifluoroacetic anhydride.

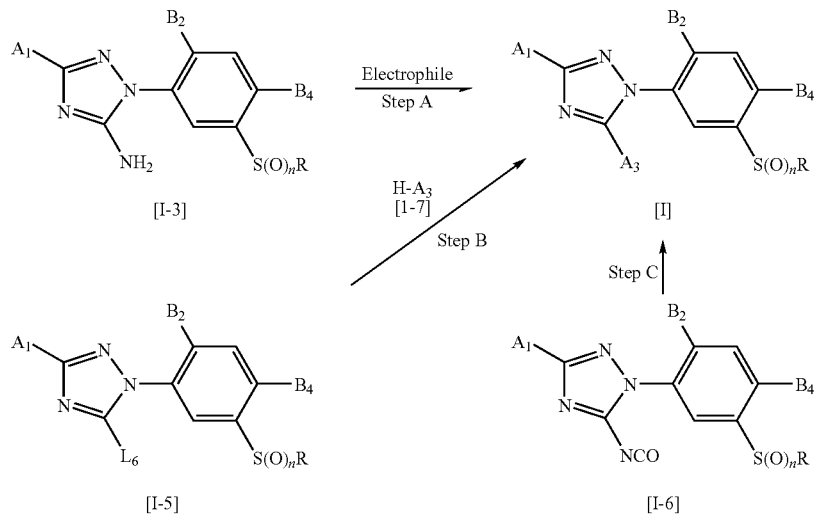

wherein $A_1$, $A_3$, $B_2$, $B_4$, n and R are as defined above, and $L_6$ is a hydrogen atom, a halogen atom, a methylthio group, a methylsulfinyl group, a methylsulfonyl group, a p-toluenesulfonyl group or the like.

(Step A)

A compound of the present invention of the formula [I] can be produced by reacting a compound of the present invention of the formula [I-3] with an electrophilic reagent in the presence or absence of a solvent, in the presence or absence of a base, in the presence or absence of an acid and in the presence or absence of a dehydration condensation agent.

The electrophile to be used in this step may, for example, be a halogenated alkane, a halogenated alkene, a halogenated alkyne, a phenylalkyl halide, a heterocyclic alkyl halide, an acyl halide, an acid anhydride, benzoic acid, a benzoyl halide, a heterocyclic carboxylic acid, a heterocyclic carboxylic halide, an aliphatic carboxylic halide, an isocyanate, an alcohol, an aromatic halide, a heterocyclic halide, a sulfonyl halide or a sulfonic anhydride, or a ketone or a thioketone.

The halogenated alkane to be used in this step may, for example, be methyl iodide, ethyl iodide or propyl iodide.

The halogenated alkene to be used in this step may, for example, be allyl bromide or 1,1,3-trichloropropene.

The halogenated alkyne to be used in this step may, for example, be propargyl bromide or 4-chloro-2-butyne.

The isocyanate to be used in this step may, for example, be methyl isocayanate, ethyl isocyanate or chlorosulfonyl isocyanate.

The aromatic halide to be used in this step may, for example, be 3,5-dichloro-4-fluorobenzotrifluoride.

The heterocyclic halide to be used in this step may, for example, be 2,3-dichloro-5-trifluoromethylpyridin.

The sulfonyl halide to be used in this step may, for example, be trifluoromethanesulfonyl fluoride, trifluoromethanesulfonyl chloride or difluoromethanesulfonyl chloride.

The sulfonic anhydride to be used in this step may, for example, be trifluoromethanesulfonic anhydride.

The ketone to be used in this step may, for example, be acetone or 4-hydroxy-3-methoxybenzaldehyde.

The benzoyl halide to be used in this step may, for example, be benzoyl chloride.

The heterocyclic carboxylic acid to be used in this step may, for example, be 3-pyridine carboxylic acid or thiophene carboxylic acid.

The heterocyclic carboxylic halide to be used in this step may, for example, be 3-pyridinecarboxylic chloride or thiophenecarboxylic chloride.

The aliphatic carboxylic halide to be used in this step may, for example, be acetyl chloride or propionyl chloride.

The alcohol to be used in this step may, for example, be methanol, ethanol or benzyl alcohol.

The amount of the electrophile to be used may suitably be selected from a range of from 1 to 100 mols per 1 mol of the compound of the formula [I-3], and it is preferably from 1 to 10 mols, more preferably from 1 to 3 mols.

In a case where a base is used in this step, the base to be used may, for example, be an inorganic base such as a hydroxide of an alkali metal such as sodium hydroxide or potassium hydroxide, a hydroxide of an alkaline earth metal such as calcium hydroxide or magnesium hydroxide, a carbonate of an alkali metal such as sodium carbonate or potassium carbonate, or a bicarbonate of an alkali metal such as sodium hydrogencarbonate or potassium hydrogencarbonate, a metal hydride such as sodium hydride or potassium hydride, a metal salt of an alcohol such as sodium methoxide, sodium ethoxide or potassium tert-butoxide, or an organic base such as triethylamine, N,N-dimethylaniline, pyridine, 4-N,N-dimethylaminopyridine or 1,8-diazabicyclo[5.4.0]-7-undecene.

In a case where a base is used, the amount of the base to be used may suitably be selected within a range of from 0.01 to 3 mols per 1 mol of the compound of the formula [I-3], and it is preferably from 0.1 to 2 mols, more preferably from 0.1 to 1.2 mols.

In a case where an acid is used in this step, the acid to be used is a Lewis acid, such as a sulfonic acid such as methanesulfonic acid or p-toluenesulfonic acid, an inorganic acid such as hydrochloric acid, hydrobromic acid or sulfuric acid, or a carboxylic acid such as acetic acid or trifluoroacetic acid.

In a case where an acid is used, the amount of the acid to be used may suitably be selected from a range of from 0.001 to 5 mols per 1 mol of the compound of the formula [I-3], and it is preferably from 0.01 to 2 mols, more preferably from 0.03 to 1.0 mols.

The solvent to be used in this step may, for example, be an ether such as diethyl ether, tetrahydrofuran or dioxane, an aromatic hydrocarbon such as benzene, toluene, xylene or chlorobenzene, an aprotic polar solvent such as acetonitrile, N,N-dimethylformamide, N,N-dimethylacetamide, N-methyl-2-pyrrolidone, dimethyl sulfoxide or sulfolane, an alcohol such as methanol, ethanol or isopropyl alcohol, a halogenated hydrocarbon such as methylene chloride, chloroform or dichloroethane, an aliphatic hydrocarbon such as pentane, hexane, cyclohexane or heptane, or a ketone such as acetone, methyl ethyl ketone or cyclohexanone, or a solvent mixture thereof.

In a case where a dehydration condensation agent is used in this step, the dehydration condensation agent to be used may be a carbodiimide such as dicyclohexylcarbodiimide.

In a case where a dehydration condensation agent is used, the amount of the dehydration condensation agent to be used may suitably be selected from a range of from 1 to 3 mols per 1 mol of the compound of the formula [I-3], and it is preferably from 1.0 to 1.2 mols.

The reaction temperature may be optionally selected from a range of from −20° C. to the reflux temperature of the reaction system, and it is preferably within a range of from 0° C. to 80° C.

The reaction time varies depending upon the reaction temperature, the reaction substrate, the reaction amount, etc., and it is usually from 15 minutes to 24 hours.

(Step B)

A compound of the present invention of the formula [I] can be produced by reacting a compound of the formula [I-5] with a compound of the formula [I-7] in the presence or absence of a base in the presence of a solvent.

In a case where a base is used in this process, the base to be used in this reaction may, for example, be an inorganic base such as a hydroxide of an alkali metal such as sodium hydroxide or potassium hydroxide, a hydroxide of an alkaline earth metal such as calcium hydroxide or magnesium hydroxide, a carbonate of an alkali metal such as sodium carbonate or potassium carbonate, or a bicarbonate of an alkali metal such as sodium hydrogencarbonate or potassium hydrogencarbonate, a metal hydride such as sodium hydride or potassium hydride, a metal salt of an alcohol such as sodium methoxide, sodium ethoxide or potassium tert-butoxide, or an organic base such as triethylamine, N,N-dimethylaniline, pyridine, 4-N,N-dimethylaminopyridine or 1,8-diazabicyclo[5.4.0]-7-undecene.

In a case where a base is used, the amount of the base to be used may suitably be selected from a range of from 1 to 10 mols per 1 mol of the compound of the formula [I-5], and it is preferably from 1 to 3 mols, more preferably from 1.0 to 1.2 mols.

The solvent to be used in this step may, for example, be an ether such as diethyl ether, tetrahydrofuran or dioxane, an aromatic hydrocarbon such as benzene, toluene, xylene or chlorobenzene, an aprotic polar solvent such as acetonitrile, N,N-dimethylformamide, N,N-dimethylacetamide, N-methyl-2-pyrrolidone, dimethyl sulfoxide or sulfolane, an alcohol such as methanol, ethanol or isopropyl alcohol, a halogenated hydrocarbon such as methylene chloride, chloroform or dichloroethane, an aliphatic hydrocarbon such as pentane, hexane, cyclohexane or heptane, or a ketone such as acetone, methyl ethyl ketone or cyclohexanone, or water, and a solvent mixture thereof may also be used.

The reaction temperature may be optionally selected from a range of from −20° C. to the reflux temperature of the reaction system, and it is preferably within a range of from −10° C. to 150° C.

The reaction time varies depending upon the reaction temperature, the reaction substrate, the reaction amount, etc., and it is usually from 15 minutes to 12 hours.

(Step C)

A compound of the present invention represented by the formula [I] can be produced by reacting a compound of the formula [I-6] with an amine, a carboxylic acid or an alcohol in the presence or absence of a solvent.

The amine to be used in this step may, for example, be methylamine, ethylamine, dimethylamine, propylamine, isopropylamine, hydrazine or methylhydrazine.

The carboxylic acid to be used in this step may, for example, be acetic acid, propionic acid, methoxyacetic acid or benzoic acid.

The alcohol to be used in this step may, for example, be methanol, ethanol, propanol, allyl alcohol, propargyl alcohol or cyclopropanol.

As the amount of the amine, carboxylic acid or alcohol to be used, from 1 mol to 100 mols, preferably from 1 mol to 30 mols, more preferably from 1 mol to 3 mols, of the amine, carboxylic acid or alcohol is used per 1 mol of the compound represented by the formula [I-6].

The solvent to be used in this reaction may, for example, be an ether such as diethyl ether, tetrahydrofuran or dioxane, an aromatic hydrocarbon such as benzene, toluene, xylene or chlorobenzene, an aprotic polar solvent such as acetonitrile, N,N-dimethylformamide, N,N-dimethylacetamide, N-methyl-2-pyrrolidone, dimethyl sulfoxide or sulfolane, an alcohol such as methanol, ethanol or isopropyl alcohol, a halogenated hydrocarbon such as methylene chloride, chloroform or dichloroethane, an aliphatic hydrocarbon such as pentane, hexane, cyclohexane or heptane, or a ketone such as acetone, methyl ethyl ketone or cyclohexanone, or a solvent mixture thereof.

The reaction temperature may be optionally selected from a range of from −20° C. to the reflux temperature of the reaction system, and it is preferably within a range of from −10° C. to 150° C.

The reaction time varies depending upon the reaction temperature, the reaction substrate, the reaction amount, etc., and it is usually from 30 minutes to 24 hours.

Now, synthesis of intermediates for production of the compounds of the present invention will be described in detail below.

<Intermediate Production Process 1>

Synthesis of Production Intermediates [II] and [IV]

Compounds of the formulae [II] and [IV] can be synthesized as follows. Needless to say, they are interconvertible through oxidation-reduction reaction. Especially, the compound of the formula [II] can be easily oxidized by atmospheric oxygen into a compound of the formula [IV] in some cases:

wherein $R_2'$ is a methyl group or a trifluoromethyl group, and $Y_2$, $A_1$, $A_3$, $B_2$ and $B_4$ are as defined above.

(Step 5)

That is, an aimed compound represented by the formula [II] or [IV] can be produced as follows. A compound of the formula [XXI] is oxidized by an oxidizing agent into a methyl sulfoxide, followed by the Pummerer rearrangement reaction with acetic anhydride or trifluoroacetic anhydride into an acyloxymethyl sulfide represented by the formula [XXII], and then the resulting compound is hydrolyzed.

The oxidizing agent may, for example, be hydrogen peroxide, m-chloroperbenzoic acid, sodium periodate, OXONE (tradename, manufactured by E.I. du Pont; containing potassium hydrogenperoxosulfate), N-chlorosuccinimide, N-bromosuccinimide, tert-butyl hypochlorite or sodium hypochlorite.

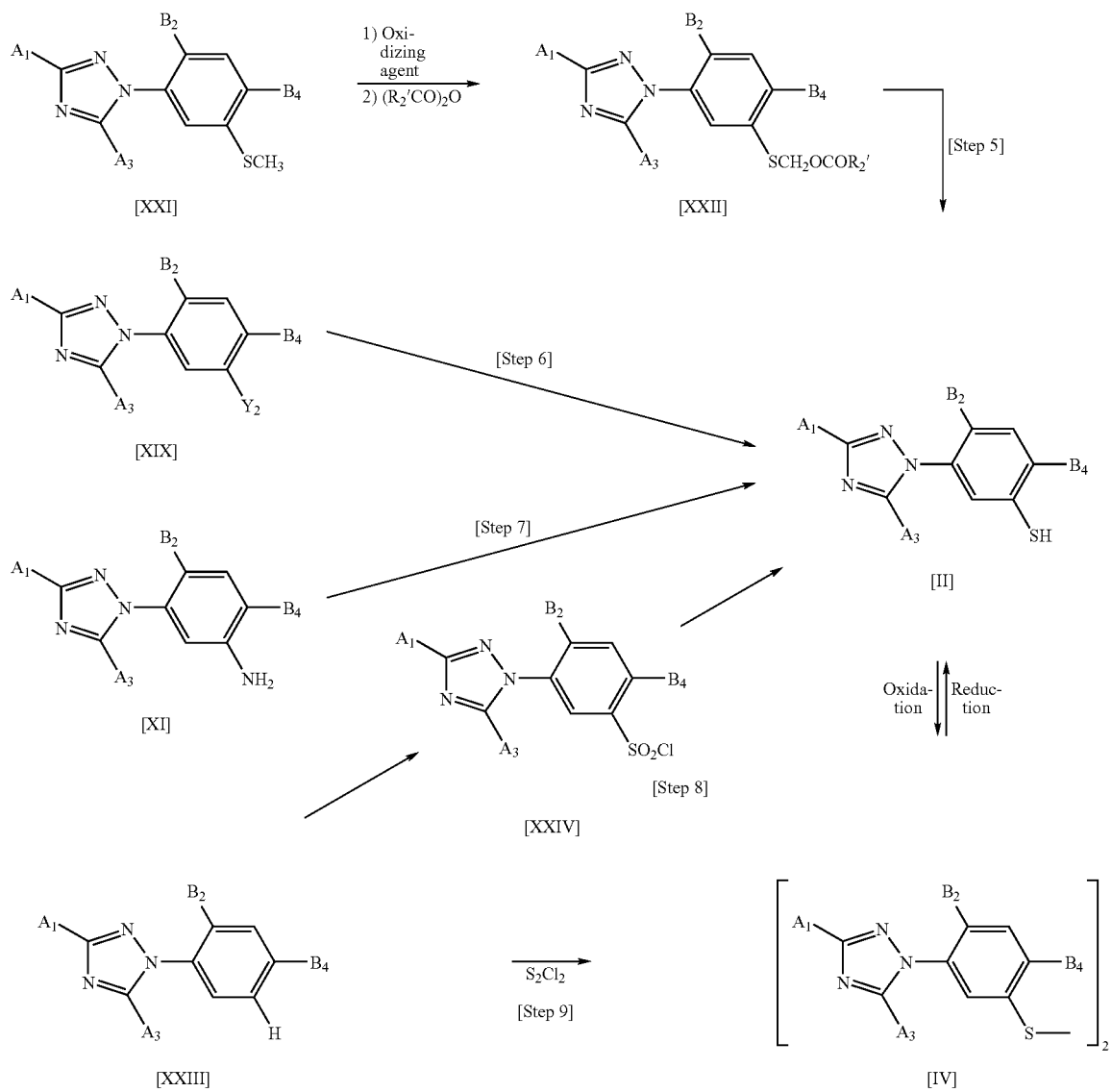

The amount of the oxidizing agent to be used may suitably be selected from a range of from 1 to 3 mols per 1 mol of the compound of the formula [XXI], and it is preferably from 1.0 to 1.2 mols.

As the amount of acetic anhydride or trifluoroacetic anhydride to be used, it can be used as a reaction solvent in an amount of 1 mol or more per 1 mol of the compound of the formula [XXI], and its amount is preferably from 1.0 to 3.0 mols.

The reaction temperature of each reaction may be optionally selected from a range of from $-10°$ C. to the reflux temperature of the reaction system, and it is preferably within a range of from $0°$ C. to $50°$ C.

The reaction time varies depending upon the reaction temperature, the reaction substrate, the reaction amount, etc., and it is usually from 5 minutes to 12 hours.

(Step 6)

A compound represented by the formula [II] can be produced by treating a compound of the formula [XIX] with a metal or an organo metallic compound in a solvent and then reacting sulfur therewith.

The solvent to be used in this step may, for example, be an ether such as diethyl ether, tetrahydrofuran or dioxane, an aromatic hydrocarbon such as benzene, toluene, xylene or chlorobenzene, an aliphatic hydrocarbon such as pentane, hexane, cyclohexane or heptane, or a pyridine such as pyridine or picoline, or a solvent mixture thereof.

The metal to be used in this step may, for example, be lithium or magnesium.

The amount of the metal to be used may suitably be selected from a range of from 1 to 3 mols per 1 mol of the compound of the formula [XIX], and it is preferably from 1.0 to 1.2 mols.

The organo metallic compound to be used in this step may, for example, be n-butyllithium.

The amount of the organo metallic compound to be used may optionally be selected from a range of from 1 to 3 mols per 1 mol of the compound of the formula [XIX], and it is preferably from 1.0 to 1.2 mols.

The amount of sulfur to be used may suitably be selected from a range of from 1 to 5 mols per 1 mol of the compound of the formula [XIX], and it is preferably from 1.0 to 2.0 mols.

The reaction temperature of each reaction may optionally be selected from a range of from $-60°$ C. to the reflux temperature of the reaction system, and it is preferably within a range of from $-60°$ C. to room temperature.

The reaction time varies depending upon the reaction temperature, the reaction substrate, the reaction amount, etc., and it is usually from 30 minutes to 12 hours.

(Step 7)

A compound represented by the formula [II] can be produced as follows. A compound represented by the formula [XI] is converted into a diazonium salt in the same manner as in the above Production Process 6. Then, the diazonium salt is reacted with a xanthate or a thiocyanate, followed by alkali hydrolysis.

The amount of the xanthate or the thiocyanate to be used may suitably be selected from a range of from 1 to 3 mols per 1 mol of the compound of the formula [XI], and it is preferably from 1.0 to 1.5 mols.

The reaction temperature of each reaction may optionally be selected from a range of from $-70°$ C. to the reflux temperature of the reaction system, and it is preferably from $-20°$ C. to $100°$ C.

The reaction time varies depending upon the reaction temperature, the reaction substrate, the reaction amount, etc., and it is usually from 10 minutes to 20 hours.

(Step 8)

A synthetic intermediate represented by the formula [II] can be produced by treating a compound of the formula [XXIII] with chlorosulfonic acid into a sulfonyl chloride of the formula [XXIV], and reducing it with lithium aluminum hydride, with zinc and an acid, with tin and an acid or with red phosphorus and iodine.

The amount of chlorosulfonic acid to be used in this step may suitably be selected from a range of from 2 to 5 mols per 1 mol of the compound of the formula [XXIII], and it is preferably from 2.2 to 3.0 mols.

The acid may, for example, be hydrochloric acid or sulfuric acid.

The amount of chlorosulfonic acid to be used may suitably be selected from a range of from 2 to 10 mols per 1 mol of the compound of the formula [XXIII], and it is preferably from 2.2 to 3.5 mols.

The amount of lithium aluminum hydride, zinc and an acid, tin and an acid, or red phosphorus and iodine, may suitably be selected from a range of from 1 to 5 mols per 1 mol of the compound of the formula [XXIII], and it is preferably from 1.5 to 2.0 mols.

(Step 9)

A compound represented by the formula [IV] can be produced by reacting a compound of the formula [XXIII] with disulfur dichloride in the presence or absence of a catalyst. Further, a compound represented by the formula [II] can be produced by reducing the compound represented by the formula [IV] by a conventional method.

The amount of disulfur dichloride to be used may suitably be selected from a range of from 1 to 5 mols per 1 mol of the compound of the formula [XXIII], and it is preferably from 1.1 to 1.5 mols.

The catalyst to be used in this step may, for example, be a Lewis acid catalyst such as aluminum chloride, tin(II)chloride or tin(IV)chloride.

The amount of the catalyst to be used may suitably be selected from a range of from 1 to 5 mols per 1 mol of the compound of the formula [XXIII], and it is preferably from 1.1 to 2.0 mols.

The solvent to be used in this step may, for example, be a halogenated hydrocarbon such as methylene chloride, chloroform or dichloroethane, or an aromatic hydrocarbon such as chlorobenzene or dichlorobenzene.

The reaction temperature may optionally be selected from a range of from $-30°$ C. to the reflux temperature of the reaction, and it is preferably within a range of from $-10°$ C. to $100°$ C.

The reaction time varies depending upon the reaction temperature, the reaction substrate and the reaction amount, and it is usually from 1 to 20 hours.

<Intermediate Production Process 2>

Further, a synthetic intermediate of the formula [II-1] can be produced by substitution reaction from a compound of the formula [IX] wherein $B_5$ is an electron-withdrawing group:

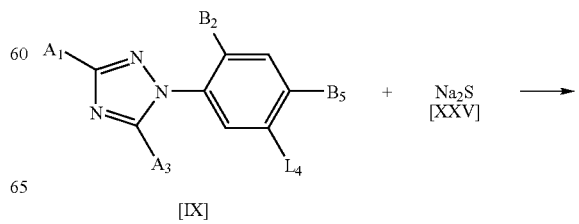

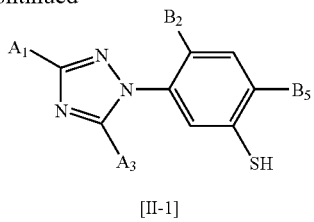

[II-1]

wherein $L_4$, $A_1$, $A_3$, $B_2$ and $B_5$ are as defined above.

That is, an aimed 3-triazolylphenylthiol derivative represented by the formula [II-1] can be produced by reacting a compound of the formula [IX] with a compound of the formula [XXV] in a solvent in the presence of a base, followed by neutralization with a mineral acid or the like.

The amount of the compound of the formula [XXV] to be used may suitably be selected from a range of from 1 to 3 mols per 1 mol of the compound of the formula [IX], and it is preferably from 1.0 to 1.5 mols.

The solvent to be used in this step may, for example, be an ether such as diethyl ether, tetrahydrofuran or dioxane, an aromatic hydrocarbon such as benzene, toluene, xylene or chlorobenzene, an aprotic polar solvent such as N,N-dimethylformamide, N,N-dimethylacetamide, N-methyl-2-pyrrolidone, dimethyl sulfoxide or sulfolane, an alcohol such as methanol, ethanol or isopropyl alcohol, a halogenated hydrocarbon such as methylene chloride, chloroform or dichloroethane, an aliphatic hydrocarbon such as pentane, hexane, cyclohexane or heptane, a ketone such as acetone, methyl ethyl ketone or cyclohexanone, or water.

The base to be used in this step may, for example, be an inorganic base such as a hydroxide of an alkali metal such as sodium hydroxide or potassium hydroxide, a hydroxide of an alkaline earth metal such as calcium hydroxide or magnesium hydroxide, a carbonate of an alkali metal such as sodium carbonate or potassium carbonate, or a bicarbonate of an alkali metal such as sodium hydrogencarbonate or potassium hydrogencarbonate, a metal hydride such as sodium hydride or potassium hydride, a metal salt of an alcohol such as sodium methoxide, sodium ethoxide or potassium tert-butoxide, or an organic base such as triethylamine, N,N-dimethylaniline, pyridine, 4-N,N-dimethylaminopyridine or 1,8-diazabicyclo[5.4.0]-7-undecene.

The amount of the base to be used may suitably be selected from a range of from 1 to 5 mols per 1 mol of the compound of the formula [IX], and it is preferably from 1.0 to 1.2 mols.

The mineral acid may, for example, be hydrochloric acid or sulfuric acid.

The amount of the mineral acid to be used may suitably be selected from a range of from 1 to 5 mols per 1 mol of the compound of the formula [IX], and it is preferably from 1.0 to 2.0 mols.

The reaction temperature may be optionally selected from a range of from −30° C. to the reflux temperature of the reaction system, and it is preferably within a range of from −20° C. to 100° C. The reaction time varies depending upon the reaction temperature, the reaction substrate, the reaction amount, etc., and it is usually from 10 minutes to 20 hours.

<Intermediate Production Process 3>

Synthesis of Production Intermediate [VI]

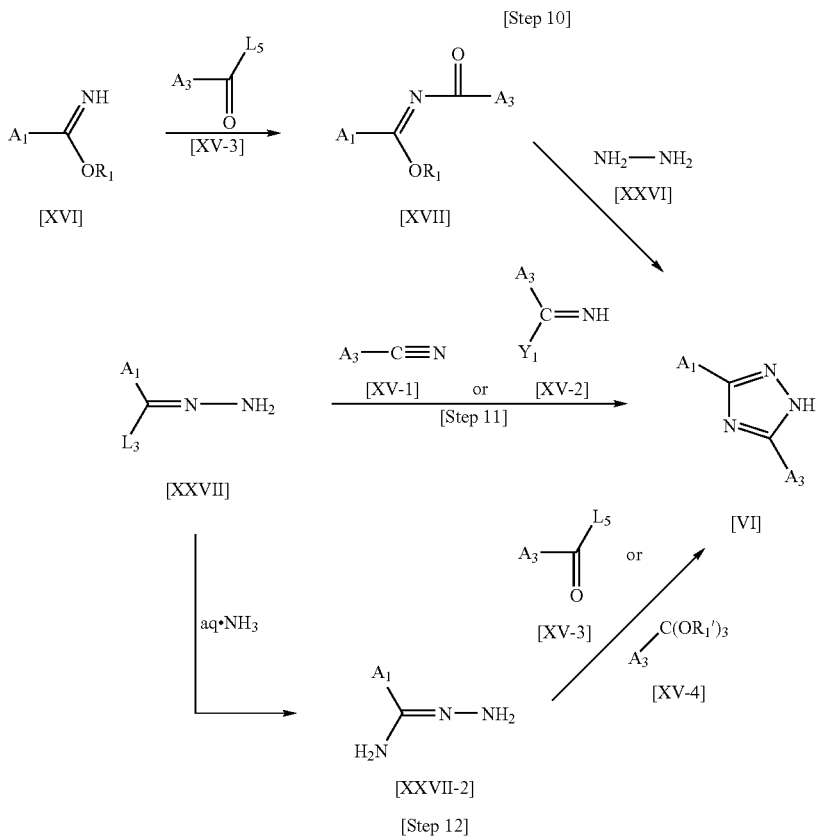

wherein $A_1$, $A_3$, R', $Y_1$, $L_3$ and $L_5$ are as defined above.

(Step 10)

A synthetic intermediate represented by the formula [VI] can be produced, in the same manner as in Production Process 8, by converting a compound of the formula [XVI] into a compound of the formula [XVII], and reacting hydrazine hydrate [XXVI] of the formula [XXVI] therewith.

The amount of hydrazine hydrate [XXVI] to be used may suitably be selected from a range of from 1 to 5 mols per 1 mol of the compound of the formula [XVII], and it is preferably from 1.0 to 2.0 mols.

(Step 11)

Further, a synthetic intermediate represented by the formula [VI] can be produced, in the same manner as in Production Process 7, by reacting a compound of the formula [XXVII] with a compound of the formula [XV-1] or [XV-2].

The amount of the compound represented by the formula [XV-1] or [XV-2] to be used is from 1 mol to large excess per 1 mol of the compound of the formula [XXVII], and it is preferably from 1.0 to 2.0 mols.

The reaction temperature may be optionally selected from a range of from −70° C. to the reflux temperature of the reaction system, and it is preferably within a range of from −20° C. to 100° C.

The reaction time varies depending upon the reaction temperature, the reaction substrate, the reaction amount, etc., and it is usually from 10 minutes to 20 hours.

(Step 12)

A synthetic intermediate represented by the formula [VI] can be produced by reacting a compound represented by the formula [XXVII] with aqueous ammonia to produce an amidrazone represented by the formula [XXVII-2], and reacting this reaction product with a compound represented by the formula [XV-3] or [XV-4].

The amount of aqueous ammonia to be used may suitably be selected from a range of from 1 to 10 mols per 1 mol of the compound represented by the formula [XXVII], and it is preferably from 2.0 to 5.0 mols.

The amount of the compound represented by the formula [XV-3] or [XV-4] is from 1 mol to large excess per 1 mol of the compound represented by the formula [XXVII-2], and it is preferably from 1.0 to 2.0 mols.

The reaction temperature may be optionally selected from a range of from −70° C. to the reflux temperature of the reaction system, and it is preferably within a range of from −20° C. to 100° C. The reaction time varies depending upon the reaction temperature, the reaction substrate, the reaction amount, etc., and it is usually from 10 minutes to 20 hours.

<Intermediate Production Process 4>

Synthesis of Production Intermediate [XIV]

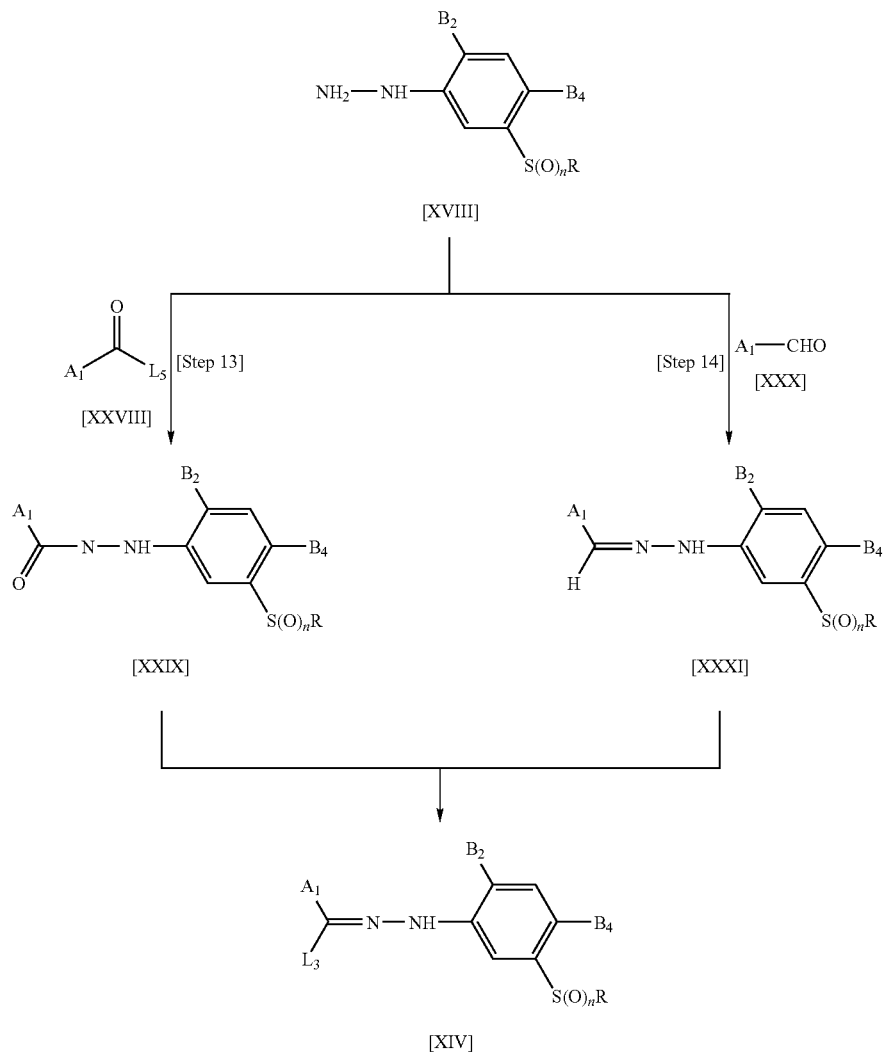

wherein $L_3$, $L_5$ $A_1$, $B_2$, $B_4$, R and n are as defined above.

(Step 13)

An aimed compound represented by the formula [XIV] can be produced by reacting a phenylhydrazine derivative represented by the formula [XVIII] with a compound represented by the formula [XXVIII] in a solvent in the presence of a base for acylation to produce a compound represented by the formula [XXIX] and then treating the compound represented by the formula [XXIX] with a halogenating agent.

The amount of the compound of the formula [XXVIII] to be used may suitably be selected from a range of from 1 to 5 mols per 1 mol of the compound of the formula [XVIII], and it is preferably from 1.0 to 1.1 mols.

The solvent to be used in this step may, for example, be an ether such as diethyl ether, tetrahydrofuran or dioxane, an aromatic hydrocarbon such as benzene, toluene, xylene or chlorobenzene, a halogenated hydrocarbon such as dichloromethane, chloroform or dichloroethane, an aprotic polar solvent such as N,N-dimethylformamide, N,N-dimethylacetamide, N-methyl-2-pyrrolidone, dimethyl sulfoxide or sulfolane, an alcohol such as methanol, ethanol or isopropyl alcohol, a nitrile such as acetonitrile or propionitrile, an ester such as ethyl acetate or ethyl propionate, an aliphatic hydrocarbon such as pentane, hexane, cyclohexane or heptane, a pyridine such as pyridine or picoline, or water, or a solvent mixture thereof.

The base to be used in this step may, for example, be an inorganic base such as a hydroxide of an alkali metal such as sodium hydroxide or potassium hydroxide, a hydroxide of an alkaline earth metal such as calcium hydroxide or magnesium hydroxide, a carbonate of an alkali metal such as sodium carbonate or potassium carbonate, or a bicarbonate of an alkali metal such as sodium hydrogencarbonate or potassium hydrogencarbonate, a metal hydride such as sodium hydride or potassium hydride, a metal salt of an alcohol such as sodium methoxide, sodium ethoxide or potassium tert-butoxide, or an organic base such as triethylamine, N,N-dimethylaniline, pyridine, 4-N,N-dimethylaminopyridine or 1,8-diazabicyclo[5.4.0]-7-undecene.

The amount of the base to be used is from 1 mol to large excess per 1 mol of the compound of the formula [XVIII], and it is preferably from 1.0 to 1.2 mols.

The halogenating agent may, for example, be phosphorus trichloride, phosphorus tribromide, thionyl chloride, phosphorus oxychloride, phosphorus pentachloride, triphenylphosphine/carbon tetrachloride or triphenylphosphine/carbon tetrabromide.

The amount of the halogenating agent to be used is from 1 mol to large excess per 1 mol of the compound of the formula [XXIX], and it is preferably from 1.0 to 1.5 mols.

The reaction temperature may be optionally selected from a range of from −70° C. to the reflux temperature of the reaction system, and it is preferably within a range of from −20° C. to 150° C.

The reaction time varies depending upon the reaction temperature, the reaction substrate, the reaction amount, etc., and it is usually from 10 minutes to 20 hours.

(Step 14)

Otherwise, an aimed compound represented by the formula [XIV] can be produced by reacting a phenylhydrazine derivative represented by the formula [XVIII] with an aldehyde compound represented by the formula [XXX] in a solvent in the presence or absence of an acid catalyst to form a phenylhydrazone derivative represented by the formula [XXXI], and treating it with a halogenating agent.

The amount of the compound of the formula [XXX] to be used may suitably be selected from a range of from 1 to 5 mols per 1 mol of the compound of the formula [XVIII], and it is preferably from 1.0 to 1.2 mols.

The solvent to be used in this step is not limited so long as it does not inhibit the reaction and it may, for example, be an aromatic hydrocarbon such as benzene, toluene or xylene, an ether such as diethyl ether, tetrahydrofuran, 1,2-dimethoxyethane or dioxane, a ketone such as acetone or methyl ethyl ketone, a nitrile such as acetonitrile or propionitrile, an aprotic polar solvent such as dimethyl sulfoxide, N,N-dimethylformamide or N,N-dimethylacetamide, an aliphatic hydrocarbon such as pentane, hexane, cyclohexane or heptane, or a pyridine such as pyridine or picoline, or a solvent mixture thereof.

The acid catalyst to be used in this step may, for example, be a Lewis acid such as a sulfonic acid such as p-toluenesulfonic acid, or titanium tetrachloride.

In a case where an acid catalyst is used, its amount to be used may suitably be selected from a range of from 1 to 5 mols per 1 mol of the compound of the formula [XVIII], and it is preferably from 1.0 to 1.2 mols.

The halogenating agent to be used in this step may, for example, be chlorine, N-chlorosuccinimide, N-bromosuccinimide or tert-butyl hypochlorite.

The amount of the halogenating agent to be used may suitably be selected from a range of from 1 to 5 mols per 1 mol of the compound of the formula [XXXI], and it is preferably from 1.0 to 1.1 mols.

The reaction temperature may be optionally selected from a range of from −70° C. to the reflux temperature of the reaction system, and it is preferably within a range of from −20° C. to 150° C. The reaction time varies depending upon the reaction temperature, the reaction substrate, the reaction amount, etc., and it is usually from 10 minutes to 20 hours.

The phenylhydrazine of the formula [XVIII] can be synthesized from the corresponding aniline in accordance with a conventional method such as a method as disclosed in Comprehensive Organic Functional Group Transformations, vol. 2, p. 769.

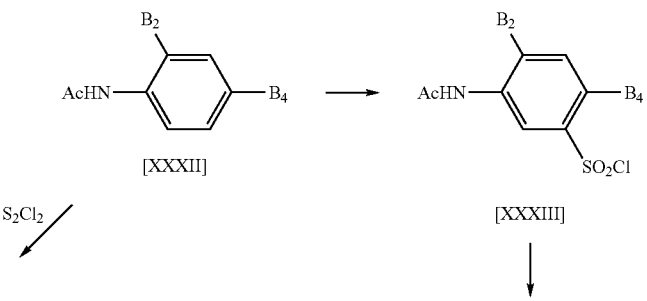

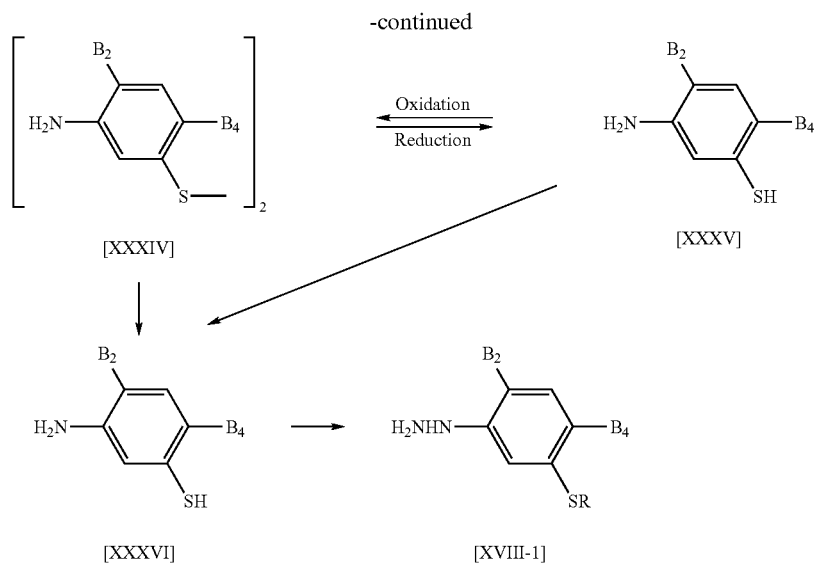

wherein $B_2$, $B_4$ and R are as defined above, and Ac is an acetyl group.

A 3-thioaniline derivative represented by the formula [XXXVI] can be produced by converting an acetanilide represented by the formula [XXXII] into a disulfide represented by the formula [XXXIV] or a thiol represented by the formula [XXXV] in the same manner as in Intermediate Production Process 1, followed by a process as disclosed in the above Production Process 1 or 2.

A phenylhydrazine represented by the formula [XVIII-1] can be produced by reacting a compound presented by the formula [XXXVI] with a nitrite in the presence of a mineral acid to form a diazonium salt, and reducing it with zinc powder, a sulfite, tin chloride or the like.

The mineral acid may, for example, be hydrochloric acid or sulfuric acid.

The amount of the mineral acid to be used may suitably be selected from a range of from 2 to 10 mols per 1 mol of the compound [XXXVI], and it is preferably from 3 to 5 mols.

The amount of the nitrite to be used may suitably be selected from a range of from 1.0 to 5.0 mols per 1 mol of the compound [XXXVI], and it is preferably from 1.0 to 1.2 mols.

The reaction temperature of each reaction may be selected from a range of from –20° C. to 50° C., and it is preferably from –5° C. to 20° C.

The reaction time varies depending upon the reaction temperature, the reaction substrate, the reaction amount, etc., and it is usually from 30 minutes to 5 hours.

A compound of the formula [I-5] can be produced by the following process:

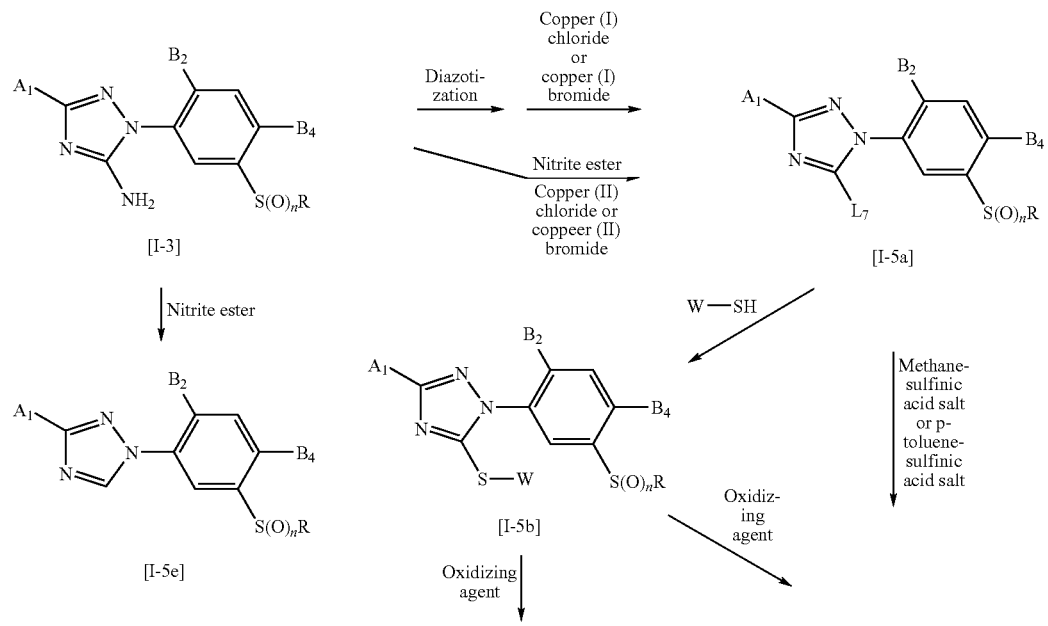

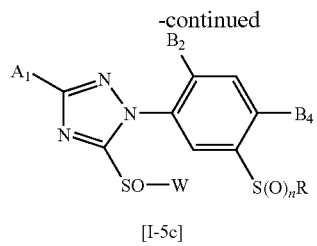

[I-5c]

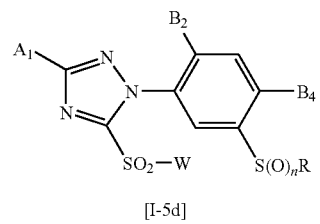

[I-5d]

wherein $A_1$, $A_3$, $B_2$, $B_{41}$, n and R are as defined above, $L_7$ is a halogen atom, and W is a methylthio group or a p-tolylthio group.

A compound of the formula [I-5a] can be produced by diazotizing a compound of the formula [I-3] by a conventional method, followed by reaction with copper(I)chloride or copper(I)bromide.

The amount of copper(I)chloride or copper(I) bromide to be used is from 1 to 5 mols per 1 mol of the compound of the formula [I-3], preferably from 1 to 2 mols.

The solvent to be used may, for example, be a carboxylic acid such as acetic acid, a mineral acid such as hydrochloric acid, hydrobromic acid or sulfuric acid, or water, or a solvent mixture thereof.

The reaction temperature may be optionally selected from a range of from −70° C. to the reflux temperature of the reaction system, and it is preferably within a range of from −20° C. to 100° C. The reaction time varies depending upon the reaction temperature, the reaction substrate, the reaction amount, etc., and it is usually from 10 minutes to 20 hours.

A compound of the formula [I-5a] can be produced also by a reaction in the coexistence of a nitrite ester such as t-butyl nitrite or isoamyl nitrite with copper(II)chloride or copper(II) bromide in a solvent.

The amount of the nitrite ester to be used is from 1 to 5 mols per 1 mol of the compound of the formula [I-3], preferably from 1 to 2 mols.

The amount of copper(II)chloride or copper(II)bromide to be used is from 1 to 5 mols per 1 mol of the compound of the formula [I-3], preferably from 1 to 2 mols.

The amount of copper(II)chloride or copper(II) Bromide to be used is from 1 to 5 mols per 1 mol of the compound of the formula [I-3], preferably from 1 to 2 mols.

The solvent to be used may, for example, be an ether such as diethyl ether, tetrahydrofuran or dioxane, a nitrile such as acetonitrile, or an aprotic polar solvent such as N,N-dimethylformamide, N,N-dimethylacetamide, N-methyl-2-pyrrolidone, dimethyl sulfoxide or sulfolane, or a solvent mixture thereof.

The reaction temperature may be optionally selected from a range of from −70° C. to the reflux temperature of the reaction system, and it is preferably within a range of from −20° C. to 100° C. The reaction time varies depending upon the reaction temperature, the reaction substrate, the reaction amount, etc., and it is usually from 10 minutes to 20 hours.

A compound of the formula [I-5b] can be produced by reacting a compound of the formula [I-5a] with methyl mercaptan or 4-methylbenzenethiol in the presence of a base in a solvent.

The base to be used in this reaction may, for example, be an inorganic base such as a hydroxide of an alkali metal such as sodium hydroxide or potassium hydroxide, a hydroxide of an alkaline earth metal such as calcium hydroxide or magnesium hydroxide, a carbonate of an alkali metal such as sodium carbonate or potassium carbonate, or a bicarbonate of an alkali metal such as sodium hydrogencarbonate or potassium hydrogencarbonate, a metal hydride such as sodium hydride or potassium hydride, a metal salt of an alcohol such as sodium methoxide, sodium ethoxide or potassium tert-butoxide, or an organic base such as triethylamine, N,N-dimethylaniline, pyridine, 4-N,N-dimethylaminopyridine or 1,8-diazabicyclo[5.4.0]-7-undecene.

The solvent to be used in this step may, for example, be an ether such as diethyl ether, tetrahydrofuran or dioxane, an aromatic hydrocarbon such as benzene, toluene, xylene or chlorobenzene, an aprotic polar solvent such as N,N-dimethylformamide, N,N-dimethylacetamide, N-methyl-2-pyrrolidone, dimethyl sulfoxide or sulfolane, an alcohol such as methanol, ethanol or isopropyl alcohol, a halogenated hydrocarbon such as methylene chloride, chloroform or dichloroethane, an aliphatic hydrocarbon such as pentane, hexane, cyclohexane or heptane, a ketone such as acetone, methyl ethyl ketone or cyclohexanone, or water.

A compound of the formula [I-5c] or [1-5d] can be produced by reacting a compound of the formula [I-5b] with an oxidizing agent such as hydrogen peroxide, m-chloroperbenzoic acid, sodium periodate, OXONE (tradename, manufactured by E.I. du Pont, containing potassium hydrogenperoxosulfate), N-chlorosuccinimide, N-bromosuccinimide, tert-butyl hypochlorite or sodium hypochlorite.

The amount of the oxidizing agent to be used is, in a case of producing the compound [I-5c], from 0.5 to 1.5 mols, preferably from 0.8 to 1.2 mols, per 1 mol of the compound of the formula [I-5b]. Further, in a case of producing the compound [I-5d], it is from 2 to 10 mols, preferably from 2 mols to 4 mols, per 1 mol of the compound of the formula [I-5b].

The solvent to be used, the reaction temperature and the reaction time are as defined for the above Production Process 10.

Further, a compound of the formula [I-5d] can be produced also by reacting a compound represented by the formula [I-5a] with a methanesulfonic acid salt or a p-toluenesulfinic acid salt.

The amount of the methanesulfonic acid salt or the p-toluenesulfinic acid salt to be used is from 1 to 10 mols, preferably from 1 to 5 mols, more preferably from 1 to 3 mols, per 1 mol of the compound of the formula [I-5a].

The solvent to be used may, for example, be a nitrile such as acetonitrile, or an aprotic polar solvent such as dimethyl sulfoxide, N,N-dimethylformamide or N,N-dimethylacetamide.

The reaction temperature may be optionally selected from a range of from −0° C. to the reflux temperature of the reaction system, and it is preferably within a range of from 10° C. to 100° C.

The reaction time varies depending upon the reaction temperature, the reaction substrate, the reaction amount, etc., and it is usually from 1 to 24 hours.

A compound of the formula [I-5e] can be produced by reacting a compound of the formula [I-3] with a nitrite ester such as t-butyl nitrite or isoamyl nitrite.

The amount of the nitrite ester to be used is from 1 to 5 mols per 1 mol of the compound of the formula [I-3], and it is preferably from 1 to 2 mols.

The solvent to be used may, for example, be an ether such as diethyl ether, tetrahydrofuran or dioxane, a nitrite such as acetonitrile, or an aprotic polar solvent such as N,N-dimethylformamide, N,N-dimethylacetamide, N-methyl-2-pyrrolidone, dimethyl sulfoxide or sulfolane, or a solvent mixture thereof.

The reaction temperature may be optionally selected from a range of from −70° C. to the reflux temperature of the reaction system, and it is preferably within a range of from −20° C. to 100° C. The reaction time varies depending upon the reaction temperature, the reaction substrate, the reaction amount, etc., and it is usually from 10 minutes to 20 hours.

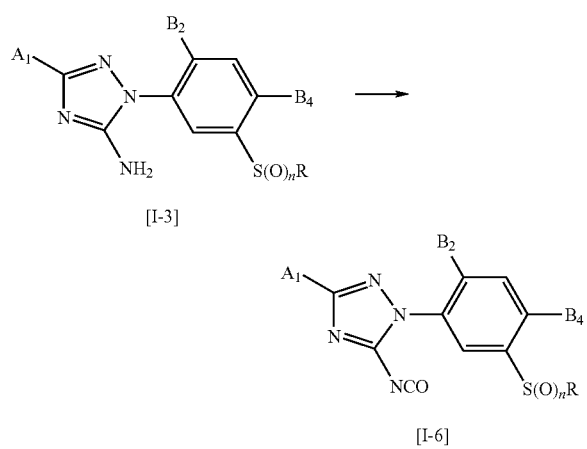

wherein $A_1$, $A_3$, $B_2$, $B_4$, n and R are as defined above.

A compound represented by the formula [I-6] can be produced by a known process by reacting a compound represented by the formula [I-3] with oxalyl chloride or phosgene in the presence of a solvent.

The amount of oxalyl chloride or phosgene to be used may suitably be selected from a range of from 1 mol to the same amount as the amount of the reaction solvent per 1 mol of the compound represented by the formula [I-3], and it is preferably from 1.1 to 3 mols.

The solvent to be used may, for example, be an ether such as diethyl ether, tetrahydrofuran or dioxane, an aromatic hydrocarbon such as benzene, toluene, xylene or chlorobenzene, a halogenated hydrocarbon such as dichloromethane, chloroform or dichloroethane, an aliphatic hydrocarbon such as pentane, hexane, cyclohexane or heptane, or a solvent mixture thereof.

When a compound of the present invention is used as the active ingredient of a pesticide, it may be used by itself. However, it can be formulated into various formulations such as an emulsifiable concentrate, a suspension, a dust, a granule, a tablet, a wettable powder, a water-soluble concentrate, a solution, a flowable suspension, a water dispersible granule, an aerosol, a paste, an oil formulation, a concentrated emulsion in water and a smoking agent in combination with various carriers, surfactants and other adjuvants which are commonly used for formulation as agricultural adjuvants. They are blended usually in such proportions that the active ingredient is from 0.1 to 90 wt % and the agricultural adjuvants are from 10 to 99.9 wt %.

The carriers to be used for such formulation may be classified into solid carriers and liquid carriers. The solid carriers include, for example, animal and plant powders such as starch, activated carbon, soybean powder, wheat flour, wood flour, fish flour and powdered milk, and mineral powders such as talc, kaolin, bentonite, calcium carbonate, zeolite, diatomaceous earth, white carbon, clay, alumina, ammonium sulfate and urea. The liquid carriers include, for example, water; alcohols such as isopropyl alcohol and ethylene glycol; ketones such as cyclohexanone and methyl ethyl ketone; ethers such as dioxane and tetrahydrofuran; aliphatic hydrocarbons such as kerosene and light oil; aromatic hydrocarbons such as xylene, trimethylbenzene, tetramethylbenzene, methylnaphthalene and solvent naphtha; halogenated hydrocarbons such as chlorobenzene; acid amides such as dimethylacetamide; esters such as glycerin esters of fatty acids; nitrites such as acetonitrile; and sulfur-containing compounds such as dimethyl sulfoxide.

The surfactants include, for example, metal salts of alkylbenzenesulfonic acids, metal salts of dinaphthylmethanedisulfonic acids, salts of alcohol sulfates, alkylarylsulfonates, lignin sulfonates, polyoxyethylene glycol ethers, polyoxyethylene alkyl aryl ethers, and polyoxyethylene sorbitan monoalkylates.

The other adjuvants include, for example, adhesive agents and thickeners such as carboxymethylcellulose, gum arabic, sodium arginate, guar gum, tragacanth gum, and polyvinyl alcohol, antifoaming agents such as metal soap, physical property improvers such as fatty acids, alkyl phosphate salts, silicone and paraffin and coloring agents.

When these formulations are practically used, they may be used directly or after diluted with a diluent such as water to a predetermined concentration. Various formulations containing the compounds of the present invention, whether diluted or not, may be applied by conventional methods, i.e., application methods (such as spraying, misting, atomizing, dusting, granule application, paddy water application and seeding box application), soil treatment (such as mixing or drenching), surface application (such as painting, dressing and covering), dipping, poison bait or smoking. Further, the above active ingredients may be incorporated into livestock feeds so as to prevent infestation or growth of pest, especially pest insects after they are voided in excrement. Otherwise, they can also be applied in low volume at high concentration, when the active ingredient may be contained up to 100%. The proportion of the active ingredient is suitably selected if necessary, and it is properly from 0.1 to 20% (by weight) in the case of a dust or a granule, and from 1 to 80% (by weight) in the case of an emulsifiable concentrate or a wettable powder.

The pesticides of the present invention are applied, when they are diluted with a diluent, usually at an active ingredient concentration of from 0.1 to 5,000 ppm. When they are used directly, the dose per unit area is from 0.1 to 5,000 g per 1 ha in terms of the compound that serves as the active ingredient. However, the dose is not limited to such specific range.

The compounds of the present invention are sufficiently effective when used alone. However, they may be used, if necessary, in combination or in admixture with fertilizers or other agrochemicals such as insecticides, miticides, nematicides, fungicides, antivirus agents, attractants, herbicides and plant growth regulators, and such combined use can sometimes produce improved effects.

Typical examples of the insecticides, fungicides, miticides and the like which may be used in combination with the compounds of the present invention, will be given below.

Organophosphorus compounds and carbamate insecticides: fenthion, fenitrothion, diazinon, chlorpyriphos, oxydeprofos, vamidothion, phenthoate (fentoat), dimethoate, formothion, malathion, trichlorphon, thiometon, phosmet, dichlorvos, acephate, EPBP, methyl-parathion, oxydimetonmethyl, ethion, dioxabenzofos, cyanophos (cyanofos), isoxathion, pyridafenthion, phosalone, metidation, sulprophos (sulprofos), chlorfenvinphos, tetrachlorvinphos, dimethylvinphos, propaphos, isofenphos, disulfoton, profenofos, pyraclofos, monocrotophos, azinphos-methyl, aldicarb, methomyl, thiodicarb, carbofuran, carbosulfan, benfuracarb, furathiocarb, propoxur, fenobucarb, metolcarb, isoprocarb, carbaryl (carbaril), pirimicarb, ethiofencarb, dichlophenthion, pirimiphos-methyl, quinalphos, chlorpyriphosmethyl, prothiophos, naled, EPN, XMC, bendiocarb, oxamyl, alanycarb, chlorethoxyfos, etc.

Pyrethroid insecticides: permethrin, cypermethrin, deltamethrin, fenvalerate, fenpropathrin, piretrine, allethrin, tetramethrin, resmethrin, dimethrin, proparthrin, phenothrin, prothrin, fluvalinate, cyfluthrin, cyhalothrin, flucythrinate, etofenprox, cycloprothrin, tralomethrin, silafluofen, tefluthrin, bifenthrin, acrinathrin, etc.

Acylurea type and other insecticides: diflubenzuron, chlorfluazuron, hexaflumuron, triflumuron, teflubenzuron, flufenoksuron, flucycloxuron, buprofezin, pyriproxyfen, lufenuron, cyromazine, methoprene, endosulphan, diafenthiuron, imidacloprid, acetamiprid, nitenpyram, clothianidin, dinotefuran, thiamethoxam, thiacloprid, pymetrozine, fipronil, pyridalyl, nicotin-sulfate, rotenone, metaldehyde, machine oil, microbial pesticides such as BT and entomopathogenic viruses, fenoxycarb, cartap, thiocyclam, bensultap, tebufenozide, chlorphenapyr, emamectin-benzoate, acetaprid, nitenpyram, sodium oleate, rapeseed oil, etc.

Nematicides: phenamiphos, fosthiazate, ethoprophos, methyl isothiocyanate, 1,3-dichloropropene, DCIP, etc.

Miticides: chlororbenzilate, phenisobromolate, dicofol, amitraz, propargit, benzomate, hexythiazox, fenbutatin oxide, polynactin, quinomethionate, chlorfenson, tetradifon, avermectin, milbemectin, clofentezine, pyridaben, fenpyroximate, tebufenpyrad, pyrimidifen, fenothiocarb, dienochlor, etoxazole, bifenazate, acequinocyl, halfenprox, spirodiclofen, etc.

Fungicides: thiophanate-methyl, benomil, carbendazol, thiabendazol, folpet, thiuram, diram, zineb, maneb, polycarbamate, iprobenfos, edifenphos, fthalide, probenazole, isoprothiolane, chlorothalonil, captan, polyoxin, blasticidin-S, kasugamycin, streptomycin, validamycin, tricyclazole, pyroquilon, phenazine oxide, mepronil, flutolanil, pencycuron, iprodione, hymexazol, metalaxyl, triflumizole, triforine, triadimefon, bitertanol, fenarimol, propikonazol, cymoxanil, prochloraz, pefurazoate, hexaconazole, myclobutanil, diclomezine, tecloftalam, propineb, dithianon, phosethyl, vinclozolin, procymidone, oxadixyl, guazatine, propamocarb-hydrochloride, fluazinam, oxolinic acid, hydroxyisoxazole, mepanipyrim.

The compounds of the present invention exhibit excellent pesticidal activities against pests such as pest hemiptera, pest lepidoptera, pest coleoptera, pest diptera, pest hymenoptera, pest orthoptera, pest isoptera, pest thysanoptera, mites and plant-parasitic nematodes. The following pest insects may be mentioned as such pests.

Pest hemiptera: bugs (HETEROPTERA) such as bean bug (*Riptortus clavatus*), southern green stink bug (*Nezara viridula*), lygus bugs (*Lygus* sp.), hairy chinch bug (*Blissus leucopterus*) and pear lace bug (*Stephanitis nashi*); leafhoppers (Deltocephalinae) such as green rice leafhopper (*Nephotettix cincticeps*) and leafhoppers (*Empoasca* sp., *Erythroneura* sp., *Circulifer* sp.); delphacid planthoppers such as brown rice planthopper (*Nilaparvata lugens*), white-backed planthopper (*Sogatella furcifera*) and small brown planthopper (*Laodelphax striatellus*); jumping plantlice such as Psyllids (*Psylla* sp.); whiteflies such as silverleaf whitefly (*Bemisia tabaci*) and greenhouse whitefly (*Trialeurodes vaporariorum*); aphides such as grapeleaf louse (*Viteus vitifolii*), green peach aphid (*Myzus persicae*), green apple aphid (*Aphis pomi*), cotton aphid (*Aphis gossypii*), *Aphis fabae*, turnip aphid (*Rhopalosiphum psedobrassicas*), glasshouse-potato aphid (*Aulacorthum solani*) and greenbug (*Schizaphis graminum*); mealy bugs or scales such as Comstock mealybug (*Pseudococcus comstocki*), red wax scale (*Ceroplastes rubens*), San Jose scale (*Comstockaspis perniciosa*) and arrowhead scale (*Unaspis yanonensis*) and assassin bugs (*Rhodinius* sp.).

Pest lepidoptera: tortricids such as oriental tea tortrix (*Homona magnanima*), summer fruit tortrix (*Adoxophyes orana*), tortricids (*Sparganothis pilleriana*), oriental fruit moth (*Grapholitha molesta*), soybean pod borer (*Leguminivora glycinivorella*), codling moth (*Laspeyresia pomonella*), *Eucosma* sp. and *Lobesia botrana*; Cochylidae such as grape cochylid (*Eupoecillia ambiguella*); bagworm moths such as *Bambalina* sp.; tineids such as European grain moth (*Nemapogon granellus*) and casemaking clothes moth (*Tinea translucens*); lyonetid moths such as *Lyonetia prunifoliella*; leafblotch miners such as apple leafminer (*Phyllonorycter rigoniella*); Phyllocnistidae such as citrus leafminer (*Phyllocnistis citrella*); yponomeutids such as diamondback moth (*Plutella xylostella*) and Prays citri; clearwing moths such as grape clearwing moth (*Paranthrene regalis*) and *Synanthedon* sp.; gelechiid moths such as pink bollworm (*Pectinophora gossypiella*), potato tuberworm (*Phthorimaea operculella*) and *Stomopteryx* sp.; Carposinidae such as peach fruit moth (*Carposina niponensis*); slug caterpillarmoths such as oriental moth (*Monema flavescens*); pyralid moths such as Asiatic rice borer (*Chilo suppressalis*), rice leafroller (*Cnaphalocrocis medinalis*), *Ostrinia nubilalis*, oriental corn borer (*Ostrinia furnacalis*), cabbage webworm (*Hellula undalis*), greater wax moth (*Galleria mellonella*), *Elasmopalpus lignosellus* and *Loxostege sticticalis*; whites such as common cabbageworm (*Pieris rapae*); geometrid moths such as mugwort looper (*Ascotis selenaria*); tent caterpillar moths such as tent caterpillar (*Malacosoma neustria*); sphinx moths such as *Manduca sexta*; tussock moths such as tea tussock moth (*Euproctis pseudoconspersa*) and gypsy moth (*Lymantria dispar*); tiger moths such as fall webworm (*Hyphantria cunea*); and owlet moths such as tobacco budworm (*Heliothis virescens*), bollworm (*Helicoverpa zea*), beet armyworm (*Spodoptera exigua*), cotton bollworm (*Helicoverpa armigera*), common cutworm (*Spodoptera litura*), cabbage armyworm (*Mamestra brassicae*), black cutworm (*Agrotis ipsiron*), rice armyworm (*Pseudaletia separata*) and cabbage looper (*Trichoplusia ni*).

Pest coleoptera: chafers such as cupreous chafer (*Anomala cuprea*), Japanese beetle (*Popillia japonica*), soybean beetle (*Anomala rufocuprea*) and Eutheola rugiceps; click beetles such as wireworm (*Agriotes* sp.) and *Conodeus* sp.; ladybirds such as twenty-eight-spotted ladybird (*Epilachna vigintioctopunctata*) and Mexican bean beetle (*Epilachna varivestis*); darkling beetles such as red flour beetle (*Tribolium castaneum*); longicorn beetles such as white-spotted longicorn beetle (*Anoplophora malasiaca*) and pine sawyer (*Monochamus alternatus*); seed beetles such as bean weevil (*Acanthoscelides obtectus*) and adzuki bean weevil (*Callosobru-* chus chinensis); leaf beetles such as colorado potato beetle (*Leptinotarsa decemlineata*), corn rootworm (*Diabrotica* sp.), rice leaf beetle (*Oulema oryzae*), beet flea beetle (*Chaetocnema concinna*), *Phaedon cochlearias*, *Oulema melanopus* and *Dicladispa armigera*; Apionidae such as *Apion godmani*; weevils such as rice water weevil (*Lissorhoptrus oryzophilus*) and cotton boll weevil (*Anthonomus grandis*); Rhynchophoridae such as maize weevil (*Sitophilus zeamais*); bark beetles; dermestid beetles; and drugstore beetles.

Pet diptera: rice crane fly (*Tipra ano*), rice midge (*Tanytarsus oryzae*), gall midge (*Orseolia oryzae*), medfly (*Ceratitis capitata*), rice leafminer (*Hydrellia griseola*), cherry drosophila (*Drosophila suzukii*), frit fly (*Oscinella frit*), rice stem maggot (*Chlorops oryzae*), French bean miner (*Ophiomyia phaseoli*), legume leafminer (*Liriomyza trifolii*), spinach leafminer (*Pegomya hyoscyami*), seedcorn maggot (*Hylemia platura*), sorghum fly (*Atherigona soccata*), muscid fly (*Musca domestica*), horse bot-flies (*Gastrophilus* sp.), stable flies (*Stomoxys* sp.), yellow fever mosquito (*Aedes aegypti*), nrothern house mosquito (*Culex pipiens*), malaria mosquito (*Anopheles slnensis*) and *Culex tritaeniorhynchus*.

Pest hymenoptera: stem sawflies (*Cephus* sp.); eurytomids (*Harmolita* sp.); cabbage sawflies (*Athalia* sp.), hornets (*Vespa* sp.) and fire ants.

Pest orthoptera: German cockroach (*Blatella germanica*); American cockroach (*Periplaneta americana*); African mole cricket (*Gryllotalpa africana*); Asiatic locust (*Locusta migratoria migratoriodes*); and *Melanoplus sanguinipes*.

Pest isoptera: termites (*Reticulitermes speratus*) and Formosan subterranean termite (*Coptotermes formosanus*).

Pest thysanopetra: yellow tea thrips (*Scirtothrips dorsalis*); melon thrips (*Thrips palmi*); greenhouse thrips (*Heliothrips haemorrholidalis*); western flower thrips (*Frankliniella occidentalis*) and rice aculeated thrips (*Haplothrips aculeatus*).

Mites: two-spotted spider mite (*Tetranychus urticae*); Kanazawa spider mite (*Tetranychus kanzawai*); citrus red mite (*Panonychus citri*); European red mite (*Panonychus ulmi*), yellow spider mite (*Eotetranychus carpini*); Texas citrus mite (*Eotetranychus banksi*); citrus rust mite (*Phyllocoptruta oleivora*); broad mite (*Polyphagotarsonemus latus*); false spider mites (*Brevipalpus* sp.); bulb mite (*Rhizoglyphus robini*) and mold mite (*Tyrophagus putrescentiae*).

Plant-parasitic nematodes: root-knot nematode (*Meloidogyne* sp.); root-lesion nematode (*Pratylenchus* sp.); soybean cyst nematode (*Heterodera glycines*); golden nematode (*Globodera rostochiensis*); banana burrowing nematode (*Radopholus similis*); strawberry bud nematode (*Aphelenchoides fragariae*); rice white-tip nematode (*Aphelenchoides besseyi*) and pine wood nematode (*Bursaphelenchus xylophilus*).

Other pests, unfavorable animals, insanitary insects, and parasites: gastropods (Gastropoda) such as apple snails (*Pomacea canaliculata*), slugs (*Incilaria* sp.) and giant African snail (*Achatina fulica*); isopods (*Isopoda*) such as pillbug (*Armadillidium* sp.), sow bug and centipede; booklice such as *Liposcelis* sp.; silverfish such as *Ctenolepisma* sp.; fleas such as *Pulex* sp. and *Ctenocephalides* sp.; bird lice such as *Trichodectes* sp.; bed bugs such as *Cimex* sp.; animal-parasitic mites such as *Boophilus microplus* and *Haemaphysalis longicornis* and Epidermoptidae.

Further, the compounds of the present invention are effective also against pest insects which show resistance to organophosphorus compounds, carbamate compounds, synthetic pyrethroid compounds, acylurea compounds or conventional insecticides.

EXAMPLES

Now, preparation, formulations and use of the compounds of the present invention will be described in further detail with reference to Examples. Preparations of synthetic intermediates of the compounds of the present invention will also be described.

Example 1

Preparation of [5-(5-amino-3-trifluoromethyl-1,2,4-triazolyl)-4-chloro-2-methylphenyl]2,2,2-trifluoroethyl sulfide Compound No. 7 of the Present Invention (1) Synthesis of 5-acetylthio-2-chloro-4-methylacetanilide 55 g of 2-chloro-4-methylacetanilide was added to 100 ml of chlorosulfonic acid at from 5 to 10° C. 65 g of 60% fuming sulfuric acid was added to the mixed liquid at from 10 to 15° C., and the resulting mixture was stirred at room temperature for 1 hour and further stirred at 90° C. for 18 hours. After the resulting reaction mixture was cooled to room temperature, it was poured into ice water, toluene was added, the insolubles were filtered off, and the resulting organic layer was washed with water and dried over anhydrous magnesium sulfate. The solvent was distilled off under reduced pressure, and a mixture of the obtained residue, 31 g of red phosphorus, 1 g of iodine and 200 ml of acetic acid was refluxed with heating for 1 hour, and the obtained reaction liquid was cooled to room temperature. After the insolubles were filtered off, the liquid was concentrated under reduced pressure, water was added, and extraction with ethyl acetate was carried out. The organic layer was washed with water and dried over anhydrous magnesium sulfate, the solvent was distilled off under reduced pressure, and the residue was purified by silica gel column chromatography to obtain 14 g of 5-acetylthio-2-chloro-4-methylacetanilide.

(2) Synthesis of 2-chloro-4-methyl-5-mercaptoaniline 14 g of 5-acetylthio-2-chloro-4-methylacetanilide was dissolved in 150 ml of ethanol, and 22 g of a 50% aqueous sodium hydroxide solution was added, followed by reflux with heating for 4 hours. The obtained reaction mixture was concentrated under reduced pressure, water was added, and the mixture was neutralized with diluted hydrochloric acid and then extracted with ethyl acetate. The organic layer was washed with water and dried over anhydrous magnesium sulfate, and the solvent was distilled off under reduced pressure to obtain 9.4 g of 2-chloro-4-methyl-5-mercaptoaniline.

(3) Synthesis of 2-chloro-4-methyl-5-(2,2,2-trifluoroethylthio)aniline

A mixture of 9.4 g of 2-chloro-4-methyl-5-mercaptoaniline, 20 g of 2,2,2-trifluoroethyl iodide, 13 g of potassium carbonate and 200 ml of N,N-dimethylformamide was stirred at room temperature for 16 hours. The reaction mixture was concentrated under reduced pressure, water was added, and the mixture was extracted with toluene. The organic layer was washed with water and dried over anhydrous magnesium sulfate, and the solvent was distilled off under reduced pressure to obtain 13.5 g of 2-chloro-4-methyl-5-(2,2,2-trifluoroethylthio)aniline.

$^1$H-NMR data (CDCl$_3$/TMS δ (ppm) value): 2.32 (3H, s), 3.33 (2H, q), 3.96 (2H, s), 6.94 (1H, s), 7.11 (1H, s)

(4) Synthesis of 2-chloro-4-methyl-5-(2,2,2-trifluoroethylthio)phenylhydrazine 13.5 g of 2-chloro-4-methyl-5-(2,2,2-trifluoroethylthio) aniline was added dropwise to 30 ml of concentrated hydrochloric acid at room temperature, and to this mixture, an aqueous solution containing 3.8 g of sodium nitrite was added dropwise at from 0 to 5° C., and the mixture was stirred as it was for 1 hour to prepare a diazonium salt. 36 g of tin chloride dihydrate was dissolved in 250 ml of 6N hydrochloric acid, and to this mixed solution, the above aqueous diazonium salt solution was added dropwise at from 0 to 5° C., and the solution was further stirred at room temperature for 2 hours. Toluene was added, the solution was neutralized with an aqueous sodium hydroxide solution, the insolubles were filtered off, and the organic layer was washed with water and dried over anhydrous magnesium sulfate. The solvent was distilled off under reduced pressure to obtain 12.1 g of 2-chloro-4-methyl-5-(2,2,2-trifluoroethylthio)phenylhydrazine.

(5) Synthesis of trifluoroacetaldehyde {2-chloro-4-methyl-5-(2,2,2-trifluoroethylthio)phenyl}hydrazone A mixture of 4.1 g of 2-chloro-4-methyl-5-(2,2,2-trifluoroethylthio)phenylhydrazine, 2.3 g of trifluoroacetaldehyde ethyl hemiacetal, 0.1 g of p-toluenesulfonic acid monohydrate and 50 ml of ethanol was refluxed with heating for 6 hours. The obtained reaction mixture was concentrated under reduced pressure, water was added, and the mixture was extracted with toluene. The organic layer was washed with water and dried over anhydrous magnesium sulfate, and the solvent was distilled off under reduced pressure to obtain 3.6 g of trifluoroacetaldehyde {2-chloro-4-methyl-5-(2,2,2-trifluoroethylthio)phenyl}hydrazone.

(6) Synthesis of N-{2-chloro-4-methyl-5-(2,2,2-trifluoroethylthio)phenyl}trifluoroacetohydrazonoyl bromide 3.6 g (10.3 mmol) of trifluoroacetaldehyde {2-chloro-4-methyl-5-(2,2,2-trifluoroethylthio)phenyl}hydrazone was dissolved in 30 ml of N,N-dimethylformamide, and 2.0 g of N-bromosuccinimide was added at room temperature, followed by stirring at room temperature for 2 hours. The resulting reaction mixture was poured into water and extracted with toluene, and the organic layer was washed with water and dried over anhydrous magnesium sulfate. The solvent was distilled off under reduced pressure to obtain 4.1 g of N-{2-chloro-4-methyl-5-(2,2,2-trifluoroethylthio) phenyl}trifluoroacetohydrazonoyl bromide.

(7) Synthesis of [5-(5-amino-3-trifluoromethyl-1,2, 4-triazolyl)-4-chloro-2-methylphenyl]2,2,2-trifluoroethyl sulfide 3.5 g of triethylamine was added at room temperature to a mixture of 4.1 g of N-{2-chloro-4-methyl-5-(2,2,2-trifluoroethylthio)phenyl}trifluoroacetohydrazonoyl bromide, 4.4 g of S-methylisothiourea hydroiodate and 100 ml of tetrahydrofuran, and the mixture was stirred at 50° C. for 3 hours. The reaction mixture was concentrated under reduced pressure, and xylene was added to the obtained residue, followed by reflux with heating for 2 hours. The reaction mixture was cooled to room temperature and then washed with water, and the organic layer was dried over anhydrous magnesium sulfate. The solvent was distilled off under reduced pressure, and the obtained crude crystals were recrystallized from ethanol to obtain 2.0 g of [5-(5-amino-3-trifluoromethyl-1,2,4-triazolyl)-4-chloro-2-methylphenyl]2,2,2-trifluoroethyl sulfide as pale gray crystals (melting point 193 to 194° C.)

Example 2

Preparation of [5-(5-amino-3-trifluoromethyl-1,2,4-triazolyl)-4-chloro-2-methylphenyl]2,2,2-trifluoroethyl sulfoxide Compound No. 8 of the Present Invention 1.3 g of [5-(5-amino-3-trifluoromethyl-1,2,4-triazolyl)-4-chloro-2-methylphenyl]2,2,2-trifluoroethyl sulfide was dissolved in 80 ml of ethyl acetate, and 0.9 g (purity 75%) of m-chloroperbenzoic acid was added under cooling with ice. The mixture was stirred under cooling with ice for 2 hours, washed with an aqueous sodium thiosulfate solution and then washed with an aqueous sodium hydrogencarbonate solution, and then dried over anhydrous magnesium sulfate. The solvent was distilled off under reduced pressure, and the obtained crystals were washed with carbon tetrachloride to obtain 1.2 g of [5-(5-amino-3-trifluoromethyl-1,2,4-triazolyl)-4-chloro-2-methylphenyl]2,2,2-trifluoroethyl sulfoxide as white crystals (melting point 235 to 237° C.).

Example 3

Preparation of [5-(3-nitro-1,2,4-triazolyl)-2-difluoromethylphenyl]2,2,2-trifluoroethyl sulfide Compound No. 11 of the Present Invention (1) Synthesis of 4-(3-nitro-1,2,4-triazolyl)-2-fluorobenzaldehyde 10 ml of a N,N-dimethylformamide solution of 3.4 g of 3-nitro-1,2,4-triazole was added dropwise to a suspension of 1.2 g (60%) of sodium hydride and 50 ml of N,N-dimethylformamide under cooling with ice. After generation of hydrogen stopped, 4.3 g of 2,4-difluorobenzaldehyde was added, followed by stirring at 70° C. for 3 hours. The mixture was concentrated under reduced pressure, 200 ml of water was added, and the mixture was extracted with ethyl acetate. The ethyl acetate layer was washed with water and dried over anhydrous magnesium sulfate. The solvent was distilled off under reduced pressure, and the obtained crude crystals were washed with diisopropyl ether to obtain 1.6 g of 4-(3-nitro-1,2,4-triazolyl)-2-fluorobenzaldehyde.

(2) Synthesis of 4-(3-nitro-1,2,4-triazolyl)-2-(2,2,2-trifluoroethylthio)benzaldehyde 0.8 g of 2,2,2-trifluoroethylmercaptan was added dropwise under cooling with ice to a mixture of 1.6 g of 4-(3-nitro-1, 2,4-triazolyl)-2-fluorobenzaldehyde, 1.3 g of potassium carbonate and 50 ml of N,N-dimethylformamide, followed by stirring at from 0 to 10° C. for 4 hours. The mixture was concentrated under reduced pressure, 200 ml of water was added, and the mixture was extracted with ethyl acetate. The organic layer was washed with water and dried over anhydrous magnesium sulfate. The solvent was distilled off under reduced pressure to obtain 1.8 g of 4-(3-nitro-1,2,4-triazolyl)-2-(2,2,2-trifluoroethylthio)benzaldehyde.

(3) Synthesis of [5-(3-nitro-1,2,4-triazolyl)-2-difluoromethylphenyl]2,2,2-trifluoroethyl sulfide 2.6 g of diethylaminosulfur trifluoride was added under cooling with ice to a mixture of 1.8 g of 4-(3-nitro-1,2,4-triazolyl)-2-(2,2,2-trifluoroethylthio)benzaldehyde with 20 ml of methylene chloride, followed by reflux with heating for 6 hours. After the mixture was cooled to room temperature, it was poured into ice water, and the organic layer was washed with an aqueous sodium hydrogencarbonate solution and with water and then dried over anhydrous magnesium sulfate. The solvent was distilled off under reduced pressure, and the residue was purified by silica gel column chromatography to obtain [5-(3-nitro-1,2,4-triazolyl)-2-difluoromethylphenyl]-2,2,2-trifluoroethyl sulfide as pale yellow crystals (melting point 74 to 76° C.)

Example 4

Preparation of [5-(5-amino-3-trifluoromethyl-1,2,4-triazolyl)-4-fluoro-2-methylphenyl]2,2,2-trifluoroethyl sulfide Compound No. 1 of the Present Invention (1) Synthesis of 5-acetylthio-2-fluoro-4-methylacetanilide 150 g of 2-fluoro-4-methylacetanilide was added to 500 g of chlorosulfonic acid at 50° C. or lower, followed by stirring for 1 hour. The reaction mixture was poured into a mixture of ice water with ethyl acetate, the organic layer was washed with water and dried over anhydrous magnesium sulfate, and the solvent was distilled off under reduced pressure to obtain solid residue. The obtained solid residue was dissolved in 350 ml of acetic acid, and the obtained solution was added dropwise to a mixture of 84 g of red phosphorus, 1 g of iodine and 300 ml of acetic acid under reflux with heating over a period of 1 hour, followed by reflux with heating for 2 hours. The reaction mixture was cooled to room temperature, the insolubles were filtered off, and the liquid was concentrated under reduced pressure, water was poured, and the mixture was extracted with ethyl acetate. The organic layer was washed with water and dried over anhydrous magnesium sulfate, and the solvent was distilled off under reduced pressure to obtain 211 g of 5-acetylthio-2-fluoro-4-methylacetanilide.

(2) Synthesis of 2-fluoro-4-methyl-5-mercaptoaniline 211 g of 5-acetylthio-2-fluoro-4-methylacetanilide was dissolved in 500 ml of ethanol, and to this solution, a solution comprising 200 g of potassium hydroxide and 500 ml of water was added dropwise over a period of 30 minutes, followed by reflux with heating for 5 hours. After the reaction mixture was cooled to room temperature, it was neutralized with diluted hydrochloric acid, concentrated under reduced pressure and extracted with ethyl acetate. The organic layer was dried over anhydrous magnesium sulfate, and the solvent was distilled off under reduced pressure to obtain 129 g of 2-fluoro-4-methyl-5-mercaptoaniline.

(3) Synthesis of 2-fluoro-4-methyl-5-(2,2,2-trifluoroethylthio)aniline

To 1,000 ml of a N,N-dimethylformamide solution of 129 g of 2-fluoro-4-methyl-5-mercaptoaniline, 250 g of 2,2,2-trifluoroethyl iodide and 125 g of potassium carbonate were added, and 10 g of Rongalit was further added, followed by stirring at room temperature for 8 hours. The reaction liquid was poured into water, the mixture was extracted with ethyl acetate, the organic layer was dried over anhydrous magnesium sulfate, and the solvent was distilled off under reduced pressure to obtain 182 g of 2-fluoro-4-methyl-5-(2,2,2-trifluoroethylthio)aniline.

$^1$H-NMR data (CDCl$_3$/TMS δ (ppm) value): 2.36 (3H, s), 3.30 (2H, q), 3.64 (2H, s), 6.86 (1H, d), 6.98 (1H, d)

(4) Synthesis of 2-fluoro-4-methyl-5-(2,2,2-trifluoroethylthio)phenylhydrazine 53 g of sodium nitrite was added to 300 ml of concentrated sulfuric acid at 50° C. or lower, and 300 ml of acetic acid was added dropwise at 50° C. or lower. To this mixed solution, 100 ml of an acetic acid solution of 182 g of 2-fluoro-4-methyl-5-(2,2,2-trifluoroethylthio)aniline was added dropwise over a period of 2 hours at 20° C. or lower, followed by stirring at 20° C. for 3 hours. The reaction mixture was added dropwise at 5° C. or lower to a mixed solution of 390 g of tin(II)chloride dihydrate and 1,000 ml of 6N hydrochloric acid, followed by stirring for 30 minutes. Toluene was added to this reaction mixture, and the reaction mixture was neutralized with a 10% aqueous sodium hydroxide solution. The insolubles were filtered off, and the organic layer was dried over anhydrous magnesium sulfate and concentrated under reduced pressure to obtain 177 g of 2-fluoro-4-methyl-5-(2,2,2-trifluoroethylthio)phenylhydrazine.

(5) Synthesis of trifluoroacetaldehyde {2-fluoro-4-methyl-5-(2,2,2-trifluoroethylthio)phenyl}hydrazone A mixture of 3.1 g of 2-fluoro-4-methyl-5-(2,2,2-trifluoroethylthio)phenylhydrazine, 1.9 g of trifluoroacetaldehyde ethyl hemiacetal, 0.5 g of methanesulfonic acid and 100 ml of ethanol was refluxed with heating for 5 hours. After the reaction mixture was cooled to room temperature, it was concentrated under reduced pressure and extracted with ethyl acetate, and the organic layer was dried over anhydrous magnesium sulfate. The solvent was distilled off under reduced pressure to obtain 3.7 g of trifluoroacetaldehyde {2-fluoro-4-methyl-5-(2,2,2-trifluoroethylthio)phenyl}hydrazone.

(6) Synthesis of N-{2-fluoro-4-methyl-5-(2,2,2-trifluoroethylthio)phenyl}trifluoroacetohydrazonoyl bromide 3.7 g of trifluoroacetaldehyde {2-fluoro-4-methyl-5-(2,2,2-trifluoroethylthio)phenyl}hydrazone was dissolved in 50 ml of N,N-dimethylformamide, and 2.0 g of N-bromosuccinimide was added at room temperature, followed by stirring at room temperature for 30 minutes. The reaction mixture was poured into water and extracted with ethyl acetate, and the organic layer was dried over anhydrous magnesium sulfate. The solvent was distilled off under reduced pressure to obtain 4.4 g of N-{2-fluoro-4-methyl-5-(2,2,2-trifluoroethylthio) phenyl}trifluoroacetohydrazonoyl bromide.

(7) [5-(5-amino-3-trifluoromethyl-1,2,4-triazolyl)-4-fluoro-2-methylphenyl]2,2,2-trifluoroethyl sulfide To 100 ml of tetrahydrofuran, 4.5 g of S-methylisothiourea hydroiodide, 4.4 g of N-{2-fluoro-4-methyl-5-(2,2,2-trifluoroethylthio)phenyl} trifluoroacetohydrazonoyl bromide and 3.5 g of triethylamine were added, followed by reflux with heating for 8 hours. After the reaction mixture was cooled to room temperature, it was concentrated under reduced pressure and extracted with ethyl acetate, and the organic layer was washed with water and dried over anhydrous magnesium sulfate. The solvent was distilled off under reduced pressure, and the obtained solid was purified by column chromatography (eluent ethyl acetate:hexane=4:1) to obtain 2.9 g of [5-(5-amino-3-trifluoromethyl-1,2,4-triazolyl)-4-fluoro-2-methylphenyl]2,2,2-trifluoroethyl sulfide as pale yellow crystals (melting point 171 to 173° C.).

Example 5

Preparation of [5-(5-amino-3-trifluoromethyl-1,2,4-triazolyl)-4-fluoro-2-methylphenyl]2,2,2-trifluoroethyl sulfoxide Compound No. 2 of the Present Invention 1.9 g of [5-(5-amino-3-trifluoromethyl-1,2,4-triazolyl)-4-fluoro-2-methylphenyl]2,2,2-trifluoroethyl sulfide was dissolved in 100 ml of chloroform, and 1.0 g of m-chloroperbenzoic acid was added at 0° C., followed by stirring at room temperature for 1 hour. The solvent was distilled off under reduced pressure and the obtained residue was purified by column chromatography (eluent ethyl acetate:hexane:triethylamine=50:50:1) to obtain 1.8 g of [5-(5-amino-3-trifluoromethyl-1,2,4-triazolyl)-4-fluoro-2-methylphenyl]2,2,2-trifluoroethyl sulfoxide as pale yellow crystals (melting point 236 to 238° C.).

Example 6

Preparation of [5-(5-trifluoroacetylamino-3-trifluoromethyl-1,2,4-triazolyl)-4-fluoro-2-methylphenyl]2,2,2-trifluoroethyl sulfide Compound No. 5 of the Present Invention 1.1 g of [5-(5-amino-3-trifluoromethyl-1,2,4-triazolyl)-4-fluoro-2-methylphenyl]2,2,2-trifluoroethyl sulfide was added to 50 ml of trifluoroacetic anhydride, followed by stirring at room temperature for 12 hours. The solvent was distilled off under reduced pressure, and the obtained solid was purified by column chromatography (eluent ethyl acetate:hexane=2:1) to obtain 1.1 g of [5-(5-trifluoroacetylamino-3-trifluoromethyl-1,2,4-triazolyl)-4-fluoro-2-methylphenyl]2,2,2-trifluoroethyl sulfide as pale yellow crystals (melting point 122 to 125° C.)

Example 7

Preparation of [5-(5-amino-3-trifluoromethyl-1,2,4-triazolyl)-4-fluoro-2-methylphenyl]2,2,2-trifluoroethyl sulfoxide Compound No. 6 of the Present Invention 0.8 g of [5-(5-trifluoroacetylamino-3-trifluoromethyl-1,2,4-triazolyl)-4-fluoro-2-methylphenyl]2,2,2-trifluoroethyl sulfide was dissolved in 50 ml of chloroform, and 0.3 g of m-chloroperbenzoic acid was added at 0° C., followed by stirring at room temperature for 1 hour. The solvent was distilled off under reduced pressure, and the obtained solid was purified by column chromatography (eluent ethyl acetate:hexane=1:1) to obtain 0.6 g of [5-(5-trifluoroacetylamino-3-trifluoromethyl-1,2,4-triazolyl)-4-fluoro-2-methylphenyl]2,2,2-trifluoroethyl sulfoxide as a pale yellow powder (melting point 233 to 237° C.).

The structural formulae and physical properties of the compounds [I] of the present invention synthesized in accordance with the above Examples, including the above Examples, are shown in Tables 7 to 10. The symbols in the Tables denote as defined above.

The compound numbers will be referred to in the subsequent description.

TABLE 7

| Compound No. | m.p. (° C.) or refractive indx | $(n_D^{20})$ |
|---|---|---|
| 1 | m.p. | 171-173 |
| 2 | m.p. | 236-238 |
| 3 | m.p. | 179-181 |
| 4 | m.p. | 207-209 |
| 5 | m.p. | 122-125 |
| 6 | m.p. | 233-237 |
| 7 | m.p. | 193-194 |
| 8 | m.p. | 235-237 |
| 9 | m.p. | 183-185 |
| 10 | m.p. | 249-251 |
| 11 | m.p. | 74-76 |
| 12 | m.p. | 155-156 |
| 15 | m.p. | 130-131 |
| 17 | m.p. | 158-160 |
| 18 | m.p. | 181-183 |
| 20 | m.p. | 218-219 |
| 21 | m.p. | 87-89 |
| 23 | m.p. | 156-157 |
| 24 | m.p. | 201-203 |
| 26 | m.p. | 204-205 |
| 27 | m.p. | 107-109 |
| 28 | m.p. | 189-191 |
| 30 | m.p. | 199-202 |
| 31 | m.p. | 111-113 |
| 32 | m.p. | 205-207 |
| 35 | m.p. | 130-131 |
| 36 | m.p. | 184-186 |
| 37 | m.p. | 120-122 |
| 38 | m.p. | 196-198 |
| 39 | m.p. | 150-151 |
| 40 | m.p. | 147-148 |
| 43 | m.p. | 111-114 |
| 49 | m.p. | unmeasurable |
| 50 | m.p. | 195-197 |
| 55 | m.p. | 176-178 |
| 56 | m.p. | 256-257 |
| 59 | refractive index | 1.4988 |
| 60 | m.p. | 149-152 |
| 65 | m.p. | 76-78 |
| 66 | m.p. | 152-154 |

TABLE 8

| Compound No. | m.p. (° C.) or refractive indx | $(n_D^{20})$ |
|---|---|---|
| 75 | m.p. | 133-135 |
| 76 | m.p. | 159-161 |
| 79 | m.p. | 131-133 |
| 80 | m.p. | 167-169 |
| 83 | m.p. | 142-144 |
| 84 | m.p. | 100-103 |
| 97 | m.p. | 116-118 |
| 98 | m.p. | 181-182 |
| 99 | m.p. | 180-181 |
| 101 | refractive index | 1.5028 |

TABLE 8-continued

| Compound No. | m.p. (° C.) or refractive indx | $(n_D^{20})$ |
|---|---|---|
| 102 | m.p. | 141-143 |
| 103 | m.p. | 156-157 |
| 104 | m.p. | 194-195 |
| 105 | m.p. | 171-172 |
| 106 | m.p. | 180-182 |
| 106 | m.p. | 138-139 |
| 107 | m.p. | 185-186 |
| 108 | m.p. | 157-159 |
| 110 | m.p. | 149-151 |
| 111 | m.p. | 146-148 |
| 112 | m.p. | 170-172 |
| 113 | m.p. | 156-157 |
| 114 | m.p. | 125-128 |
| 115 | m.p. | 147-150 |
| 116 | m.p. | 169-172 |
| 117 | m.p. | 199-200 |
| 118 | m.p. | 140-142 |
| 119 | m.p. | 154-156 |
| 120 | m.p. | 163-165 |
| 121 | m.p. | 204-206 |
| 123 | m.p. | 205-206 |
| 124 | m.p. | 135-137 |
| 125 | m.p. | 207-208 |
| 126 | m.p. | 147-149 |
| 127 | m.p. | 164-167 |
| 128 | refractive index | 1.4811 |
| 130 | m.p. | 109-110 |
| 131 | m.p. | 152-154 |
| 133 | m.p. | 195-197 |
| 134 | m.p. | 81-84 |
| 136 | m.p. | 140-141 |
| 137 | m.p. | 196-197 |
| 139 | m.p. | 198-199 |
| 140 | m.p. | 110-111 |
| 141 | m.p. | 138-140 |

TABLE 9

| Compound No. | m.p. (° C.) or refractive indx | $(n_D^{20})$ |
|---|---|---|
| 143 | m.p. | 193-195 |
| 144 | m.p. | 49-51 |
| 145 | m.p. | 102-104 |
| 146 | m.p. | 91-93 |
| 147 | m.p. | 203-205 |
| 148 | m.p. | 69-71 |
| 150 | m.p. | 127-128 |
| 151 | m.p. | 92-95 |
| 153 | m.p. | 147-149 |
| 154 | m.p. | 147-149 |
| 155 | m.p. | 163-166 |
| 157 | m.p. | 89-92 |
| 158 | refractive index | 1.5175 |
| 160 | m.p. | 91-93 |
| 161 | m.p. | 50-53 |
| 162 | m.p. | 113-115 |
| 163 | m.p. | 195-197 |
| 164 | m.p. | 112-114 |
| 165 | m.p. | 130-132 |
| 167 | m.p. | 93-95 |
| 168 | m.p. | 132-133 |
| 169 | m.p. | 107-109 |
| 170 | m.p. | 53-55 |
| 171 | m.p. | 138-139 |
| 172 | m.p. | 102-104 |
| 173 | m.p. | 208-211 |
| 174 | m.p. | 97-98 |
| 175 | m.p. | 193-195 |
| 176 | m.p. | 113-115 |
| 177 | m.p. | 209-211 |
| 178 | m.p. | 178-179 |
| 179 | m.p. | 206-208 |
| 180 | m.p. | 159-160 |
| 181 | m.p. | 89-92 |

TABLE 9-continued

| Compound No. | m.p. (° C.) or refractive indx | $(n_D^{20})$ |
|---|---|---|
| 182 | m.p. | 159-161 |
| 183 | m.p. | 107-110 |
| 184 | refractive index | 1.5253 |
| 185 | refractive index | 1.5335 |
| 186 | m.p. | 115-116 |
| 187 | m.p. | 139-141 |
| 189 | m.p. | 72-74 |

TABLE 10

| Compound No. | m.p. (° C.) or refractive indx | $(n_D^{20})$ |
|---|---|---|
| 190 | m.p. | 180-181 |
| 192 | m.p. | 182-184 |
| 193 | refractive index | 1.5065 |
| 194 | m.p. | 42-45 |
| 195 | refractive index | 1.5445 |
| 196 | m.p. | 150-151 |
| 197 | m.p. | 155-157 |
| 198 | m.p. | 174-175 |
| 200 | m.p. | 151-154 |
| 201 | m.p. | 168-171 |
| 202 | m.p. | 168-171 |
| 203 | m.p. | 92-94 |
| 204 | m.p. | 143-145 |
| 206 | m.p. | 90-92 |
| 207 | m.p. | 128-129 |
| 208 | m.p. | 202-203 |
| 209 | refractive index | 1.4939 |
| 210 | m.p. | 95-97 |
| 212 | m.p. | 92-94 |

$^1$H-NMR data (CDCl$_3$/TMS δ(ppm) value) of the Compounds Nos. 49, 59, 101, 128, 158, 184, 185, 193, 195 and 209 will be shown below.

Compound No. 49: 2.56(3H, s), 3.40(2H, q), 5.29(2H, s), 7.21(1H, d), 7, 67(1H, d)

Compound No. 59: 1.22-1.28(3H, m), 2.55(3H, s), 3.40(2H, q), 3.46-3.55(2H, m), 4.12(1H, t), 7.20(1H, d), 7.63(1H, d)

Compound No. 101: 2.54(3H, s), 3.07(3H, d), 3.3.9(2H, q), 4.25(1H, s), 7.17(1H, d), 7.61(1H, d)

Compound No. 128: 1.32(6H, t), 2.50(3H, s), 3.25(4H, q), 3.44(2H, q), 7.19(1H, s), 7.75(1H, s)

Compound No. 158: 1.98(3H, s), 2.56(3H, s), 3.05(3H, s), 3.36(2H, q), 3.85(2H, q), 7.16 (1H, d), 7.61(1H, d)

Compound No. 184: 2.29(1H, d), 2.53(3H, s), 3.39(2H, q), 3.82(2H, q), 4.20(2H, dd), 4.34(1H, s), 7.16(1H, d), 7.61 (1H, d)

Compound No. 185: 2, 29(1H, t), 2.47(3H, s), 3.42-3.57(2H, m), 3.83(2H, q), 4.22(2H, d), 4.40(1H, s), 7.22(1H, s), 8.12(1H, s)

Compound No. 193: 2.30(1H, t), 2.55(3H, s), 3.40(2H, q), 4.24(2H, q), 4.40(1H, s), 7.20(1H, d), 7.63(1H, d)

Compound No. 195: 1.22-1.39(1H, m), 1.48-1.57(1H, m), 2.06-2.14(1H, m), 2.52(3H, s), 3.07(1H, dd), 3.29(1H, dd), 3.42, (2H, t), 4.75(2H, s), 7.16(1H, d), 7.65(1H, d)

Compound No. 209: 2.61(3H, s), 3.42(2H, q), 7.31(1H, d), 7.74(1H, d)

Now, an Example of Preparation of Intermediate will be shown below.

Intermediate Preparation Example 1

(1) Synthesis of 5-acetylthio-2,4-dimethylacetanilide 78 g of 2-fluoro-4-methylacetanilide was added to 168 g of chlorosulfonic acid at 40° C. or lower, followed by stirring at 70° C. for 2 hours. The reaction mixture was poured into ice water/ethyl acetate, the organic layer was washed with water and dried over anhydrous magnesium sulfate, and the solvent was distilled off under reduced pressure to obtain solid residue. The obtained solid residue was dissolved in 200 ml of acetic acid, and the resulting solution was added dropwise to a mixed solution of 72 g of red phosphorus, 1 g of iodine and 300 ml of acetic acid under reflux with heating over a period of 1 hour, followed by reflux with heating further for 4 hours. The insolubles were filtered off, acetic acid was distilled off under reduced pressure, water was added, and the residue was extracted with ethyl acetate. The organic layer was washed with water and dried over anhydrous magnesium sulfate. The solvent was distilled off under reduced pressure to obtain 42 g of 5-acetylthio-2,4-dimethylacetanilide.

(2) Synthesis of 2-fluoro-4-methyl-5-mercaptoaniline 42 g of 5-acetylthio-2-fluoro-4-methylacetanilide was added to a 5% aqueous potassium hydroxide solution, followed by reflux with heating for 18 hours. After the reaction mixture was cooled to room temperature, it was adjusted to have a pH 7 with diluted hydrochloric acid and extracted with ethyl acetate. The organic layer was dried over anhydrous magnesium sulfate, and the solvent was distilled off under reduced pressure to obtain 25 g of 2,4-dimethyl-5-merpcatoaniline.

(3) Synthesis of 2,4-dimethyl-5-(2,2,2-trifluoroethylthio)aniline

To a mixed solution of 20 g of 2,4-dimethyl-5-mercaptoaniline and 150 ml of N,N-dimethylformamide, 41 g of 2,2,2-trifluoroethyl iodide and 24 g of potassium carbonate were added, and 4 g of Rongalit was further added, followed by stirring at room temperature for 24 hours. The reaction mixture was poured into water and extracted with ethyl acetate. The organic layer was dried over anhydrous magnesium sulfate, and the solvent was distilled off under reduced pressure, and the obtained residue was purified by silica gel column chromatography (eluent hexane:ethyl acetate=5:1) to obtain 29 g of 2,4-dimethyl-5-(2,2,2-trifluoroethylthio)aniline.

$^1$H-NMR data (CDCl$_3$/TMS δ (ppm) value): 2.13 (3H, s), 3.34 (3H, s), 3.32 (2H, q), 3.52 (2H, s), 6.84 (1H, s), 6.91 (1H, s)

Now, formulation methods will be described in detail with reference to typical Formulation Examples. However, it should be understood that the types and the proportions of the compounds and the adjuvants are not restricted by these specific Examples and may be varied within wide ranges. In the following description, "part(s)" means "part(s) by weight".

Formulation Example 1

Emulsifiable Concentrate

Compound No. 6 (30 parts), cyclohexanone (20 parts), polyoxyethylene alkyl aryl ether (11 parts), calcium alkylbenzenesulfonate (4 parts) and methylnaphthalene (35 parts) were uniformly dissolved to obtain an emulsifiable concentrate.

Formulation Example 2

Wettable Powder

Compound No. 2 (10 parts), sodium salt of a naphthalenesulfonic acid/formalin condensate (0.5 part), polyoxyethylene alkyl aryl ether (0.5 part), diatomaceous earth (24 parts) and clay (65 parts) were uniformly mixed and pulverized to obtain a wettable powder.

Formulation Example 3

Dust

Compound No. 6 (2 parts), diatomaceous earth (5 parts) and clay (93 parts) were uniformly mixed and pulverized to obtain a dust.

Formulation Example 4

Granule

Compound No. 2 (5 parts), sodium lauryl alcohol sulfate (2 parts), sodium lignin sulfonate (5 parts), carboxymethylcellulose (2 parts) and clay (86 parts) were uniformly mixed and pulverized. Water (20 parts) was added to this mixture (100 parts) and they were kneaded, formed into granules of from 14 to 32 mesh by an extrusion-type granulator and dried to obtain a granule formulation.

Now, the effects of the pesticides containing the compounds of the present invention as active ingredients will be described with reference to Test Examples. Comparative Compounds a and b are Compounds [VI-208] and [VI-226] disclosed in JP-A-2000-198768:

(a)

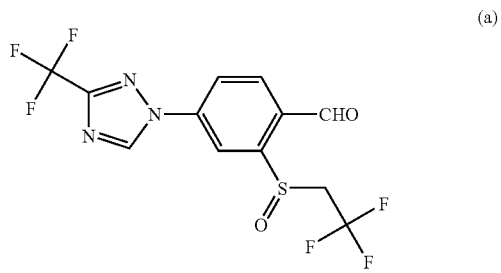

(b)

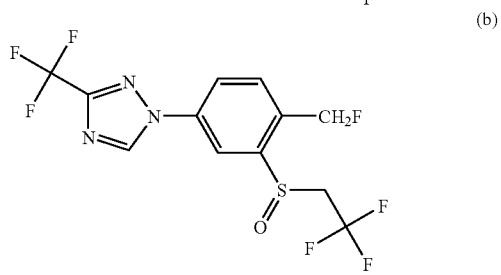

Test Example 1

Miticidal Test on Two-spotted Spider Mites (By Dipping)

Wettable powders were prepared in accordance with Formulation Example 2 and diluted with water to an active ingredient concentration of 500 ppm. Soybean seedlings which had been inoculated with imago two-spotted spider mites were dipped in the resulting solutions and dried in air. The treated seedlings were placed in a thermostatic chamber at 25° C. for 13 days, and the mite survivors were counted for calculation of the miticidal value by using Equation 2. The test was carried out by one series system. The results of this test are shown in Tables 11 and 12.

TABLE 11

| Compound No. | Miticidal value |
|---|---|
| 1 | 100 |
| 2 | 100 |
| 4 | 100 |
| 5 | 100 |
| 6 | 100 |
| 8 | 100 |
| 28 | 100 |

TABLE 11-continued

| Compound No. | Miticidal value |
|---|---|
| 30 | 100 |
| 32 | 100 |
| 35 | 100 |
| 36 | 100 |
| 37 | 100 |
| 38 | 100 |
| 43 | 100 |
| 50 | 100 |
| 56 | 100 |
| 60 | 100 |
| 66 | 100 |
| 76 | 100 |
| 80 | 100 |
| 84 | 100 |
| 98 | 100 |
| 99 | 100 |
| 102 | 100 |
| 104 | 100 |
| 106 | 100 |
| 106 | 100 |
| 107 | 100 |
| 111 | 100 |
| 113 | 100 |

TABLE 12

| Compound No. | Miticidal value |
|---|---|
| 114 | 100 |
| 115 | 100 |
| 117 | 100 |
| 119 | 100 |
| 121 | 100 |
| 123 | 100 |
| 125 | 100 |
| 127 | 100 |
| 131 | 100 |
| 133 | 100 |
| 144 | 100 |
| 145 | 100 |
| 147 | 100 |
| 153 | 100 |
| 155 | 100 |
| 157 | 100 |
| 161 | 100 |
| 162 | 100 |
| 167 | 100 |
| 169 | 100 |
| 171 | 100 |
| 177 | 100 |
| 179 | 100 |
| 183 | 100 |
| 185 | 100 |
| 187 | 100 |
| 190 | 100 |
| 192 | 100 |
| 194 | 100 |
| 202 | 100 |
| 212 | 100 |
| Comparative compound a | 100 |
| Comparative compound b | 99 |

Test Example 2

Miticidal Test on Two-spotted Spider Mites (By Soil Drenching)

Wettable powders were prepared in accordance with Formulation Example 2 and diluted with water to an active ingredient concentration of 100 ppm. 100 g of the soil in cups with soybean seedlings which had been inoculated with imago two-spotted spider mites were drenched with 5 ml of the resulting solutions. The treated seedlings were placed in a thermoplastic chamber at 25° C. for 13 days, and the mite survivors were counted for calculation of the miticidal value by using Equation 2. The results of this test are shown in Tables 13 and 14.

TABLE 13

| Compound No. | Miticidal value |
|---|---|
| 1 | 99 |
| 2 | 100 |
| 4 | 100 |
| 5 | 100 |
| 6 | 100 |
| 8 | 100 |
| 28 | 100 |
| 30 | 100 |
| 32 | 100 |
| 35 | 93 |
| 36 | 100 |
| 37 | 100 |
| 38 | 100 |
| 43 | 100 |
| 50 | 100 |
| 56 | 100 |
| 60 | 100 |
| 66 | 100 |
| 76 | 100 |
| 80 | 100 |
| 84 | 100 |
| 98 | 100 |
| 99 | 100 |
| 102 | 100 |
| 104 | 100 |
| 106 | 100 |
| 106 | 100 |
| 107 | 100 |
| 111 | 100 |
| 113 | 100 |
| 114 | 100 |
| 115 | 100 |
| 117 | 100 |
| 119 | 100 |
| 121 | 100 |
| 123 | 100 |

TABLE 14

| Compound No. | Miticidal value |
|---|---|
| 125 | 99 |
| 127 | 100 |
| 131 | 100 |
| 133 | 100 |
| 144 | 100 |
| 145 | 100 |
| 147 | 100 |
| 153 | 100 |
| 155 | 100 |
| 157 | 100 |
| 161 | 100 |
| 162 | 95 |
| 167 | 100 |
| 169 | 100 |
| 171 | 100 |
| 177 | 100 |
| 179 | 100 |
| 183 | 100 |
| 185 | 100 |
| 187 | 99 |
| 190 | 100 |
| 192 | 100 |
| 194 | 100 |
| 202 | 100 |
| 212 | 100 |
| Comparative compound a | 0 |
| Comparative compound b | 0 |

Test Example 3

Insecticidal Test on Brown Planthoppers

Wettable powders were prepared in accordance with Formulation Example 2 and diluted with water to an active ingredient concentration of 500 ppm. Germinating rice was immersed in the resulting solutions and put in a plastic cup with a capacity of 60 ml. Ten 4th-instar larvae of brown planthoppers were released to the cup, and the cup was covered and placed in a thermostatic chamber at 25° C. for 6 days, and the survivors were counted for calculation of the insecticidal degree by using Equation 1. The test was carried out by one series system. The results of this test are shown in Tables 15 and 16.

TABLE 15

| Compound No. | Insecticidal degree (%) |
| --- | --- |
| 1 | 90 |
| 2 | 100 |
| 4 | 90 |
| 5 | 100 |
| 6 | 100 |
| 11 | 90 |
| 17 | 100 |
| 20 | 100 |
| 23 | 90 |
| 24 | 90 |
| 26 | 90 |
| 27 | 100 |
| 28 | 100 |
| 31 | 100 |
| 32 | 100 |
| 37 | 100 |
| 38 | 100 |
| 39 | 100 |
| 43 | 100 |
| 49 | 100 |
| 50 | 99 |
| 59 | 100 |
| 60 | 100 |
| 65 | 100 |
| 66 | 100 |
| 75 | 100 |
| 76 | 100 |
| 79 | 100 |
| 80 | 100 |
| 83 | 10 |
| 84 | 100 |
| 99 | 100 |
| 101 | 100 |
| 102 | 100 |
| 105 | 90 |
| 106 | 90 |
| 111 | 100 |
| 112 | 90 |
| 113 | 100 |
| 114 | 100 |
| 115 | 100 |
| 117 | 100 |
| 119 | 90 |
| 124 | 100 |

TABLES 16

| Compound No. | Insecticidal degree (%) |
| --- | --- |
| 125 | 100 |
| 127 | 100 |
| 128 | 100 |
| 131 | 90 |
| 133 | 100 |
| 137 | 100 |
| 141 | 100 |
| 144 | 90 |
| 148 | 100 |
| 150 | 100 |
| 153 | 100 |
| 155 | 90 |
| 157 | 100 |
| 158 | 90 |
| 160 | 100 |
| 161 | 100 |
| 162 | 100 |
| 163 | 100 |
| 164 | 100 |
| 165 | 100 |
| 167 | 100 |
| 168 | 100 |
| 169 | 100 |
| 170 | 100 |
| 171 | 100 |
| 174 | 90 |
| 176 | 90 |
| 179 | 100 |
| 184 | 100 |
| 185 | 100 |
| 186 | 100 |
| 187 | 100 |
| 189 | 100 |
| 190 | 100 |
| 192 | 100 |
| 193 | 100 |
| 194 | 100 |
| 195 | 100 |
| 200 | 100 |
| 201 | 100 |
| 202 | 100 |
| 212 | 100 |

Test Example

Nemastatic Test on Southern Root-knot Nematodes

Compounds of the present invention (5 parts) and Tween 20 (tradename for polyoxyethylene sorbitan monolaurate) (1 part) as a spreader were dissolved n N,N-dimethylformamide (94 parts) to prepare 5% emulsifiable concentrates of the compounds of the present invention. Distilled water was added to the emulsifiable concentrates to prepare diluted solutions having a concentration of the compounds of the present invention of 20 ppm. 0.5 ml of the diluted solutions and 0.5 ml of water suspensions containing 100 second stage larvae of southern root-knot nematodes were mixed, and the mixture were placed in a thermostatic chamber at 25° C. for 5 days, and the survivors were counted for calculation of the nemastatic degree by using Equation 3. The test was carried out by two series system. The results of this test are shown in Tables 17 and 18.

TABLE 17

| Compound No. | Nemastatic degree (%) |
| --- | --- |
| 1 | 100 |
| 2 | 100 |
| 3 | 100 |
| 6 | 100 |
| 15 | 100 |
| 17 | 99 |
| 20 | 92 |
| 21 | 100 |
| 23 | 100 |

TABLE 17-continued

| Compound No. | Nemastatic degree (%) |
|---|---|
| 27 | 100 |
| 30 | 95 |
| 31 | 100 |
| 35 | 100 |
| 36 | 100 |
| 38 | 100 |
| 39 | 100 |
| 43 | 93 |
| 50 | 98 |
| 59 | 100 |
| 65 | 100 |
| 66 | 94 |
| 75 | 94 |
| 79 | 94 |
| 97 | 97 |
| 101 | 98 |
| 102 | 98 |
| 103 | 94 |
| 110 | 97 |
| 114 | 100 |
| 115 | 92 |
| 116 | 97 |

TABLE 18

| Compound No. | Nemastatic degree (%) |
|---|---|
| 123 | 98 |
| 124 | 100 |
| 125 | 91 |
| 126 | 94 |
| 127 | 94 |
| 130 | 100 |
| 131 | 93 |
| 133 | 98 |
| 140 | 99 |
| 141 | 97 |
| 144 | 97 |
| 146 | 98 |
| 148 | 99 |
| 160 | 100 |
| 161 | 98 |
| 162 | 100 |
| 164 | 100 |
| 168 | 100 |
| 170 | 100 |
| 171 | 100 |
| 174 | 100 |
| 175 | 97 |
| 176 | 97 |
| 182 | 91 |
| 193 | 100 |
| 203 | 92 |
| 207 | 100 |
| 208 | 100 |
| 209 | 100 |
| 212 | 100 |

$$\text{Insecticidal degree (\%)} = \frac{10 - \text{number of survivors in the treated area}}{10} \times 100 \quad \text{Equation 1}$$

$$\text{Miticidal value (\%)} = \left(1 - \frac{\begin{array}{c}\text{number of adult mites}\\\text{in the control area}\\\text{before treatment}\end{array}}{\begin{array}{c}\text{number of adult mites}\\\text{in the treated area}\\\text{before treatment}\end{array}} \times \frac{\begin{array}{c}\text{number of adult mites}\\\text{in the treated area on}\\\text{the date of survey}\end{array}}{\begin{array}{c}\text{number of adult mites}\\\text{in the control area on}\\\text{the date of survey}\end{array}}\right) \times 100 \quad \text{Equation 2}$$

$$\text{Nemastatic degree (\%)} = \frac{\begin{array}{c}\text{number of survivors}\\\text{in the control area}\end{array} - \begin{array}{c}\text{number of survivors}\\\text{in the treated area}\end{array}}{\text{number of survivors in the control area}} \times 100 \quad \text{Equation 3}$$

INDUSTRIAL APPLICABILITY

3-Triazolylphenyl sulfide derivatives of the present invention exhibit outstanding effects on various farm and garden pests, especially on mites, pest lepidoptera, pest hemiptera, pest coleoptera and nematodes, and they can be widely used as insecticides, miticides and nematicides having soil treatment activity with which safe and labor-saving application becomes possible.

The entire disclosure of Japanese Patent Application No. 2004-305251 filed on Oct. 20, 2004 including specification, claims and summary are incorporated herein by reference in its entirety.

The invention claimed is
1. A 3-Triazolylphenyl sulfide derivative represented by the formula [I]:

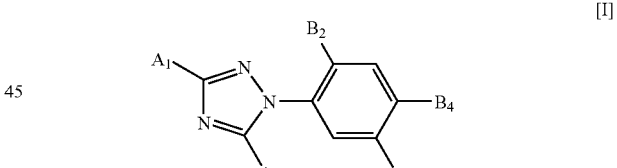

wherein either
R is a trifluoroethyl group;
n is an integer of 1;
$A_1$ is a trifluoromethyl group;
$A_3$ is a methylamino group;
$B_2$ is a halogen atom; and
$B_4$ is a methyl group; or
R is a trifluoroethyl group;
n is an integer of 1;
$A_1$ is a trifluoromethyl group or a trifluoromethylthio group;
$A_3$ is an amino group;
$B_2$ is a halogen atom; and
$B_4$ is a methyl group.

2. A 3-Triazolylphenyl sulfide derivative of claim 1 represented by the formula [I]:

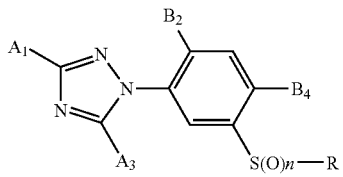

[I]

wherein
R is a trifluoroethyl group;
n is an integer of 1;
$A_1$ is a trifluoromethyl group;
$A_3$ is a methylamino group;
$B_2$ is a halogen atom; and
$B_4$ is a methyl group.

3. A 3-Triazolylphenyl sulfide derivative of claim 1 represented by the formula [I]:

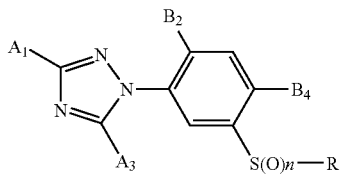

[I]

wherein
R is a trifluoroethyl group;
n is an integer of 1;
$A_1$ is a trifluoromethyl group or a trifluoromethylthio group;
$A_3$ is an amino group;
$B_2$ is a halogen atom; and
$B_4$ is a methyl group.

4. An insecticide, miticide or nematicide formulation having soil treatment miticidal activity, for agriculture and horticulture, comprising the 3-triazolylphenyl sulfide derivative as defined in claim 2 as an active ingredient and an adjuvant.

5. An insecticide, miticide or nematicide formulation having soil treatment miticidal activity, for agriculture and horticulture, comprising the 3-triazolylphenyl sulfide derivative as defined in claim 3 as an active ingredient and an adjuvant.

6. An insecticide, miticide or nematicide formulation having soil treatment miticidal activity, for agriculture and horticulture, comprising the 3-triazolylphenyl sulfide derivative as defined in claim 1 as an active ingredient and a diluent.

7. A miticidal formulation having soil treatment miticidal activity, comprising the 3-triazolylphenyl sulfide derivative as defined in claim 2 as an active ingredient and water, wherein the active ingredient is diluted with water to a concentration of from 0.1 to 5000 ppm.

8. A miticidal formulation having soil treatment miticidal activity, comprising the 3-triazolylphenyl sulfide derivative as defined in claim 2 as an active ingredient and water, wherein the active ingredient is diluted with water to a concentration of from 0.1 to 500 ppm.

9. A miticidal formulation having soil treatment miticidal activity, comprising the 3-triazolylphenyl sulfide derivative as defined in claim 2 as an active ingredient and water, wherein the active ingredient is diluted with water to a concentration of from 0.1 to 100 ppm.

10. A miticidal formulation having soil treatment miticidal activity, comprising the 3-triazolylphenyl sulfide derivative as defined in claim 2 as an active ingredient and water, wherein the active ingredient is diluted with water to a concentration of from 0.1 to 5000 ppm.

11. A miticidal formulation having soil treatment miticidal activity, comprising the 3-triazolylphenyl sulfide derivative as defined in claim 2 as an active ingredient and water, wherein the active ingredient is diluted with water to a concentration of from 0.1 to 500 ppm.

12. A miticidal formulation having soil treatment miticidal activity, comprising the 3-triazolylphenyl sulfide derivative as defined in claim 2 as an active ingredient and water, wherein the active ingredient is diluted with water to a concentration of from 0.1 to 100 ppm.

\* \* \* \* \*